in accordance with the present invention, tetracyclic caboline derivatives that inhibit the expression of VEGF post-transcriptionally have been identified, and methods for their use provided. In one aspect of the invention, these compounds useful in the inhibition of VEGF production, in the inhibition of angiogenesis, and/or in the treatment of cancer, diabetic retinopathy or exudative macular degeneration are provided. In another aspect of the invention, methods are provided for the inhibition of VEGF production, the inhibition of angiogenesis, and/or the treatment of cancer, diabetic retinopathy or exudative macular degeneration using the compounds of the invention.

(12) United States Patent
Moon et al.

(10) Patent No.: US 8,940,896 B2
(45) Date of Patent: Jan. 27, 2015

(54) TETRA-CYCLIC CARBOLINE DERIVATIVES USEFUL IN THE INHIBITION OF ANGIOGENESIS

(75) Inventors: Young-Choon Moon, Belle Mead, NJ (US); Liangxian Cao, Parlin, NJ (US); Nadarajan Tamilarasu, Edison, NJ (US); Hongyan Qi, Plainsboro, NJ (US); Soongyu Choi, Skillman, NJ (US); William Joseph Lennox, South Plainfield, NJ (US); Donald Thomas Corson, Annandale, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1756 days.

(21) Appl. No.: 10/592,761

(22) PCT Filed: Mar. 15, 2005

(86) PCT No.: PCT/US2005/008452
§ 371 (c)(1),
(2), (4) Date: Nov. 27, 2007

(87) PCT Pub. No.: WO2005/089752
PCT Pub. Date: Sep. 29, 2005

(65) Prior Publication Data
US 2008/0182866 A1    Jul. 31, 2008

Related U.S. Application Data

(60) Provisional application No. 60/552,724, filed on Mar. 15, 2004.

(51) Int. Cl.
*C07D 235/02* (2006.01)
*A61K 31/4166* (2006.01)
*C07D 221/18* (2006.01)
*C07D 239/26* (2006.01)
*C07D 265/30* (2006.01)
*C07D 307/78* (2006.01)
*C07D 317/48* (2006.01)
*C07D 241/04* (2006.01)

(52) U.S. Cl.
CPC .......... *A61K 31/4166* (2013.01); *C07D 235/02* (2013.01); *C07D 221/18* (2013.01); *C07D 239/26* (2013.01); *C07D 265/30* (2013.01); *C07D 307/78* (2013.01); *C07D 317/48* (2013.01); *C07D 241/04* (2013.01)
USPC ........................................................ 546/64

(58) Field of Classification Search
CPC .. C07D 235/02; C07D 221/18; C07D 239/26; C07D 241/04; C07D 265/30; C07D 307/78; C07D 317/48
USPC ......................................................... 546/64
See application file for complete search history.

(56) References Cited

U.S. PATENT DOCUMENTS

| | | | |
|---|---|---|---|
| 4,014,890 A | 3/1977 | Welch, Jr. et al. |
| 5,166,204 A | 11/1992 | Nagai et al. |
| 5,451,600 A | 9/1995 | Banner et al. |
| 6,175,015 B1 | 1/2001 | Yuan et al. |
| 6,706,750 B1 | 3/2004 | Bentley et al. |
| 2005/0004156 A1 | 1/2005 | Feng et al. |

FOREIGN PATENT DOCUMENTS

| | | |
|---|---|---|
| JP | 11-509517 A | 8/1999 |
| WO | WO 96/32003 | 10/1996 |
| WO | WO 02/28865 | 4/2002 |
| WO | 02/095361 A2 | 11/2002 |
| WO | WO 2004/069831 | 8/2004 |
| WO | WO 2004/096766 | 11/2004 |

OTHER PUBLICATIONS

Vippagunta. Adv. Drug Del. Rev., vol. 48, (2001), pp. 3-26.*
Lopez-Rodriguez et al. J. Org. Chem., 1994, vol. 59, pp. 1583-1585.*
International Search Report issued in PCT/US2005/042484 on Oct. 4, 2006.
Shanmugasundaram et al., "Synthesis and biological activity of pyrazino[3,2,1-j,k]carbazoles", *Indian Journal of Chemistry*, 37b:1133-1136 (1998).
Shanmugasundaram et al., "Synthesis of 3-Phenylisoxazolo[3,4-a]carbazoles", *Zeitschrift Für Naturforschung*, 54b:1202-1204 (1999).
Daugan et al., "The Discovery of Tadalafil: A Novel and Highly Selective PDE5 Inhibitor. 1: 5,6,11,11a-Tetrahydro-1H-imidazo[1',5':1,6]pyrido[3,4-b]indole-1,3(2H)-dione Analogues," *J. Med. Chem.*, 46:4525-4532.
Daugan et al., "The Discovery of Tadalafil: A Novel and Highly Selective PDE5 Inhibitor. 2: 2,3,6,7,12,12a-hexahydropyrazino[1',2':1,6]pyrido[3,4-b]indole-1,4-dione Analogues," *J. Med. Chem.*, 46:4533-4542 (2003).
International Search Report of International Application No. PCT/US2005/008452, issued Oct. 24, 2005.
Marcus et al., "Mitotic Kinesin Inhibitors Induce Mitotic Arrest and Cell Death in Taxol-resistant and -sensitive Cancer Cells," *Journal of Biological Chemistry*, 280(12):11569-11577 (2005).
Braña, et al., "Synthesis and Reactivity of β-Carboline-Hydantoin Systems." Synthetic Communications, 20(12), 1990, pp. 1793-1810.
Braña, et al., "Synthesis of New Derivatives of β-Carboline-hydantoin", J. Heterocyclic Chem., vol. 27, 1990, pp. 703-706.

(Continued)

*Primary Examiner* — James D Anderson
(74) *Attorney, Agent, or Firm* — Hoffmann & Baron, LLP

(57) ABSTRACT

In accordance with the present invention, tetracyclic caboline derivatives that inhibit the expression of VEGF post-transcriptionally have been identified, and methods for their use provided. In one aspect of the invention, these compounds useful in the inhibition of VEGF production, in the inhibition of angiogenesis, and/or in the treatment of cancer, diabetic retinopathy or exudative macular degeneration are provided. In another aspect of the invention, methods are provided for the inhibition of VEGF production, the inhibition of angiogenesis, and/or the treatment of cancer, diabetic retinopathy or exudative macular degeneration using the compounds of the invention.

9 Claims, 2 Drawing Sheets

(56) References Cited

OTHER PUBLICATIONS

Bonnet and Ganesan, "Solid-Phase Synthesis of Tetrahydro-β-carbolinehydantoins via the N-Acyliminium Pictet-Spengler Reaction and Cyclative Cleavage", J. Comb. Chem., 2002, 4, 546-548.

de Miguel, et al., "Synthesis of Tetrahydroimidazo[1,5-b]-β-carboline Derivatives with Complex Basic Substituents", J. Heterocyclic Chem., 31, 1235-1239 (1994).

Lopez-Rodriguez, et al., "α1-Adrenoceptor Reagents. Synthesis of Some 5,6,11,11a-Tetrahydro-1H-imidazo [1',5' :1,6]pyrido and 5,6,11,11b-Tetrahydro-1H-imidazo-[1',5' : 1,2]pyrido[3,4-b]indole-1,3(2H)-diones", Chem. Pharm. Bull., 43(6), 941-946 (1995).

Lopez Rodriguez, et al., "Reaction of 6-Hydroxytetrahydro-β-carboline-3-carboxylic Acids with Isocyanates and Isothiocyanates", Chem. Pharm. Bull., 42(10), 2108-2112 (1994).

Wang and Ganesan, "A Biomimetic Total Synthesis of (-)-Spirotryprostatin B and Related Studies", J. Org. Chem., 2000, 65, 4685-4693.

English-language translation of Notice of Reasons for Rejection for Japanese Patent Application No. 2007-503999 with Notice of Reasons for Rejection issued for Japanese Patent Application No. 2007-503999 in Japanese.

* cited by examiner

TETRA-CYCLIC CARBOLINE DERIVATIVES USEFUL IN THE INHIBITION OF ANGIOGENESIS

CROSS REFERENCE TO RELATED APPLICATIONS

This application is a national phase application under 35 U.S.C. §371 of International Application Number PCT/US2005/008452, filed Mar. 15, 2005, which application claims the benefit of and priority to U.S. Provisional Application No. 60/552,724, filed Mar. 15, 2004, which U.S. Provisional application is incorporated herein by reference.

FIELD OF THE INVENTION

The present invention relates to methods and compounds for inhibiting angiogenesis. More particularly, the present invention relates to methods and compounds for inhibiting angiogenesis.

BACKGROUND OF THE INVENTION

Aberrant angiogenesis plays a critical role in the pathogenesis of numerous diseases, including malignant, ischemic, inflammatory and immune disorders (Carmeliet, Nat. Med., 9(6):653-60 (2003), Ferrara, Semin. Oncol., 29(6 Suppl 16): 10-4 (2002)). The best-known of these disorders are cancer, exudative macular degeneration and diabetic retinopathy (DR), the last two of which are leading cause of blindness in the United States (Witmer et al., Prog. Retin Eye Res., 22(1): 1-29 (2003), Clark et al., Nat. Rev. Drug Discovery, 2:448-459 (2003)). During the last decade our understanding of the molecular basis of angiogenesis has grown considerably. Numerous cytokines and growth factors that stimulate angiogenesis, such as VEGF, FGF-2, PDGF, IGF-1, TGF, TNF-α, G-CSF have been identified (Ferrara et al., Nat. Med., 5(12): 1359-64 (1999), Kerbel et al., Nat. Rev. Cancer, 2(10):727-39 (2002), Rofstad et al., Cancer Res., 60(17):4932-8 (2000)). Among these growth factors, Vascular Endothelial Growth Factor (VEGF) plays a central role in angiogenesis (Ferrara, Semin. Oncol., 29(6 Suppl 16):10-4 (2002)).

VEGF, also known as VEGF-A, was initially identified for its ability to induce vascular permeability and to promote vascular endothelial cell proliferation (Leung et al., Science, 246:1306-1309 (1989), Plouet et al., EMBO J., 8:3801-3806 (1989), Connolly et al., J. Biol. Chem., 264:20017-20024 (1989)). VEGF is encoded by a single gene that gives rise to four isoforms by alternative splicing (Tischer et al., J. Biol. Chem., 266:11947-11954 (1991)). All four isoforms share the same unusually long and GC rich 5'-UTR, as well as a 3'-UTR that includes multiple RNA stability determinants. The receptors VEGFR-2 (also known as KDR or Flk-1) and VEGFR-1 (previously known as Flt1) recognize the dimeric form of VEGF (Ortega et al., Front. Biosci., 4:D141-52 (1999), Sato et al., Annals of New York Academy of Science, 902:201-207, (2000)). The highly specific VEGFR-2 receptor is expressed on endothelial cells. VEGF binding to the VEGFR-2 receptor activates the receptor's tyrosine kinase activity, leading to endothelial cell proliferation, differentiation and primitive vessel formation (Shalaby et al., Nature, 376:62-66, (1995)). VEGFR-1 inhibits endothelial cell growth either by acting as a decoy or by suppressing signaling pathways through VEGFR-2 (Fong et al., Nature, 376:66-70 (1995)).

Over 30 years ago, it was proposed that inhibition of tumor angiogenesis could be an effective approach for the treatment of cancer (Folkman, N. Engl. J. Med., 285(21):1182-6 (1971)). VEGF and its receptor have been demonstrated to have a central role in tumor angiogenesis, especially in the early stages of tumor growth (Hanahan et al., Cell, 86:353-364, 1996)). Indeed, increased levels of VEGF expression have been correlated with microvessel density in primary tumor tissues (Gasparini et al., J. Natl. Cancer Inst., 89:139-147 (1997)). Moreover, increased levels of the VEGF transcript are found in virtually all of the common solid tumors (Ferrara et al., Endocr. Rev., 18:4-25, 1997)). In general, tumor-bearing patients have higher levels of VEGF compared to those in tumor-free individuals, and high VEGF levels in serum/plasma are associated with poor prognosis (Dirix et al., Br. J. Cancer, 76:238-243 (1997)). Consistent with the role of VEGF in tumor angiogenesis, VEGF null embryonic stem cells showed a dramatically reduced ability to form tumors in nude mice (Carmeliet et al., Nature, 380:435-439 (1996)). Direct evidence for the involvement of VEGF in tumorgenesis was demonstrated by using specific antibodies against VEGF in human xenografts implanted in nude mice (Kim et al., Nature, 362:841-844 (1993), Hichlin et al., Drug Discovery Today, 6:517-528 (2001)). In these studies, the inhibition of tumor growth correlated positively with decreased vessel formation in the antibody-treated tumors. Subsequent experiments using the soluble receptors substantiated the importance of VEGF activity in tumor growth (Lin et al., Cell Growth Differ., 9(1):49-58 (1998)), and demonstrated that inactivation of VEGF by specific antibody treatment directly resulted in a nearly complete suppression of tumor-associated neovascularization (Borgstrom et al., Prostate, 35:1-10 (1998), Yuan et al. Proc. Natl. Acad. Sci. USA, 93:14765-14770 (1996)).

In exudative macular degeneration and diabetic retinopathy, pre-clinical experiments and clinical trials have demonstrated that over production of VEGF is critical for aberrant retinal or choroidal neovascularization (reviewed in Witmer et al., Prog. Retin Eye Res., 22(1):1-29 (2003)). Evidence has been obtained that intra-ocular VEGF levels are strongly correlated with active retinal/choroidal neovascularization (CNV) in patients with diseases such as diabetic retinopathy and wet form macular degeneration (Funatsu et al., Am. J. Opthalmol., 133(4):537-43 (2002), Lip et al., Opthalmology, 108(4):705-10 (2001)). In addition, studies using transgenic mice demonstrated that overexpression of VEGF in retinal pigment epithelial cells or photoreceptor cells results in choroidal or retinal neovasucularization (Schwesinger et al., Am. J. Pathol., 158(3):1161-72 (2001), Ohno-Matsui et al., Am. J. Pathol., 160(2):711-9 (2002)). In recent studies neutralizing antibodies, soluble receptor, receptor antagonists, or siRNA have proven efficacious in reducing VEGF-mediated blood vessel formation in animal models and in the clinic (Eyetech Study Group, 22(2):143-52 (2002), Krzystolik et al., Arch. Opthalmol., 120(3):338-46 (2002), Shen et al., Lab Invest., 82(2):167-82 (2002), Honda et al., Gene Ther., 7(11):978-85 (2000), Saishin et al., J. Cell Physiol., 195(2):241-8 (2003)).

VEGF expression is regulated by a number of factors and agents including cytokines, growth factors, steroid hormones and chemicals, and mutations that modulate the activity of oncogenes such as ras or the tumor suppressor gene VHL (Maxwell et al., Nature, 399:271-275 (1999), Rak et al., Cancer Res., 60:490-498 (2000)). Nevertheless, hypoxia is the most significant physiologic signal for regulating VEGF expression. Hypoxia results in enhanced VEGF expression by increasing both the transcription rate and stability of the VEGF transcript (Ikeda et al., J. Biol. Chem. 270:19761-19766 (1995), Stein et al., Mol. Cell. Biol. 18:3112-3119 (1998), Levy et al., J. Biol. Chem. 271:2746-2753 (1996)). Hypoxia-inducible factor 1α (HIF-1α) is a transcription factor that increases VEGF gene expression in cells undergoing hypoxia by binding to the hypoxia response element (HRE) located in the VEGF promoter (Liu et al., Circ. Res., 77:638-643 (1995), Semenza, Annu. Rev. Cell. Dev. Biol., 5:551-578 (1999)). The stability of VEGF mRNA is also greatly enhanced as a consequence of the binding of factors to elements in the 3'-UTR (Goldberg et al., J. Biol. Cell. J. Biol. Chem., 277(16):13635-40 (2002)). In addition, the translation initiation of the VEGF transcript is uniquely regulated. Under hypoxic conditions, translation of most cellular transcripts mediated by cap-dependent translation initiation process is greatly impaired (Kraggerud et al., Anticancer Res., 15:683-686 (1995)). Initiation of translation of the VEGF mRNA, however, is unique under hypoxic conditions in that it is mediated via an internal ribosome entry site (IRES) within the VEGF 5'UTR (Stein et al., Mol. Cell. Biol. 18:3112-3119 (1998), Levy et al., J. Biol. Chem. 271:2746-2753 (1996), Huez et al., Mol. Cell. Biol., 18:6178-6190 (1998), Akiri et al., Oncogene, 17:227-236 (1998)).

There is a large body of experimental evidence indicating that tumor growth can be inhibited by the prevention of neovascularization (Lin et al., Cell Growth Differ., 9(1):49-58 (1998), Zhu et al., Invest. New Drugs, 17:195-212 (1999)). Tumor vessels are generally immature and constantly undergo remodeling (Carmeliet, Nat. Med., 9(6):653-60 (2003), Carmeliet et al., Nature, 407:249-257 (2000)). Active and aberrant angiogenesis is the result of a disruption in the normal balance of proangiogenic and anti-angiogenic factors, including various cytokines, growth factors and steroid hormones. Despite the complexity of the regulation of tumor angiogenesis, accumulated evidence indicates that targeting a single proangiogenic factor might be sufficient to inhibit tumor angiogenesis and suppress tumor growth (Kim et al., Nature, 362:841-844 (1993), Millauer et al., Nature, 367: 576-579 (1994), Fong et al., Cancer Res., 59:99-106 (1999)). Among many angiogenesis targets, VEGF and its receptor are most attractive (Carmeliet, Nat. Med., 9(6):653-60 (2003), Ortega et al., Front. Biosci., 4:D141-52 (1999)). As noted above, treatment with a monoclonal antibody specifically targeting VEGF inhibited the growth of tumors in human xenografts implanted in nude mice. Subsequently, various approaches designed to inactivate VEGF signaling have been tested in tumor models and have proven to be highly effective in a broad range of tumor cell lines including carcinomas, sarcomas and gliomas (Ferrara et al., Endocr. Rev., 18:4-25, 1997), Kim et al., Nature, 362:841-844 (1993), Millauer et al., Nature, 367:576-579 (1994), Fong et al., Cancer Res., 59:99-106 (1999), Geng et al., Cancer Res., 61:2413-2419 (2001)). In addition, inhibition of VEGF by anti-VEGF antibody did not result in significant side effects in fully developed rodents or primates (Ryan et al., Toxicol. Pathol., 27:78-86 (1999), Ferrara et al., Nat. Med., 4:336-340 (1998)). Taken together, these results indicate that VEGF is a valid target for the development of tumor therapy. Indeed, a number of clinical trials are underway using VEGF inhibitors (Matter, Drug Discovery Today, 6:1005-1024 (2001), Hichlin et al., Drug Discovery Today, 6:517-528 (2001)).

Although several pro-angiogenic factors are implicated in the pathology of exudative age-related macular degeneration, VEGF appears to be the most critical in the pathogenesis and development of this disease (Witmer et al., Prog. Retin Eye Res., 22(1):1-29 (2003), Holash et al., Science, 284:1994-1998 (1999)). Data from preclinical experiments and clinical trials have demonstrated that blockade of VEGF alone is sufficient to alleviate or stabilize disease progression (Eyetech Study Group, 22(2):143-52 (2002), Krzystolik et al., Arch. Opthalmol., 120(3):338-46 (2002), Shen et al., Lab Invest., 82(2):167-82 (2002), Honda et al., Gene Ther., 7(11): 978-85 (2000), Saishin et al., J. Cell Physiol., 195(2):241-8 (2003)). For example, inhibition of VEGFR signaling by a specific tyrosine kinase inhibitor is sufficient to completely prevent retinal neovascularization in a murine retinopathy of prematurity model (Ozaki H, Seo M S, Ozaki et al., Am. J. Pathol., 156(2):697-707 (2000)). Furthermore, it has recently been demonstrated that small interfering RNAs (siRNA) directed against murine VEGF significantly inhibited ocular neovascularization after laser photocoagulation in a mouse model (Reich et al., Mol. Vis. 30; 9:210-6 (2003)). These results indicate that selective inhibition of VEGF expression is achievable and offers validation of this approach for the treatment of ocular neovascular diseases such as exudative macular degeneration and diabetic retinopathy.

Three approaches have been used to inhibit VEGF activity, including (1) neutralization of VEGF activity by using a specific antibody, soluble VEGF receptor or aptamer oligos against the VEGF/VEGFR interaction (Kim et al., Nature, 362:841-844 (1993), Lin et al., Cell Growth Differ., 9(1):49-58 (1998), Borgstrom et al., Prostate, 35:1-10 (1998), Zhu et al., Invest. New Drugs, 17:195-212 (1999), Millauer et al., Nature, 367:576-579 (1994), Asano et al., Jpn. J. Cancer Res., 90(1):93-100 (1999), Brekken et al., Cancer Res., 60(18):5117-24 (2000)); (2) inhibition of VEGFR mediated signal transduction by specific small molecule tyrosine kinase inhibitors (Fong et al., Cancer Res., 59:99-106 (1999), Wedge et al., Cancer Res., 60(4):970-5 (2000), Laird et al., Cancer Res., 60(15):4152-60 (2000)); and (3) inhibition of VEGF/VEGFR expression by using antisense, siRNA or ribozyme (Reich et al., Mol. Vis. 30; 9:210-6 (2003), Parry et al., Nucleic Acids Res., 27:2569-2577 (1999), Ellis et al., Surgery, 120:871-878 (1996), Filleur et al., Cancer Res., 63(14):3919-22 (2003)). Although all of these approaches show significant inhibition of angiogenesis in vivo, they all possess significant limitations. For example, therapeutic proteins (antibody and soluble receptors) or oligos (antisense, siRNA and ribozyme) are large molecules with poor permeability that usually require parenteral administration and are costly to produce. For treatment of chronic ocular neovascularization, multiple injections may be impractical due to potential complications such as retinal detachment and procedure related infection. Moreover, tyrosine kinase inhibitors have the potential for limited specificity. VEGF is constitutively expressed at a low level in normal eyes and other tissues and thus it may be harmful to completely suppress VEGF function by administration of antibody or tyrosine kinase inhibitors systemically, especially for patients with AMD and RD many of whom are also hypertensive (Giles et al., Cancer, 97(8):1920-8 (2003), Sugimoto et al., J. Biol. Chem., 278 (15):12605-8 (2003), Bergsland et al., American Society of Clinical Oncology 36th Annual Meeting, 20-23 May, 2000, New Orleans, La., USA, Abstract 939), DeVore et al., American Society of Clinical Oncology 36th Annual Meeting, 20-23 May, 2000, New Orleans, La., USA, Abstract 1896).

Thus, there remains a need to develop, characterize and optimize lead molecules for the development of novel anti-angiogenesis drugs. Accordingly, it is an object of the present invention to provide such compounds.

All documents referred to herein are incorporated by reference into the present application as though fully set forth herein.

SUMMARY OF THE INVENTION

In accordance with the present invention, compounds that inhibit the expression of VEGF post-transcriptionally have been identified, and methods for their use provided.

In one aspect of the invention, compounds of Formula (I) are provided which are useful in the inhibition of VEGF production, in the inhibition of angiogenesis, and/or in the treatment of cancer, diabetic retinopathy or exudative macular degeneration.

In another aspect of the invention, methods are provided for the inhibition of VEGF production, the inhibition of angiogenesis, and/or the treatment of cancer, diabetic retinopathy, rheumatoid arthritis, psoriasis, atherosclerosis, chronic inflammation, other chronic inflammation-related diseases and disorders, obesity, or exudative macular degeneration using the compounds described herein.

In one embodiment, the invention is directed to methods for inhibiting VEGF production comprising administering a VEGF-expression inhibiting amount of at least one compound of the invention to a subject in need thereof.

In another embodiment, methods for inhibiting angiogenesis are provided comprising administering an anti-angiogenic amount of at least one compound of the invention to a subject in need thereof.

In yet another embodiment, methods for the treatment of cancer, diabetic retinopathy, rheumatoid arthritis, psoriasis, atherosclerosis, chronic inflammation, other chronic inflammation-related diseases and disorders, obesity, or exudative macular degeneration are provided comprising administering a therapeutically effective amount of at least one compound of the invention to a subject in need thereof.

These and other aspects of the invention will be more clearly understood with reference to the following preferred embodiments and detailed description.

DETAILED DESCRIPTION OF THE INVENTION

Figure 1:
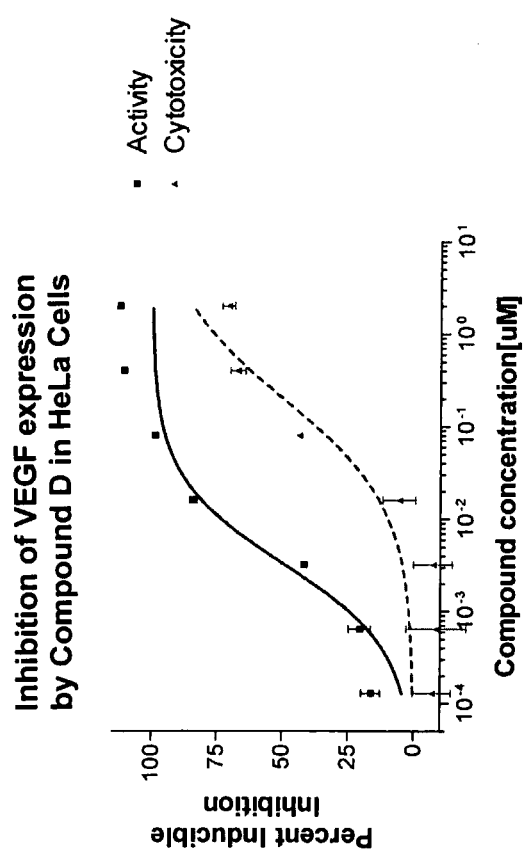
FIG. 1 illustrates inhibition of VEGF expression by a certain compound of the invention.

Aberrant up-regulation of Vascular Endothelial Growth Factor (VEGF), a key factor for angiogenesis, is an important contributor to the pathogenesis of disease states such as cancer, diabetic retinopathy, rheumatoid arthritis, psoriasis, atherosclerosis, chronic inflammation, other chronic inflammation-related diseases and disorders, obesity, or exudative macular degeneration. In accordance with the present invention, compounds that inhibit the expression of VEGF post-transcriptionally have been identified, and methods for their use provided. The compounds of the invention have nanomolar to sub-nanomolar activity for the inhibition of VEGF expression.

A. Compounds of the Invention

In one aspect of the invention, compounds are provided which are useful in the inhibition of VEGF production, in the inhibition of angiogenesis, and/or in the treatment of cancer, diabetic retinopathy or exudative macular degeneration. In certain embodiments, the compounds of the invention specifically inhibit VEGF production, while in other embodiments, the compounds of the invention inhibit VEGF expression as well as that of other angiogenesis factors such as FGF-2. In this regard, pan-angiogenic inhibitor may be preferred in methods of inhibiting tumor growth, while VEGF specific inhibitors may be preferred for the treatment of ocular neovascular disorders (Eyetech Study Group, 22(2):143-52 (2002)).

The compounds of the invention are generally chiral and as such may exist as racemic mixtures or as enantiomerically pure compositions. For example, the compounds may exist as (R,R), (R,S), (S,R) or (S,S) isomers in enantiomerically pure compositions. In a preferred embodiment, the compounds of the invention are the 10R, 3aR; the 10R, 3aS; the 10S, 3aR; or the 10S, 3aS1 isomers, and more preferably the 10S, 3aR isomer.

As used herein, "enantiomerically pure" refers to compositions consisting substantially of a single isomer, preferably consisting of 90%, 92%, 95%, 98%, 99%, or 100% of a single isomer.

Preferred compounds of the present invention useful in the inhibition of VEGF production include those of Formula (I) as shown below.

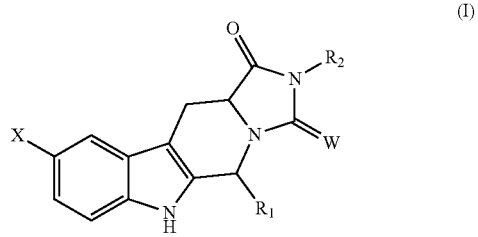

(I)

wherein,

X is hydrogen, a hydroxyl group, a halogen, a $C_1$ to $C_6$ alkyl group, or a $C_1$ to $C_5$ alkoxy, optionally substituted with a $C_6$ to $C_{10}$ aryl group;

W is an oxygen or sulfur atom;

$R_1$ is a $C_1$ to $C_8$ alkyl group; a heteroaryl group; or a $C_6$ to $C_{10}$ aryl group, optionally substituted with one or more independently selected $R_0$ groups;

$R_0$ is a halogen; a $C_1$ to $C_6$ alkyl, wherein the alkyl group is optionally substituted with one or more independently selected halogen groups; a 5 to 12 membered heterocycle, wherein the heterocycle is optionally substituted with a $C_1$ to $C_6$ alkyl group; a 5 to 12 membered heteroaryl group; a cyano group; a nitro group; an amino group, wherein the amino group is optionally substituted with one or more a $C_1$ to $C_6$ alkyl groups; an amid group; an ester group; or —$OR_a$ group;

$R_a$ is hydrogen; or a $C_1$ to $C_6$ alkyl, wherein the alkyl group is optionally substituted with one or more independently selected halogen, $C_1$ to $C_4$ alkoxy, 5 to 10 membered heteroaryl, 5 to 10 membered heterocycle, or amino groups; wherein the heterocycle is optionally substituted with a —C(O)—$R_c$ group or a $C_1$ to $C_6$ alkyl optionally substituted with a hydroxyl group; and the amino group is optionally substituted with one or more independently selected $C_1$ to $C_6$ alkyl groups optionally substituted with a $C_1$ to $C_4$ alkoxy group;

$R_2$ is a 5 to 12 membered heteroaryl group; $C_2$ to $C_8$ alkenyl group; a $C_1$ to $C_8$ alkyl group, wherein the alkyl group optionally substituted with one or more independently selected halogen, $C_1$ to $C_4$ alkoxy, 5 to 10 membered heterocycle, 5 to 10 membered heteroaryl, $C_6$ to $C_8$ aryl optionally substituted with one or more independently selected $R_b$ or —C(O)—O—$R_c$ groups; or a $C_6$ to $C_{10}$ aryl group, optionally substituted with one or more independently selected $R_b$ groups;

$R_b$ is a halogen; cyano; nitro; a $C_1$ to $C_4$ alkoxy; a $C_1$ to $C_6$ alkyl, wherein the alkyl is optionally substituted with one or more halogen groups; —O—C(O)—$R_c$; or a —C(O)—O—$R_c$ group; and $R_c$ is a hydroxyl or $C_1$ to $C_6$ alkyl group.

As will be evident to one of skill in the art, the compounds of Formula (I) comprise at least two stereocenters (e.g., at the $R_1$ substituent), and may exist as a racemic mixture or as an enantiomerically pure composition. As discussed above, in a preferred embodiment, the compounds of Formula (I) in an enantiomerically pure composition. More particularly, in a preferred embodiment, the compounds of the invention are the 5R, 11aR; the 5R, 11aS; the 5S, 11aR; or the 5S, 11aS isomer, and more preferably the 5S, 11aR isomer. In this regard, the compounds of the invention may exist as enantiomerically pure compositions consisting essentially of the 5R, 11aR; the 5R, 11aS; the 5S, 11aR; or the 5S, 11aS isomer, and more preferably the 5S, 11aR isomer.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be include $C_1$ to $C_8$, $C_1$ to $C_6$, or $C_1$ to $C_4$ alkyl groups. The alkyl group may be optionally substituted with one or more halogen or alkoxy groups. For instance, the alkyl group may be a haloalkyl, dihaloalkyl, or trihaloalkyl.

As used herein, "alkenyl" generally refers to linear, branched or cyclic alkene radicals having one or more carbon-carbon double bonds, such as $C_2$ to $C_8$ and $C_2$ to $C_6$ alkenyl groups, including 3-propenyl.

As used herein, "alkynyl" generally refers to linear, branched or cyclic alkyne radicals having one or more carbon-carbon triple bonds, such as $C_2$ to $C_8$ and $C_2$ to $C_6$ alkynyl groups, including hex-3-yne.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain one or more heteroatoms, two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, dihydro-chromen-4-only, 1,3-diazine, 1,2-diazine, 1,2-diazole, 1,4-diazanaphthalene, furan, furazan, imidazole, indole, isoxazole, isoquinoline, isothiazole, isoindolyl, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline. In certain embodiments, the heteroaryl may be optionally substituted.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. In some embodiments, the heterocycle groups may be selected from heterocycle groups that contain one or more heteroatoms, two or more heteroatoms, three or more heteroatoms, or four or more heteroatoms. Example of heterocycle groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkanoyl" generally refers to a group with the structure —C(O)—R. In certain embodiments, R may be hydrogen, alkyl, a 4-morpholinyl group, or a thiazoleamino group.

As used herein, "alkoxy" generally refers to a group with the structure —O—R. In certain embodiments, R may be an alkyl group, such as a $C_1$ to $C_5$ alkyl group.

For the purposes of this invention, halo substituents may be independently selected from the halogens such as fluorine, chlorine, bromine, iodine, and astatine.

In certain preferred embodiments, X may be hydrogen, methyl, methoxy or a halogen, preferably methyl or a halogen, and more preferably methyl, bromide or chloride.

$R_1$ may preferably be a $C_6$ to $C_8$ aryl group, optionally substituted with at least one $R_0$ group. $R_0$ may then preferably be hydroxyl, a $C_1$ to $C_6$ alkyl, an alkoxy, or a halogen, more preferably methoxy, propyl, or a halogen, and more preferably methoxy, chloride, or fluoride. Alternatively, $R_0$ may preferably be —$OR_a$, wherein $R_a$ a $C_1$ to $C_6$ alkyl, optionally substituted with a heterocycle group, more preferably $R_a$ is methyl or ethyl-piperidine. Alternatively, $R_1$ may be a benzodioxole group.

$R_2$ may preferably be a $C_3$ to $C_6$ cycloalkyl group. In another embodiment, $R_2$ is preferably a heteroaryl, more preferably a pyridine group. Alternatively, $R_2$ may preferably be a $C_6$ to $C_8$ aryl group, optionally substituted with at least one $R_b$ group. Preferred $R_b$ groups are fluoride, methyl, iso-butyl and methoxy.

Preferred $R_1$ substituents include the following, where the * indicates the bond of attachment to the scaffold molecule.

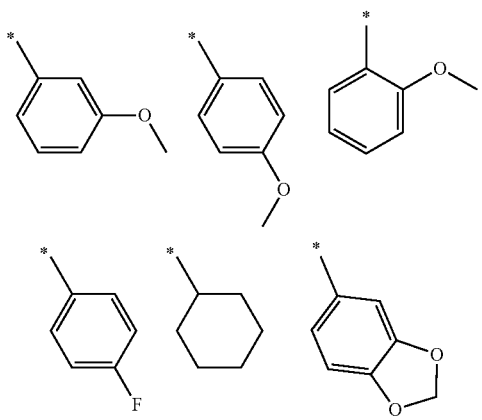

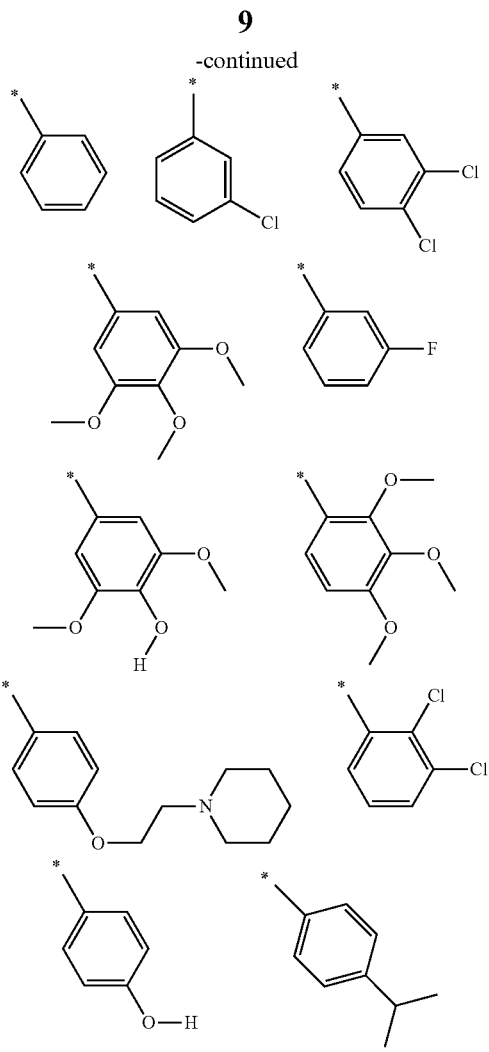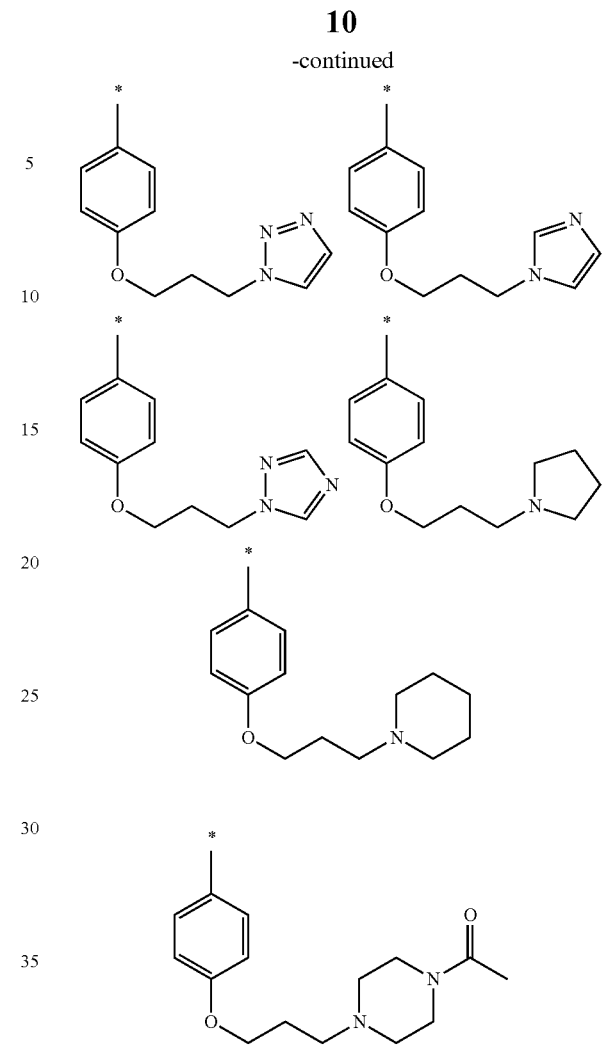
Other preferred R$_1$ substituents include the following, where the * indicates the bond of attachment to the scaffold molecule.
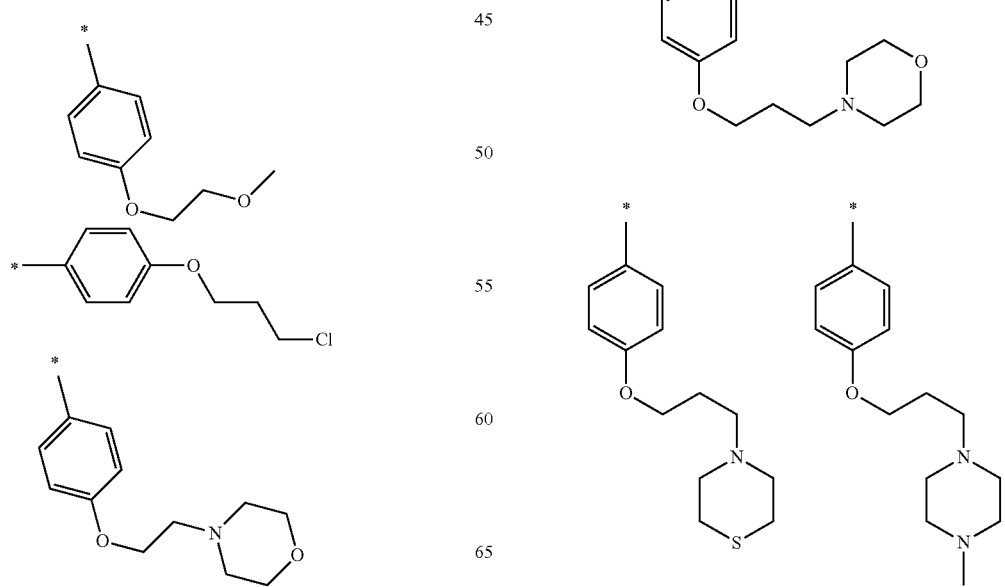

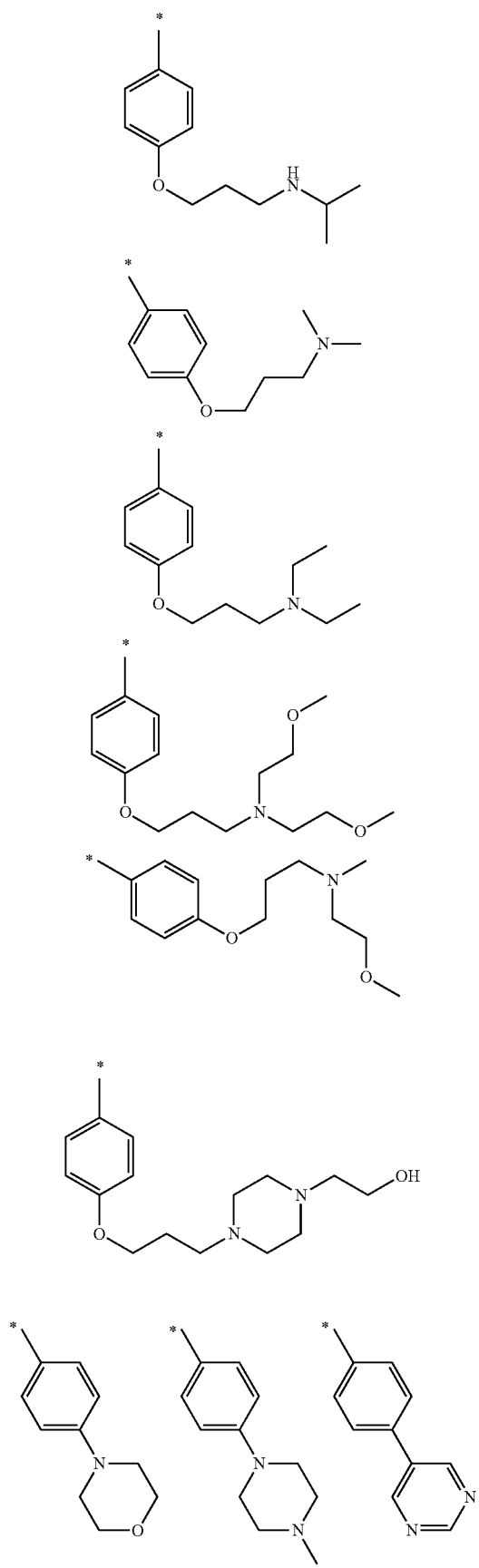
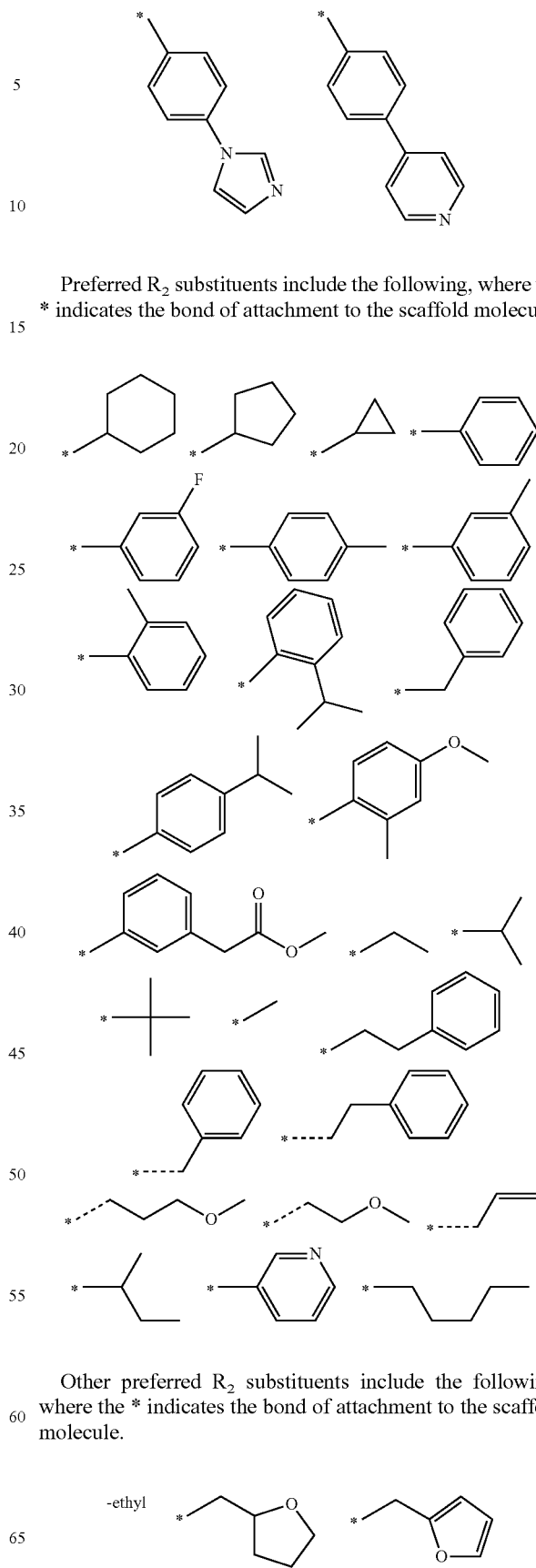
Preferred R₂ substituents include the following, where the * indicates the bond of attachment to the scaffold molecule.
Other preferred R₂ substituents include the following, where the * indicates the bond of attachment to the scaffold molecule.
-ethyl -continued

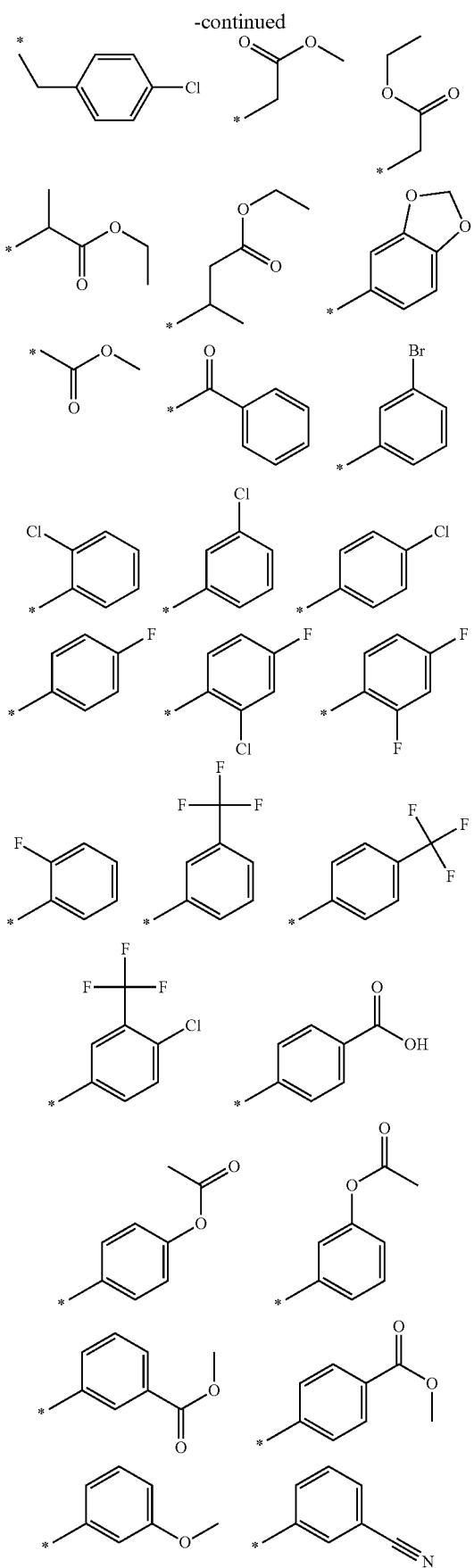

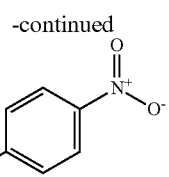

A preferred class of compounds within Formula (I) include those compounds of Formula (I-a) as shown below.

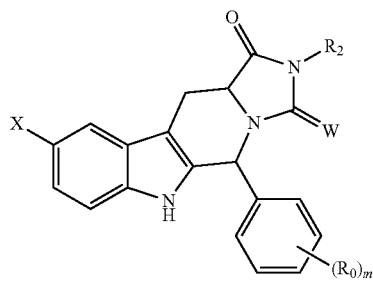

(I-a)

wherein:
X, W, $R_2$, $R_0$ is as described above with regard to Formula (I), including preferred embodiments; and
m is 0, 1, 2, or 3.

Another preferred class of compounds within the scope of the invention include the compounds of Formula (I-b) as shown below.

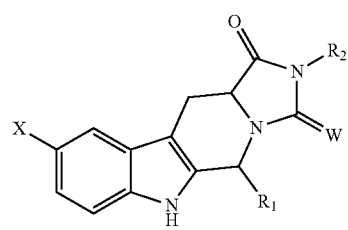

(I-b)

wherein,
X is hydrogen, a hydroxyl group, a halogen, a $C_1$ to $C_6$ alkyl group, or a $C_1$ to $C_5$ alkoxy, optionally substituted with a $C_6$ to $C_8$ aryl group;
W is an oxygen or sulfur atom;
$R_1$ is a $C_1$ to $C_8$ alkyl group; a heteroaryl group; or a $C_6$ to $C_8$ aryl group, optionally substituted with at least one $R_0$ group;
$R_0$ is a halogen; a $C_1$ to $C_6$ alkyl, optionally substituted with one or more halogen groups; or —$OR_a$; a cyano group; a nitro group; an amino group; an aminoalkyl group; an amide group; an ester group.
$R_a$ is hydrogen, a $C_1$ to $C_6$ alkyl, optionally substituted with a heterocycle group;
$R_2$ is a $C_2$ to $C_4$ alkylene group, a $C_1$ to $C_8$ alkyl group, optionally substituted with a $C_6$ to $C_8$ aryl group or an alkoxy group; a $C_6$ to $C_8$ heteroaryl group; or a $C_6$ to $C_8$ aryl group, optionally substituted with one or more $R_b$ groups;
$R_b$ is a halogen; a $C_1$ to $C_6$ alkyl group, optionally substituted with one or more halogen groups; a alkoxy group; or a —C(O)O—$R_c$ group; and
$R_c$ is a $C_1$ to $C_6$ alkyl.

Also included within the scope of the invention are pharmaceutically acceptable salts, hydrates, solvates, calthrates, polymorphs, racemates and stereoisomers of the compounds described herein.

For the purposes of this invention, where one or more functionalities encompassing X, $R_1$, $R_2$, $R_0$, $R_a$, $R_b$, $R_c$ and W, are incorporated into a molecule of Formula (I), including Formula (I-a) and (I-b), each functionality appearing at any location within the disclosed may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

Preferred compounds of the invention include the following.

1

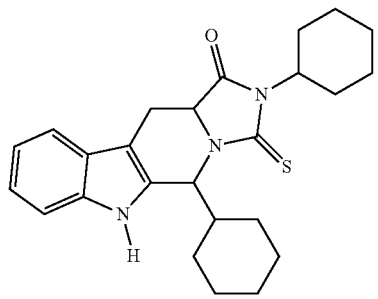

2

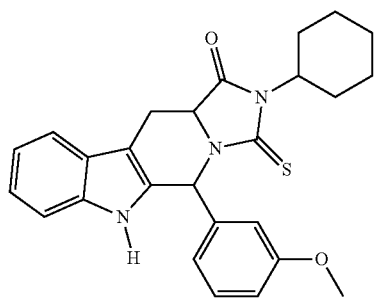

3

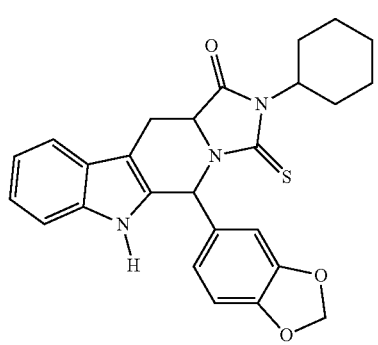

-continued

4

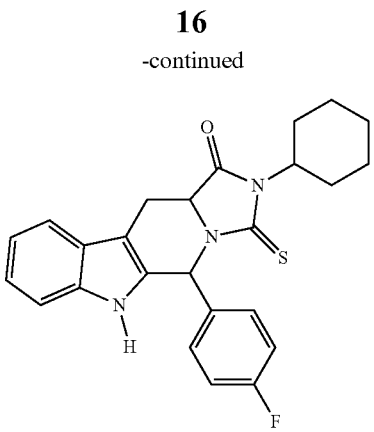

5

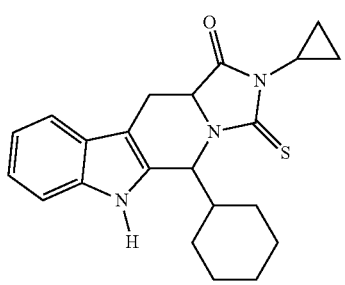

6

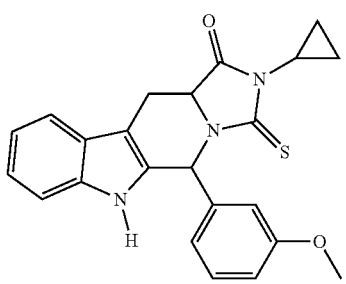

7

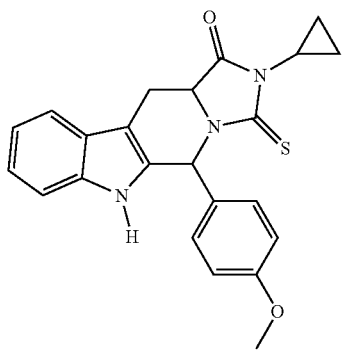

8

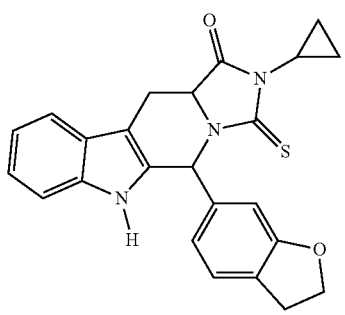

-continued
9
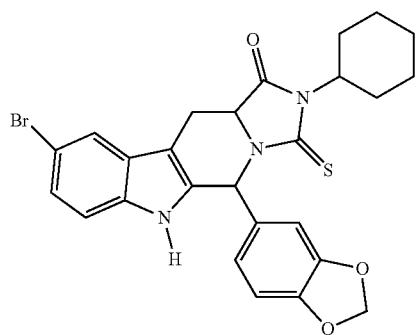
10
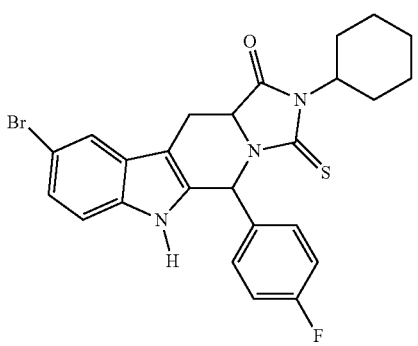
11
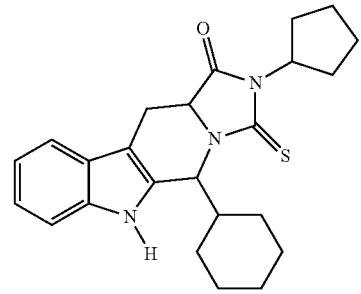
12
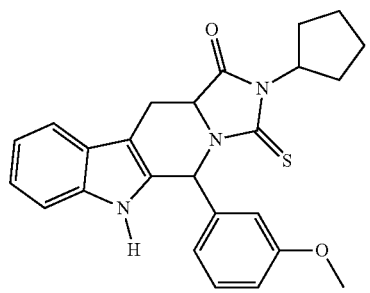
13
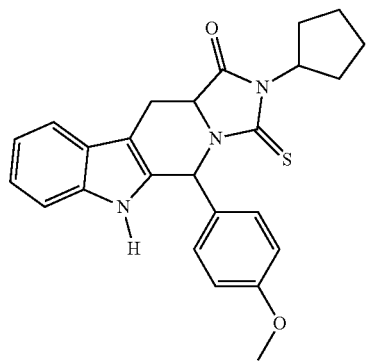
-continued
14
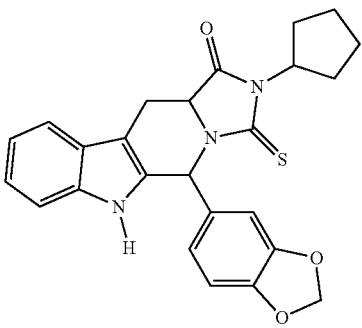
15
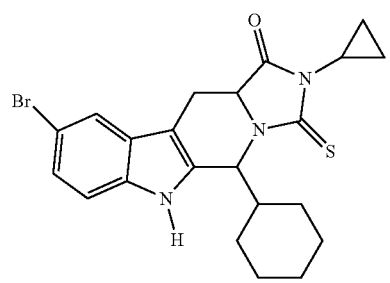
16
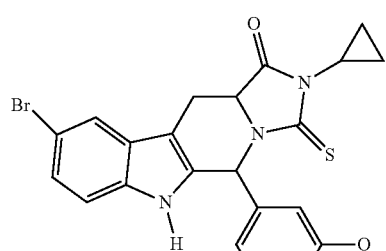
17
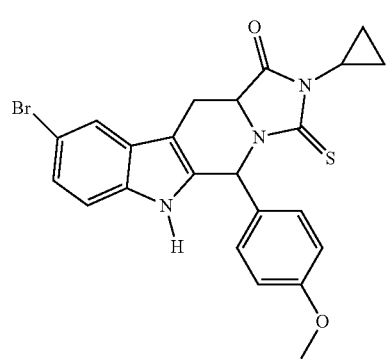
18
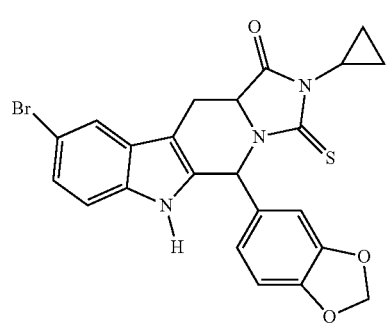

-continued
19
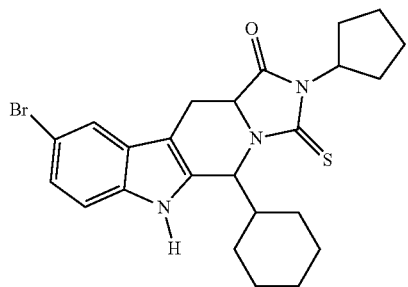
20
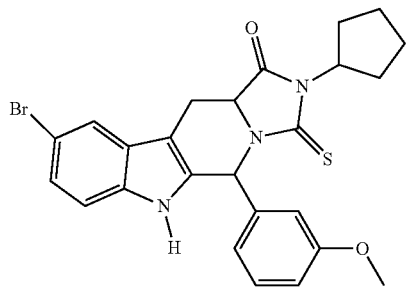
21
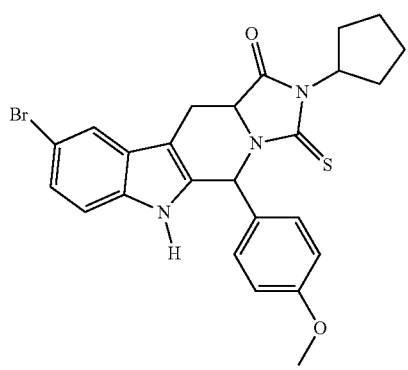
22
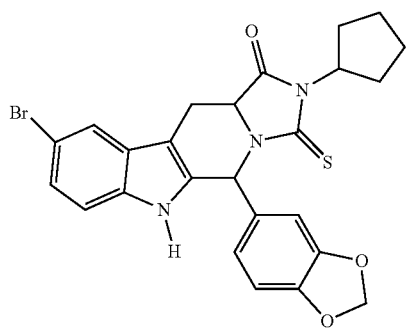
23
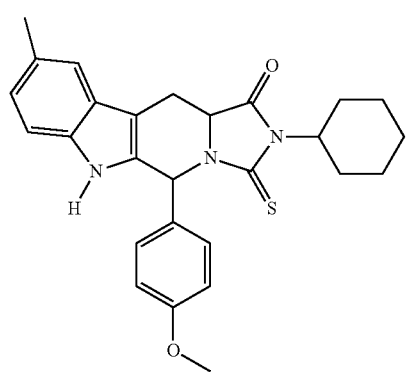
-continued
24
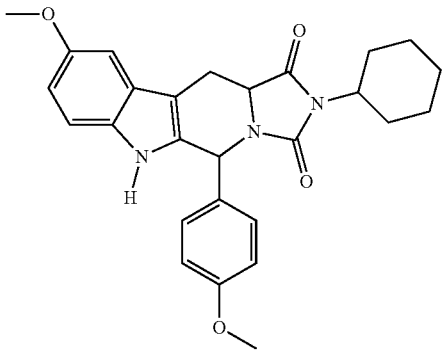
25
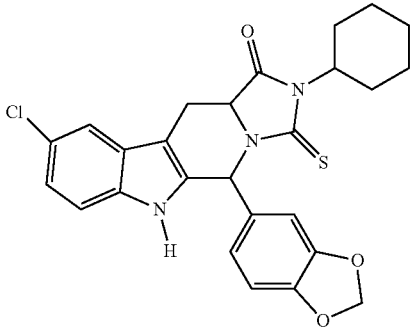
26
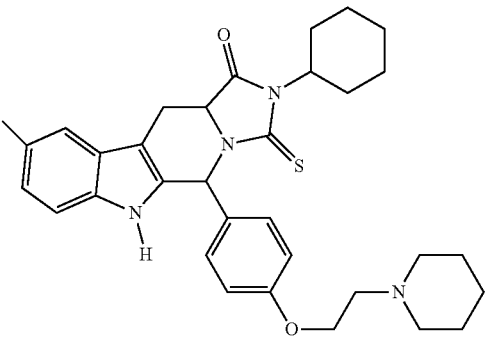
27
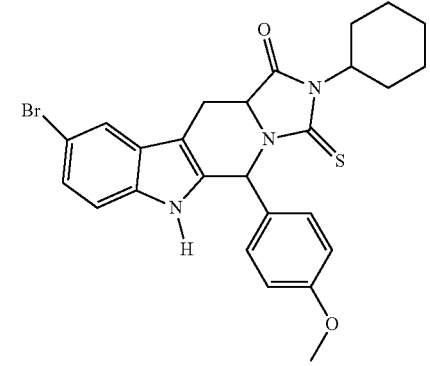

28
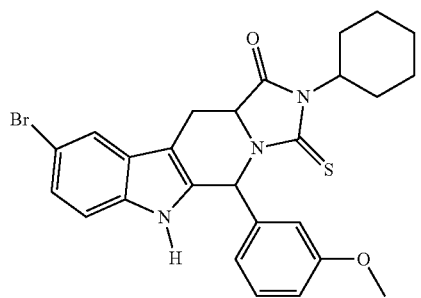
29
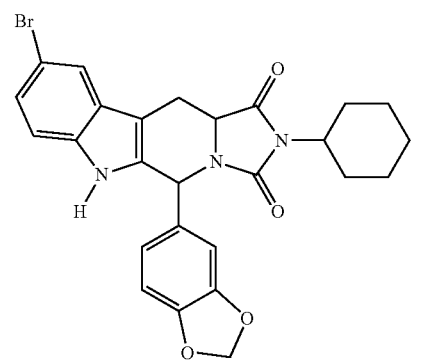
30
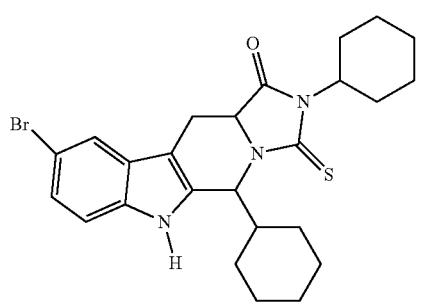
31
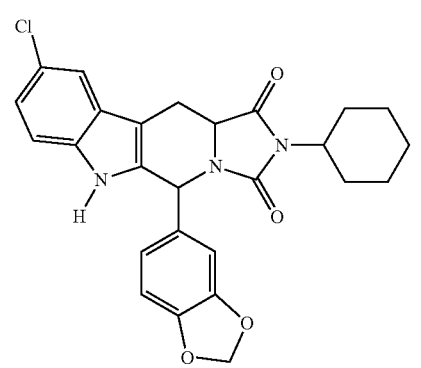
32
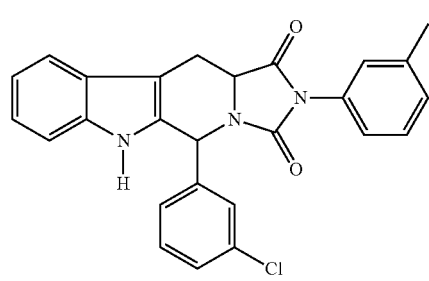
33
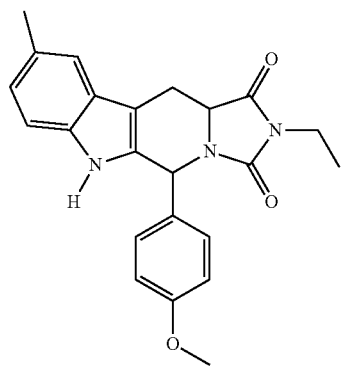
34
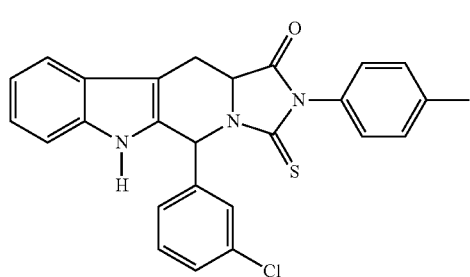
35
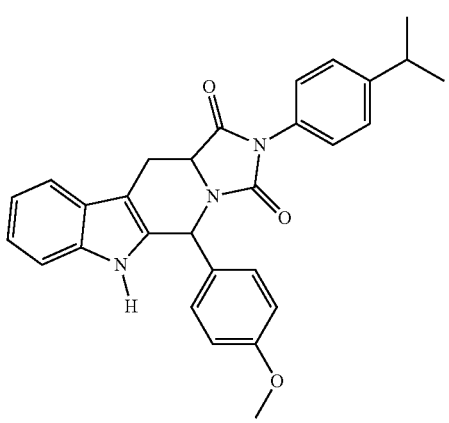
36
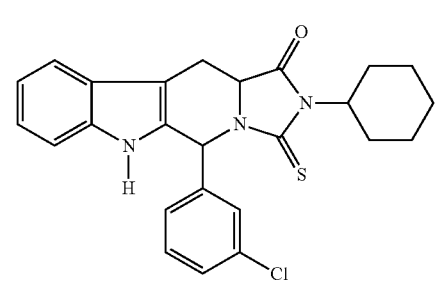
37
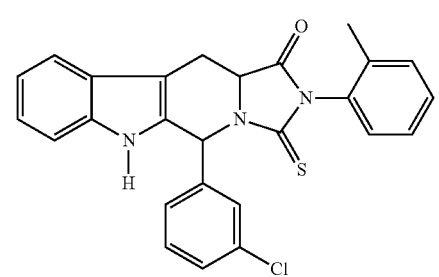

38
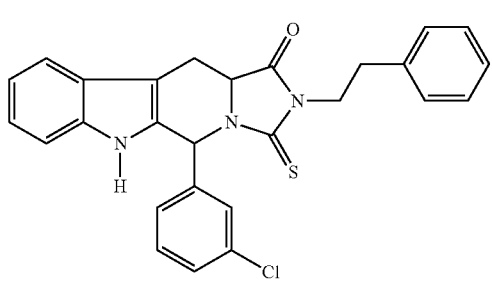
39
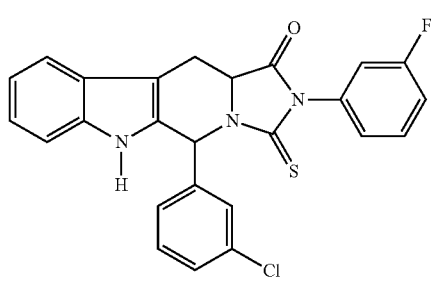
40
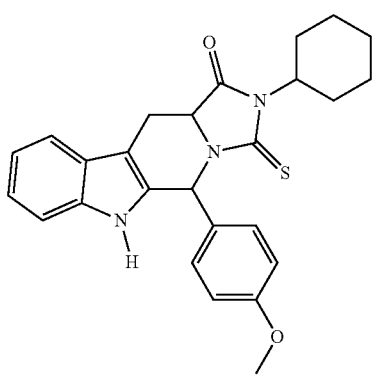
41
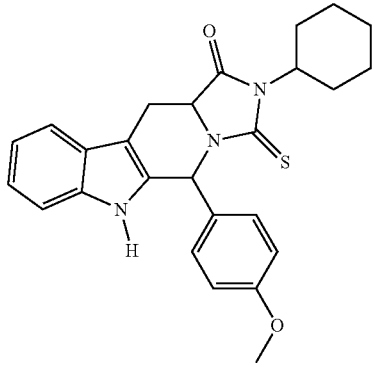
42
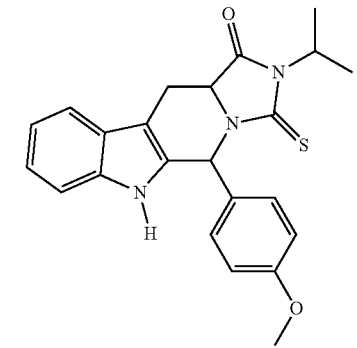
43
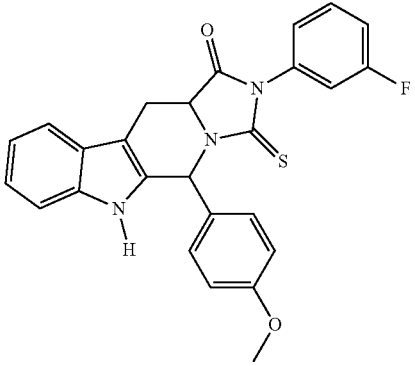
44
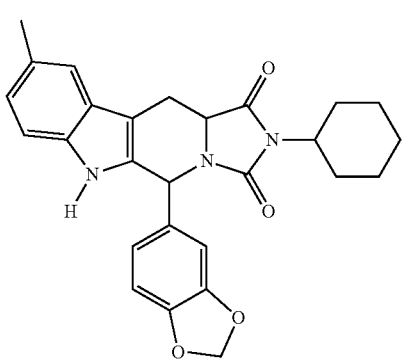
45
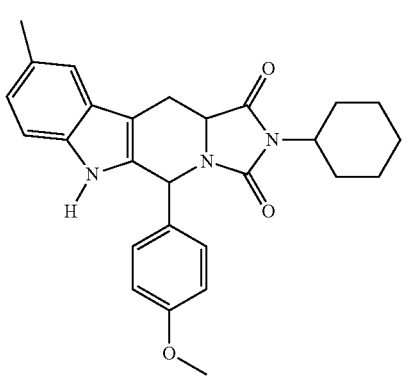
46
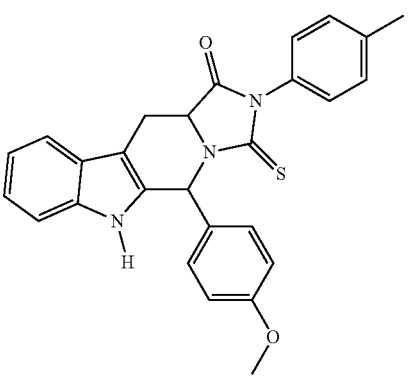

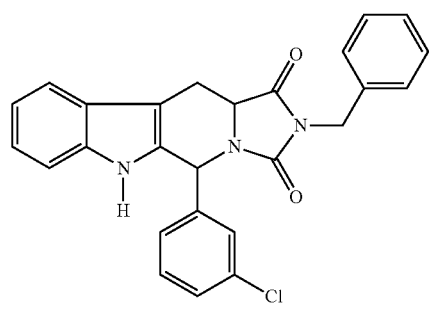
47
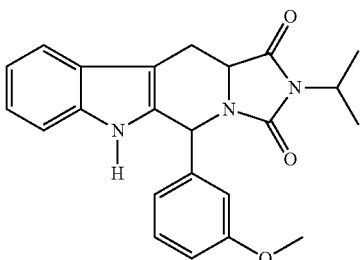
52
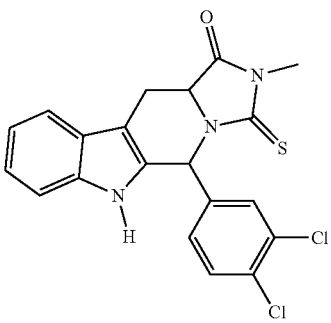
53
48
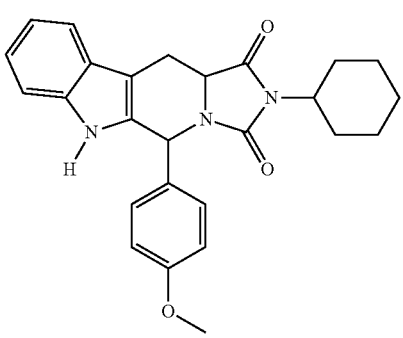
54
49
55
50
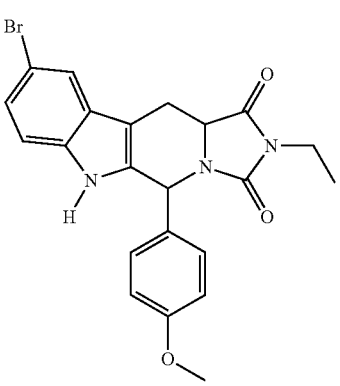
51
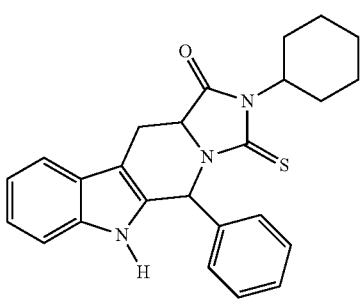
56

-continued
57
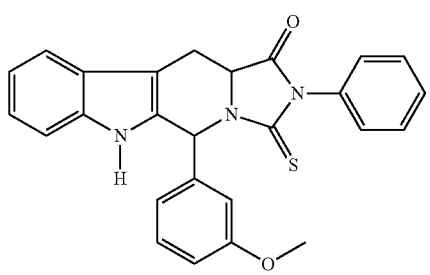
58
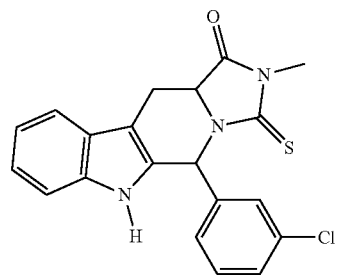
59
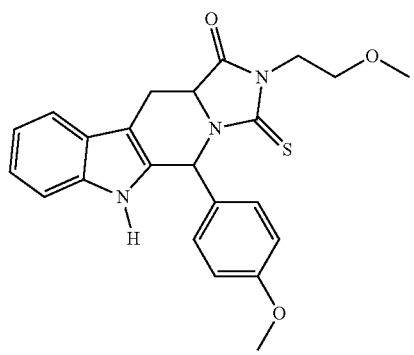
60
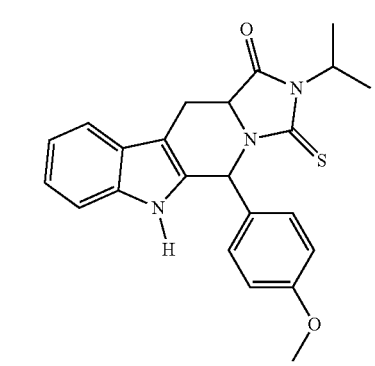
61
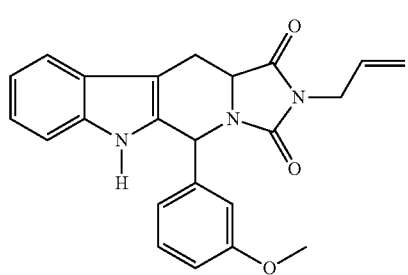
-continued
62
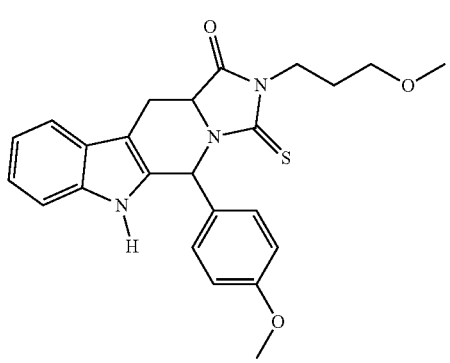
63
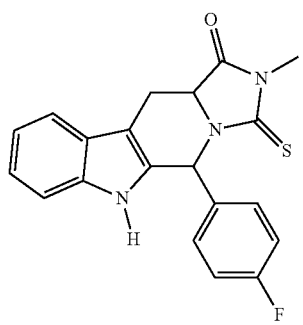
64
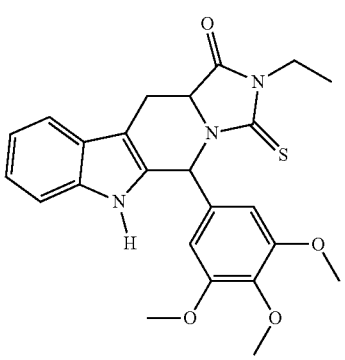
65
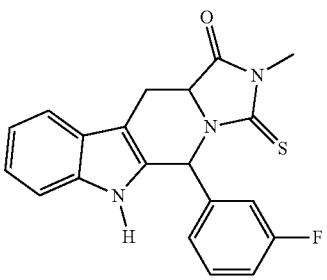

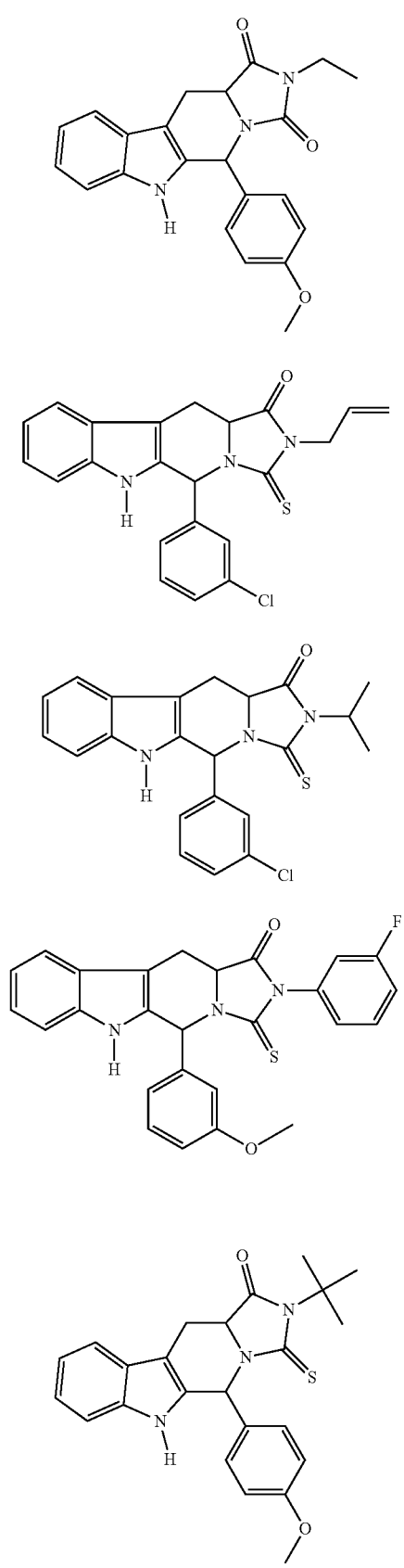
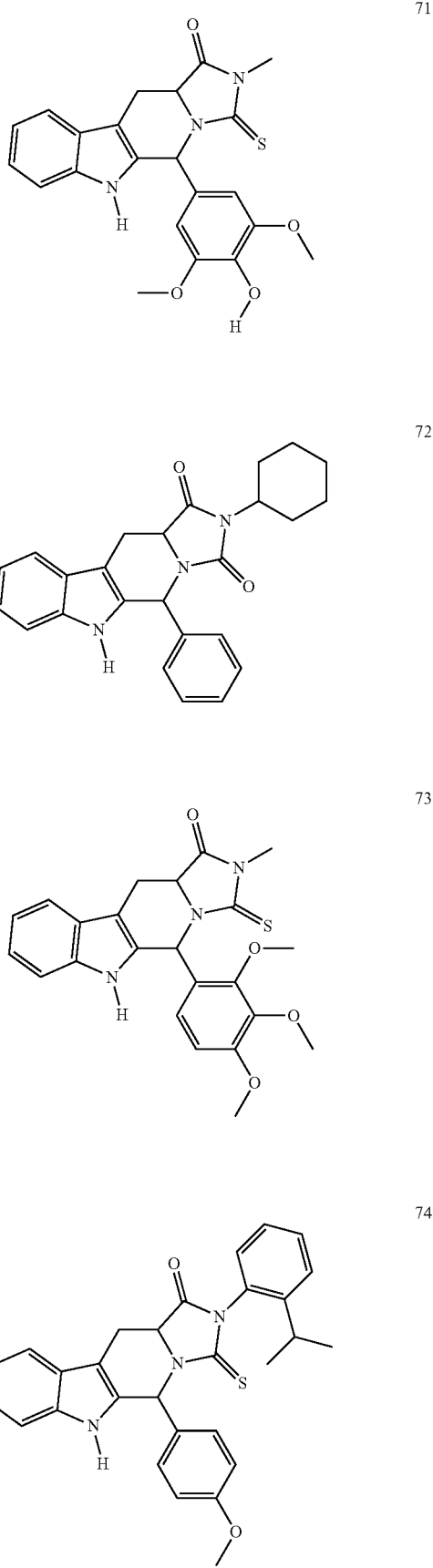

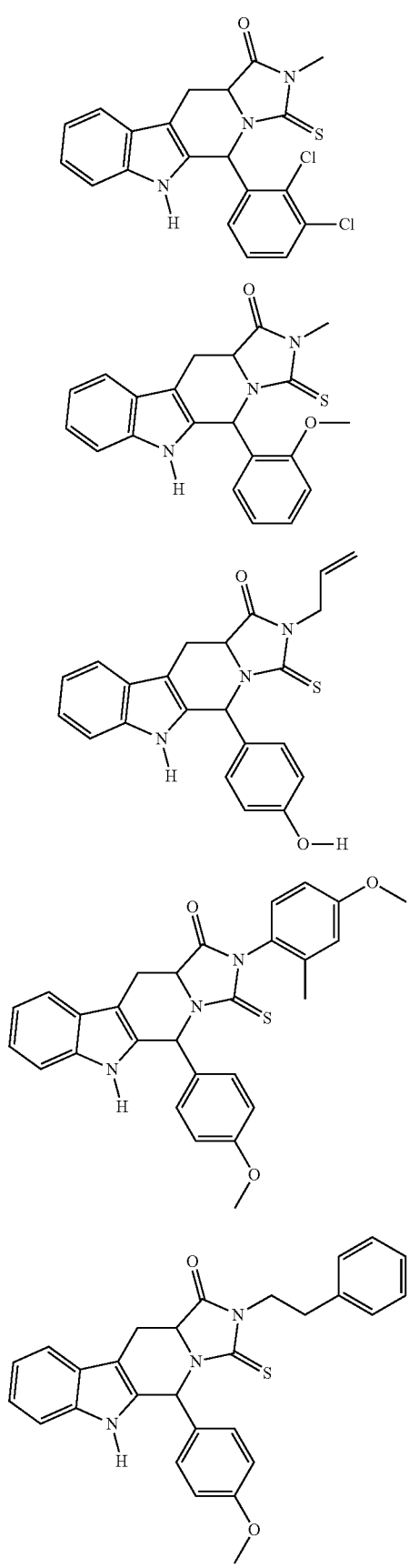
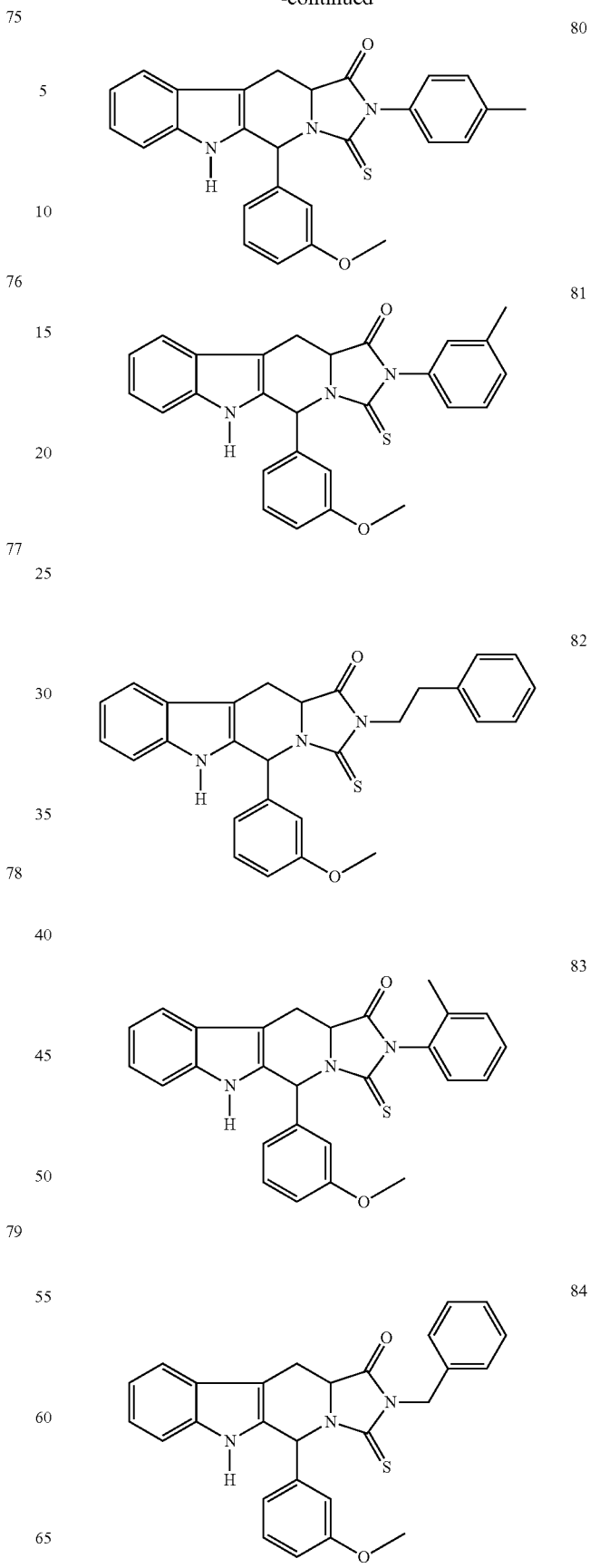

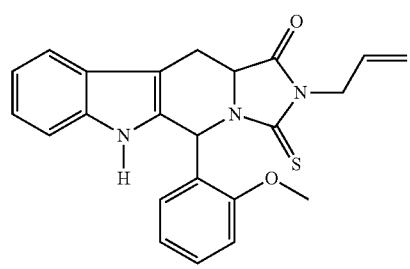
85
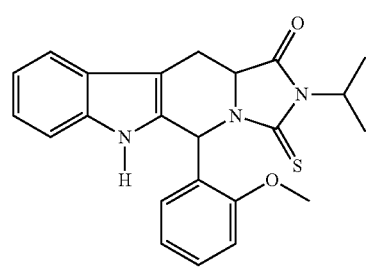
86
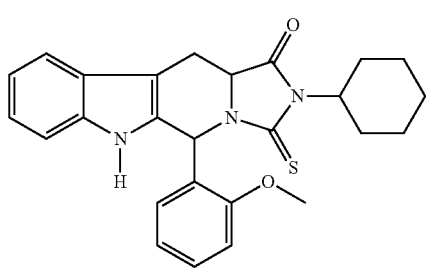
87
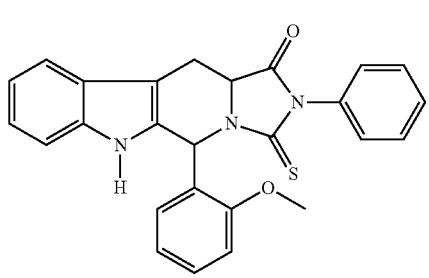
88
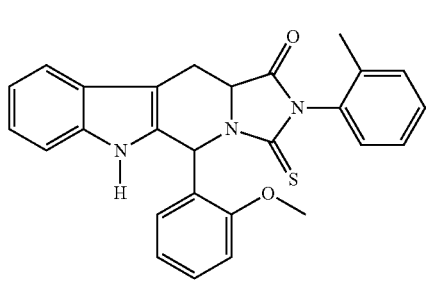
89
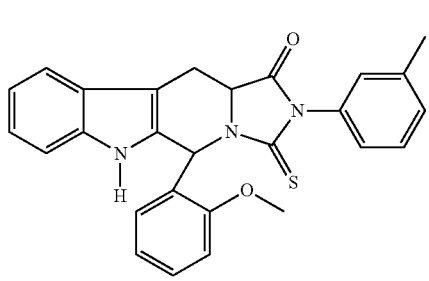
90
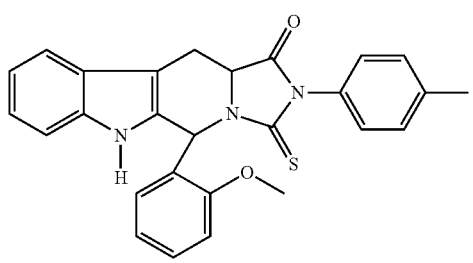
91
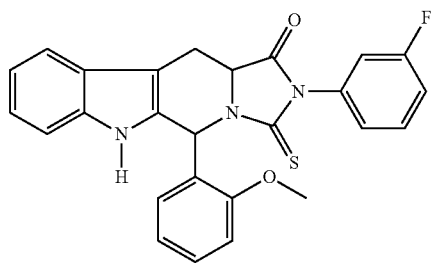
92
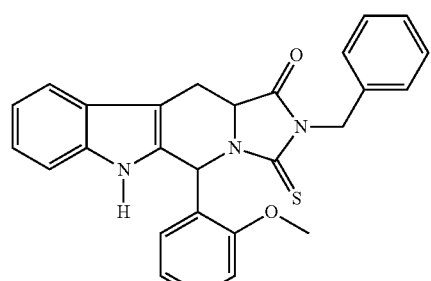
93
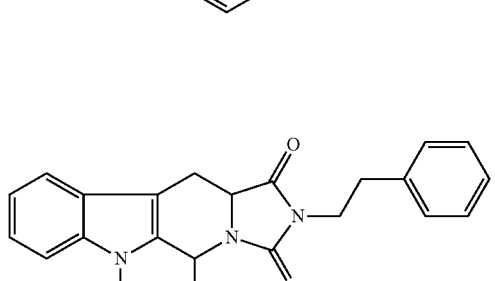
94
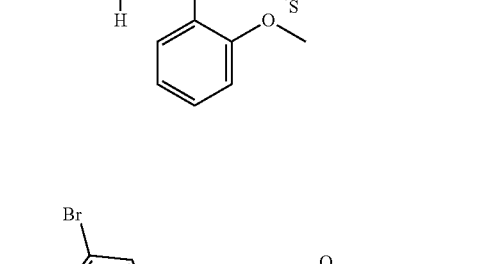
95
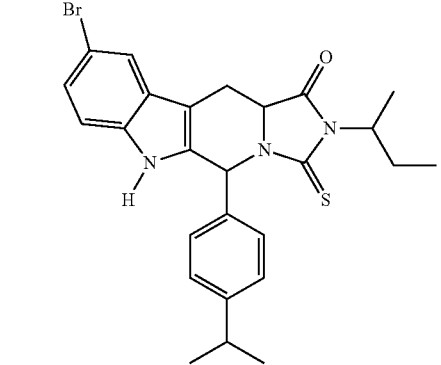

96
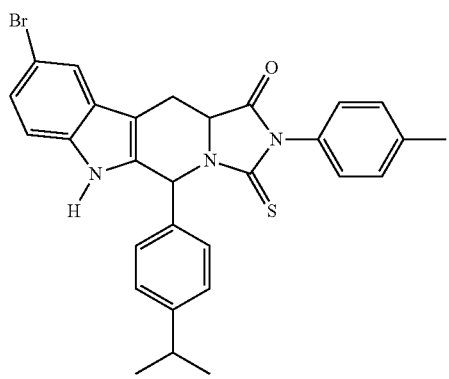
97
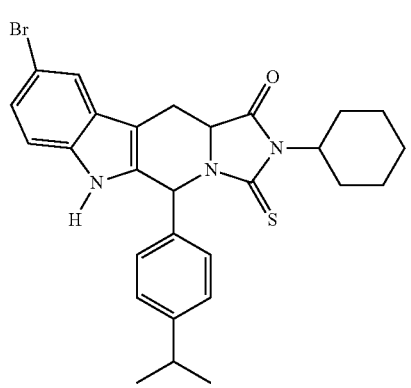
98
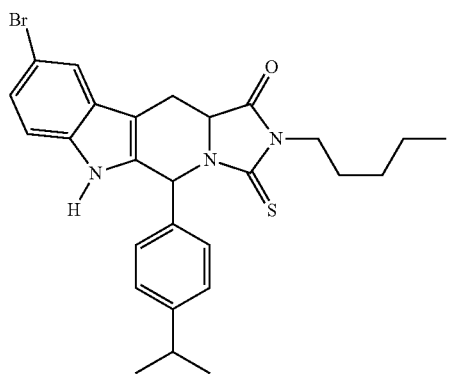
99
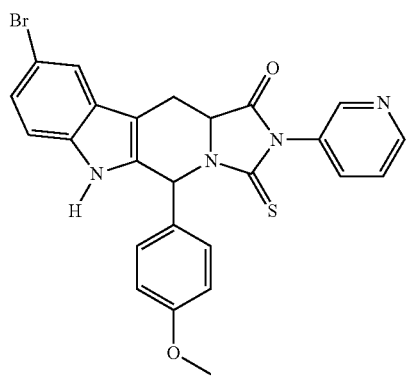
100
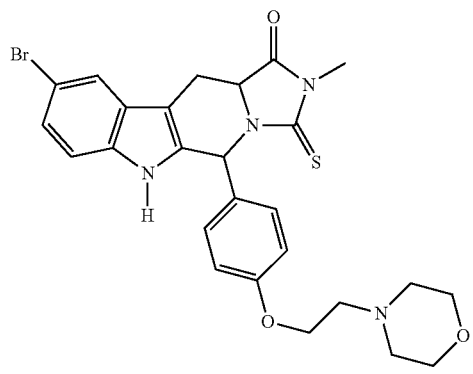
101
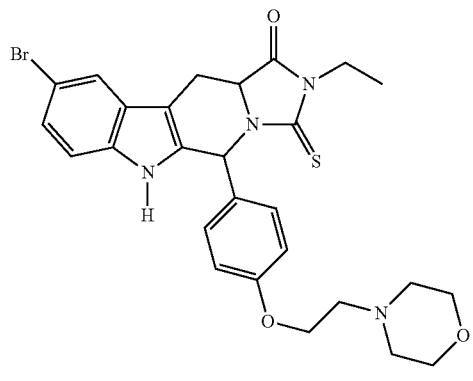
102
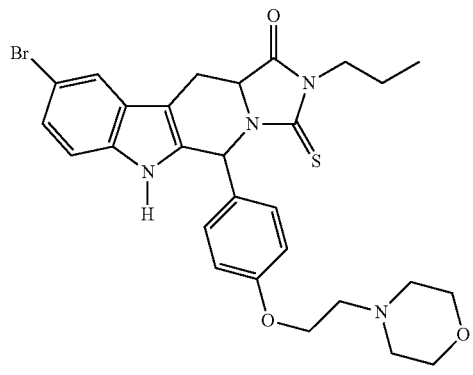
103
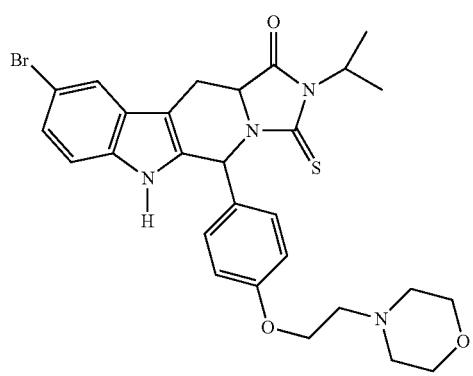

104
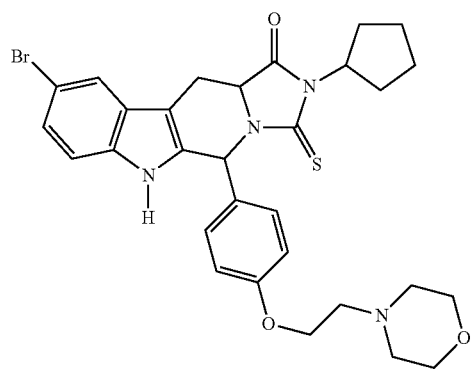
105
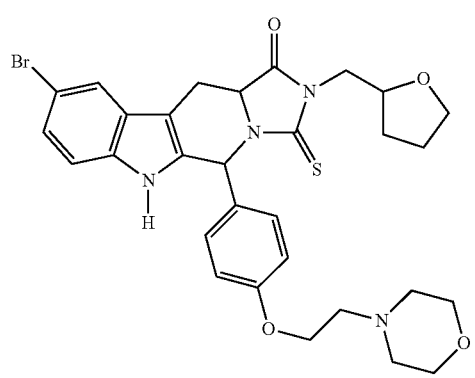
106
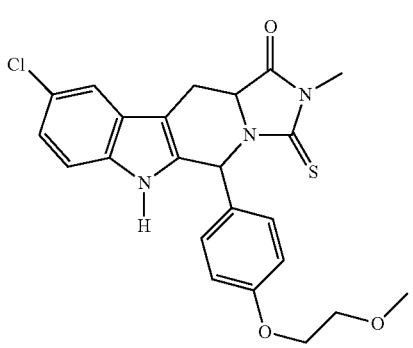
107
108
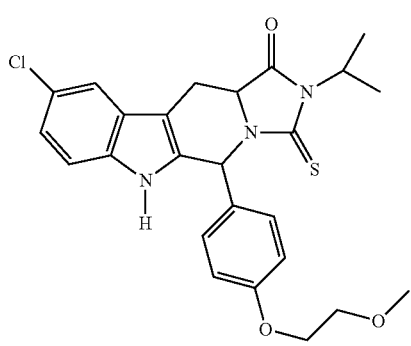
109
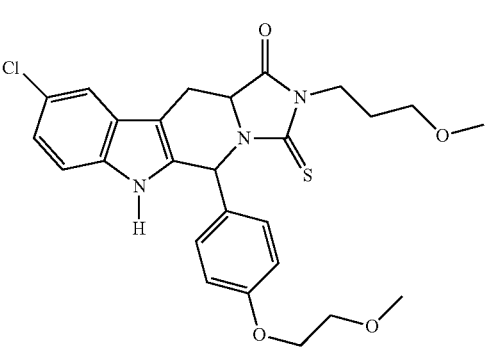
110
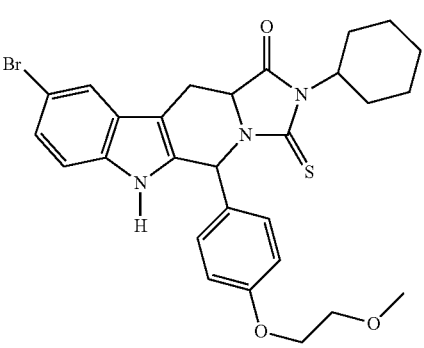
111

112
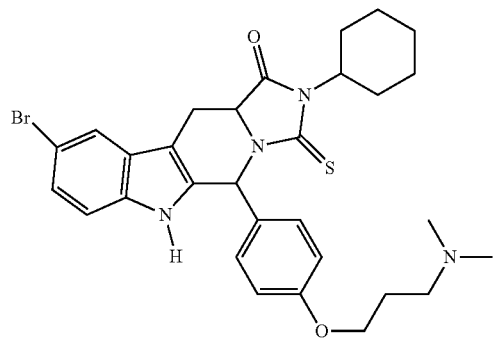
113
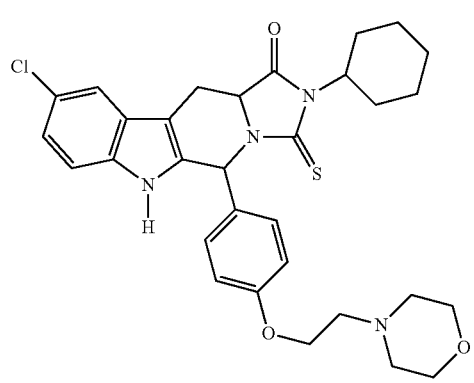
114
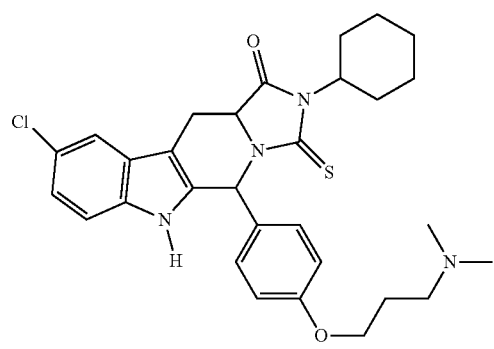
115
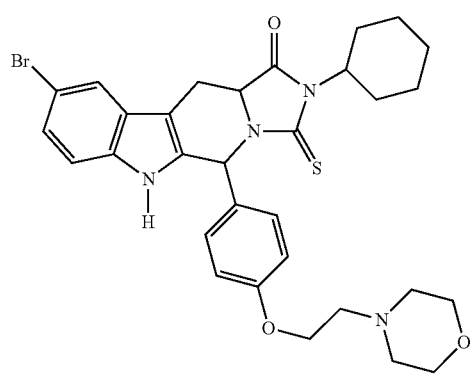
116
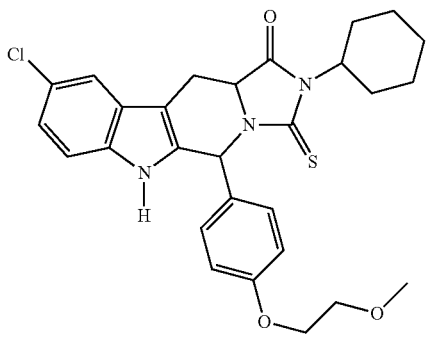
117
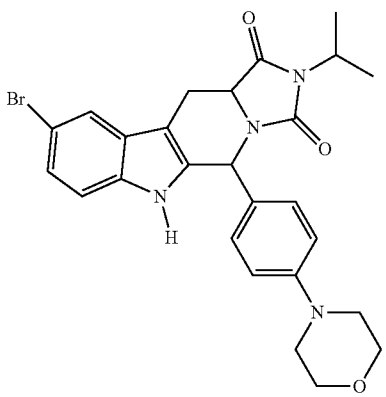
118
119
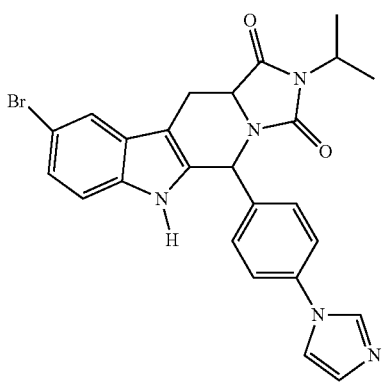

120
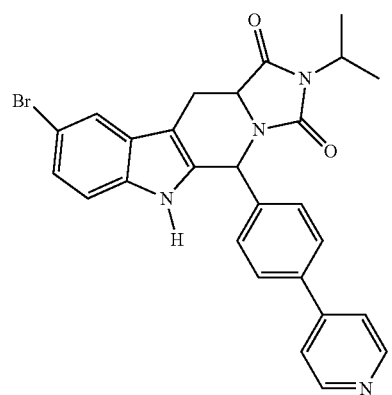
121
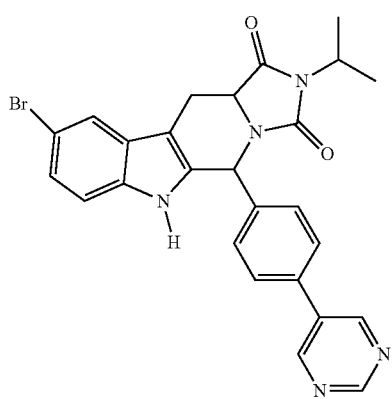
122
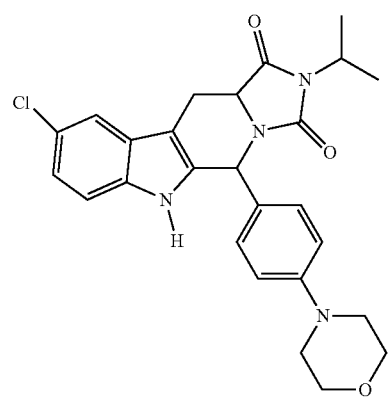
123
124
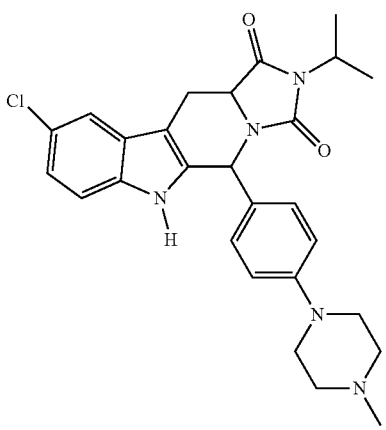
125
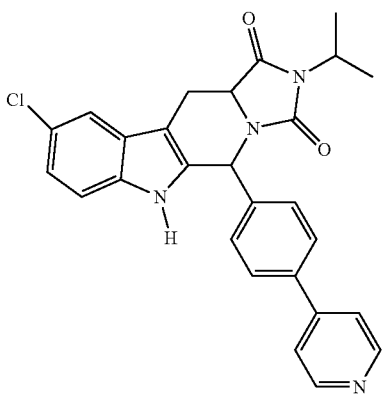
126
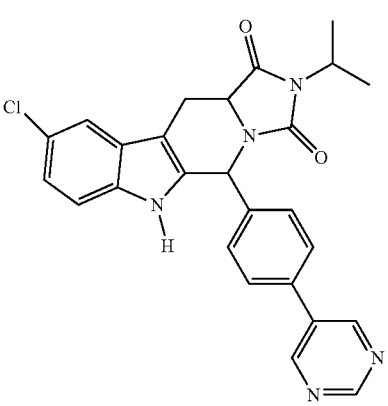
127
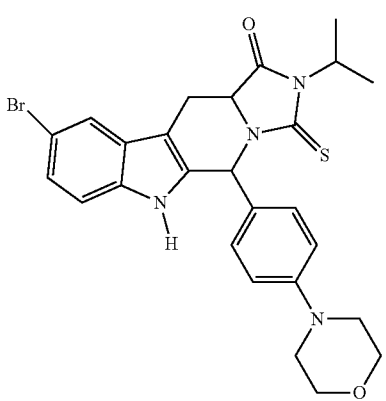

128 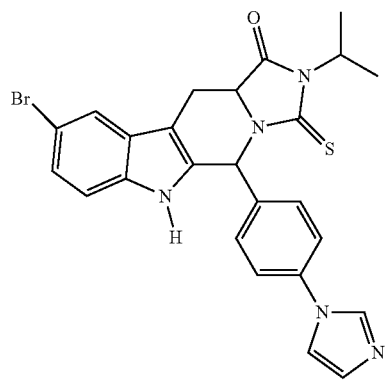
129 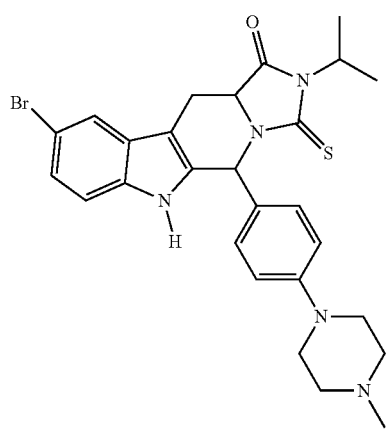
130 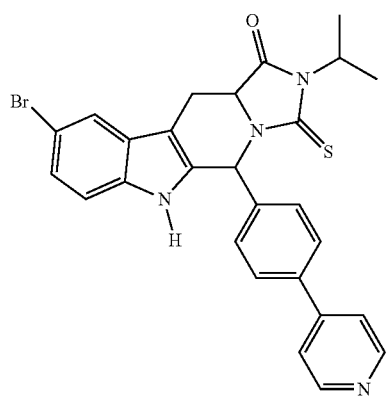
131 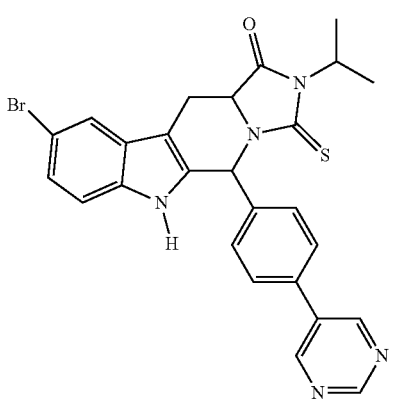
132 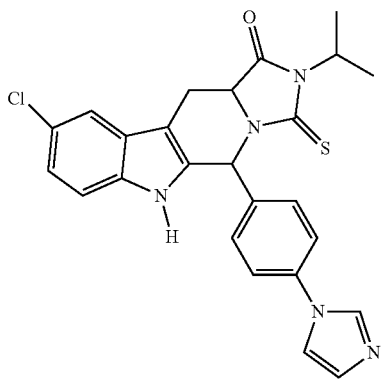
133 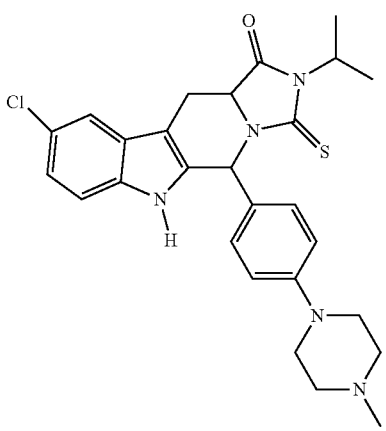
134 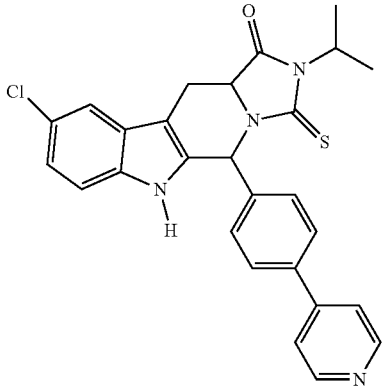
135 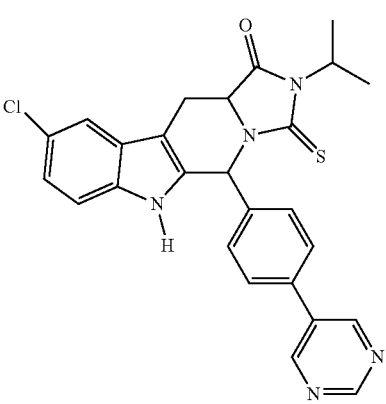

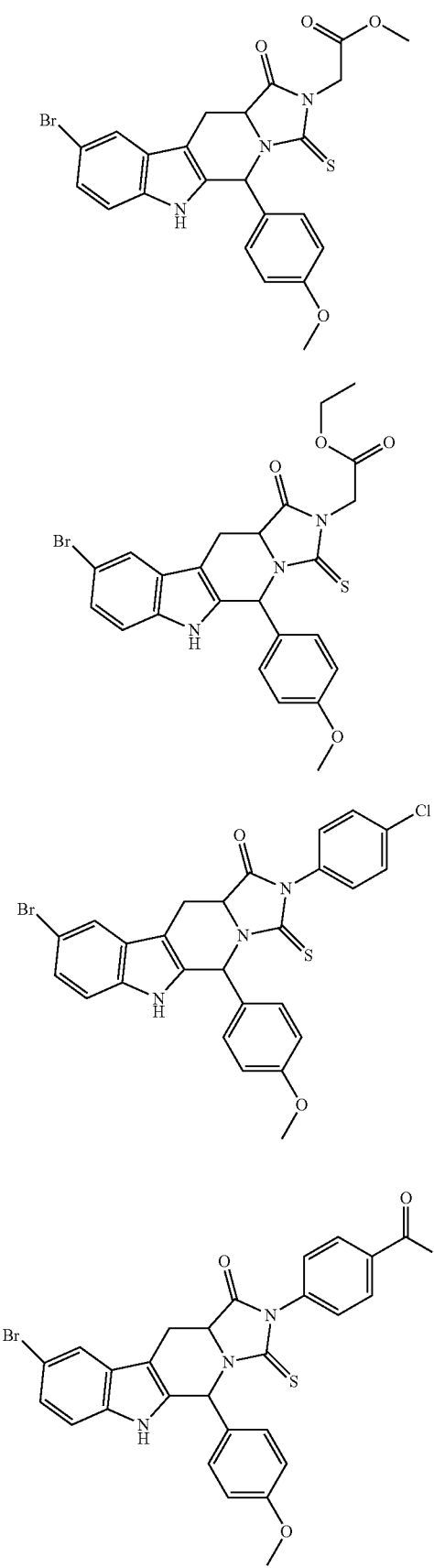
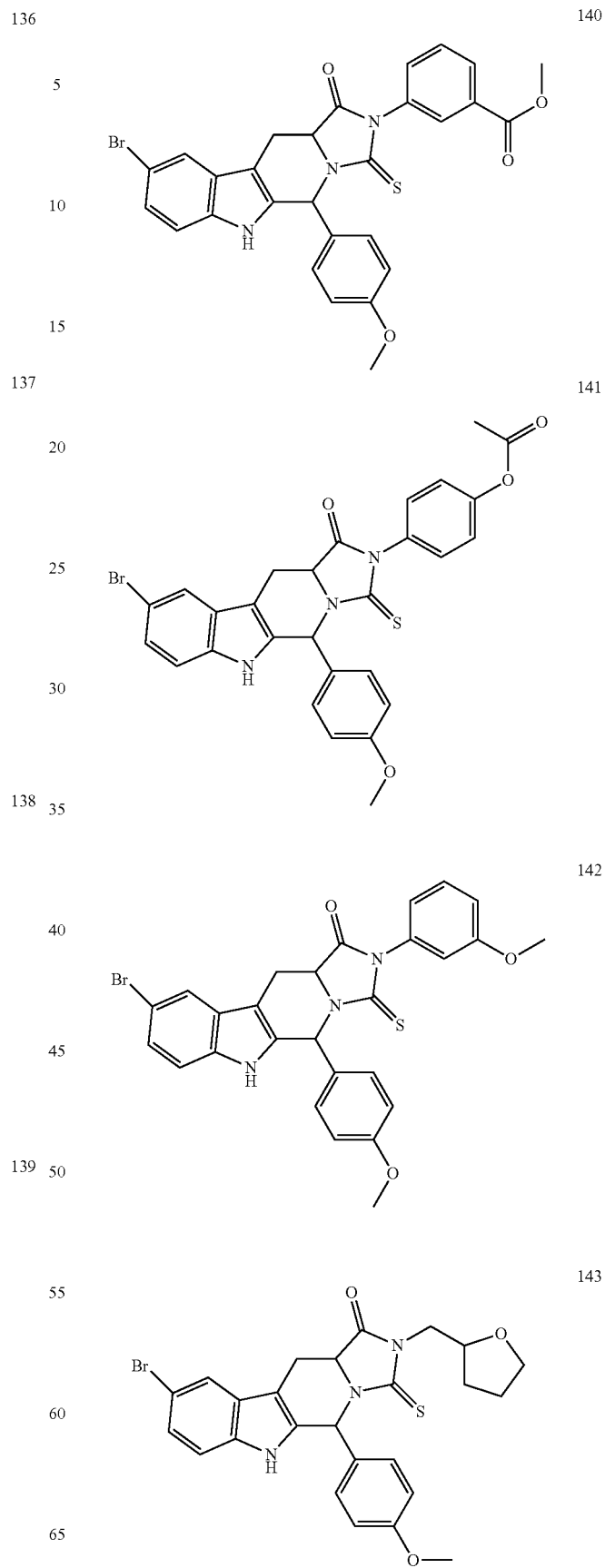

144
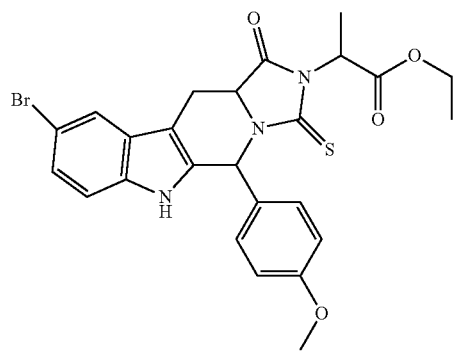
145
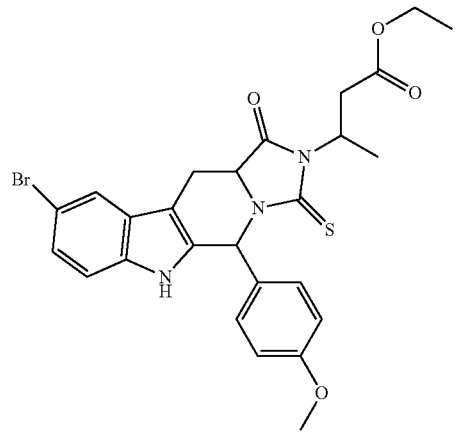
146
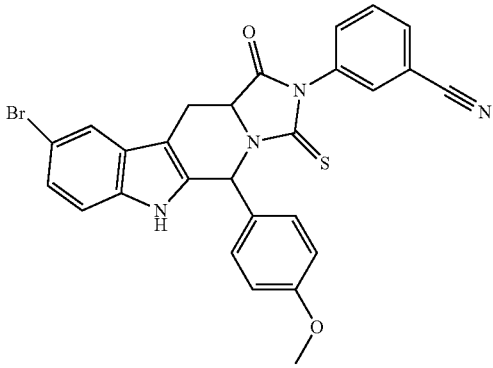
147
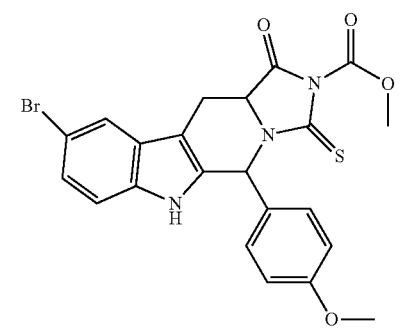
148
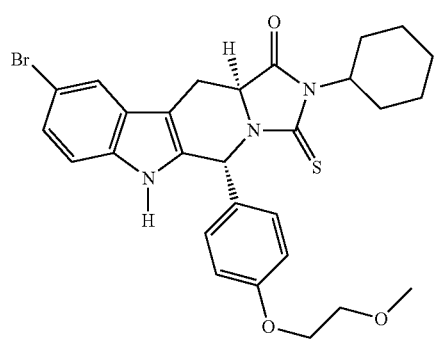
149
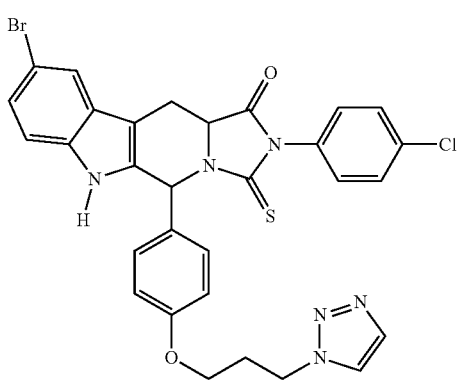
150
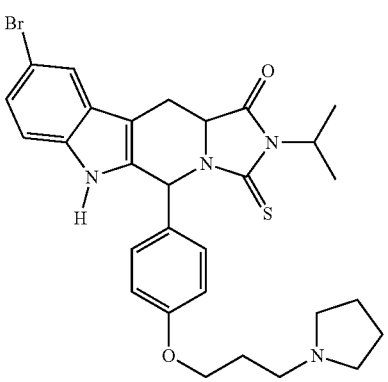
151
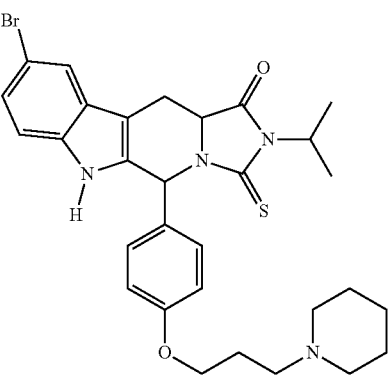

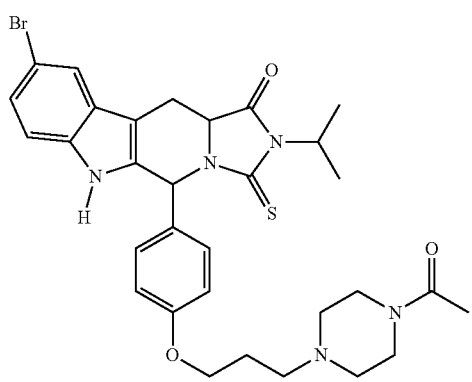
152
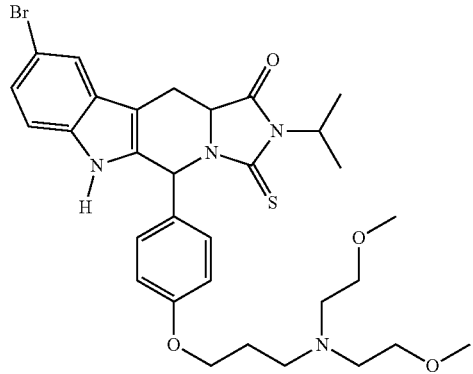
156
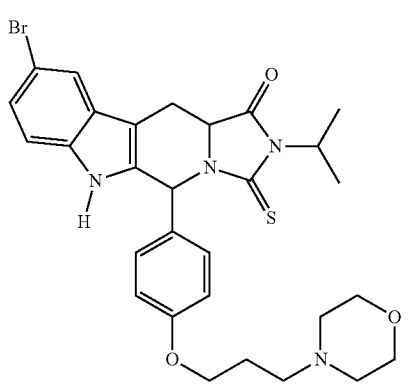
153
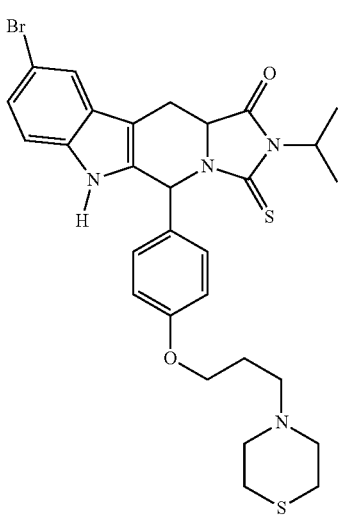
157
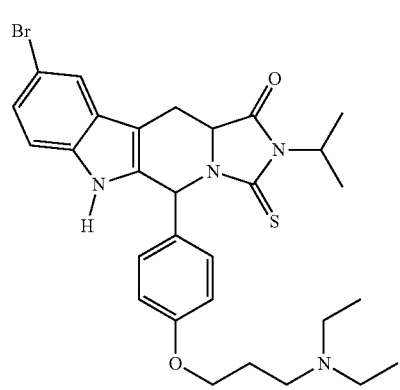
154
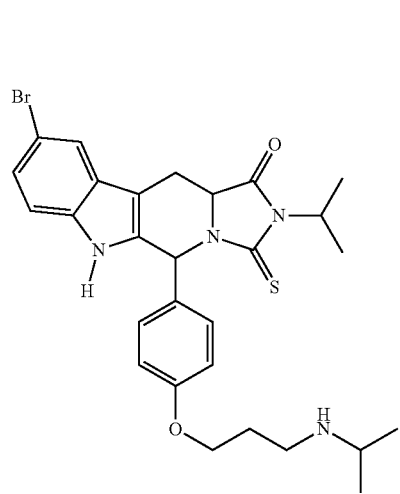
155
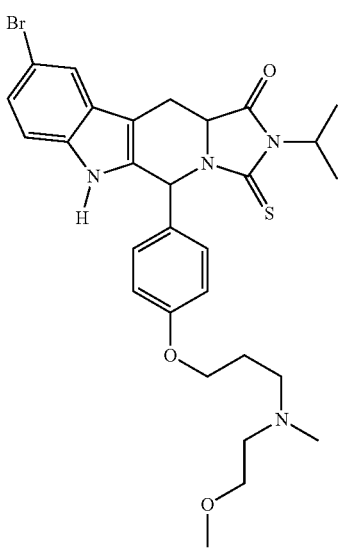
158

51
-continued
159
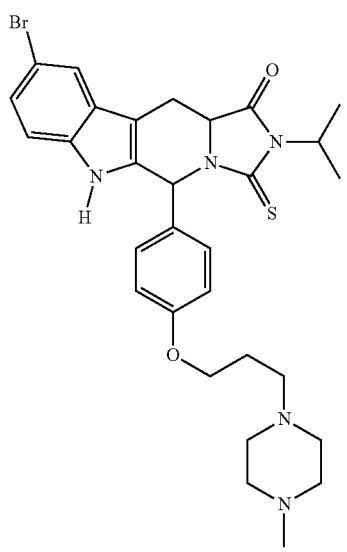
160
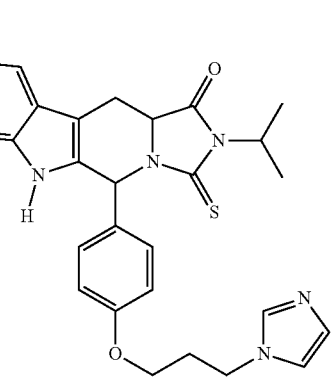
161
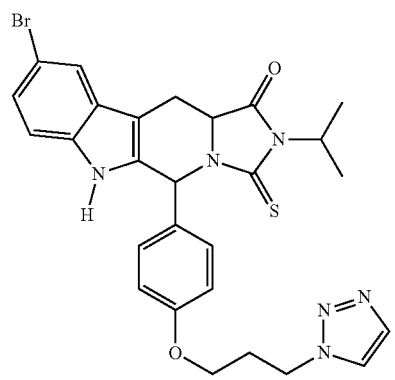
52
-continued
162
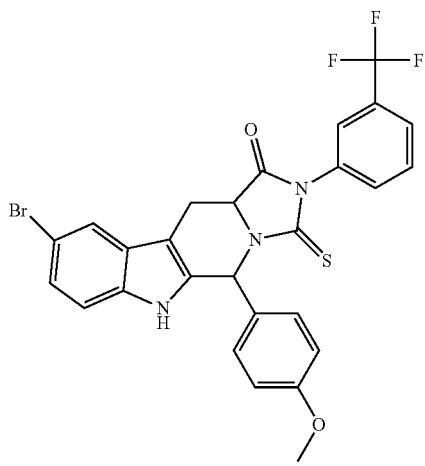
163
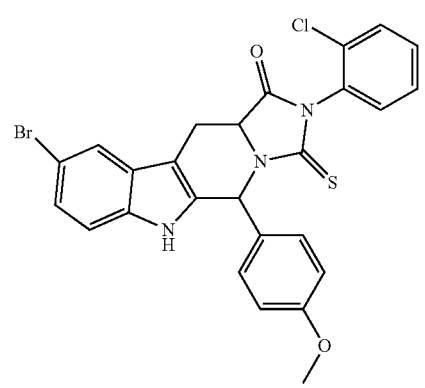
164

165
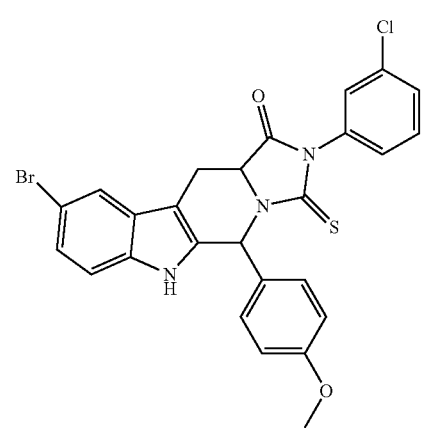
166
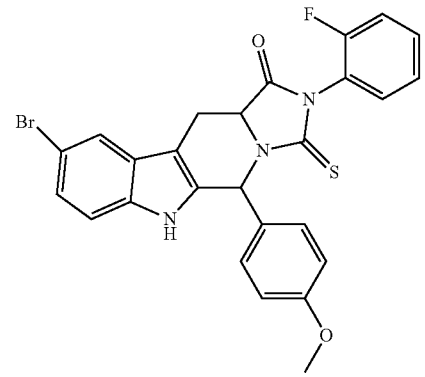
167
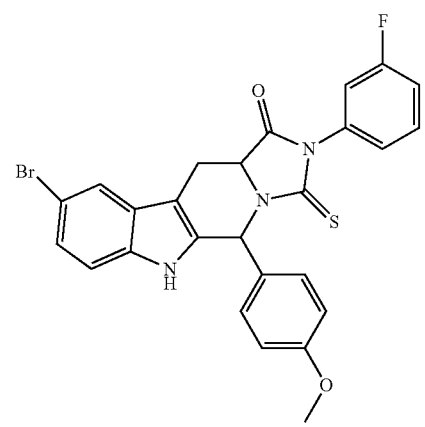
168
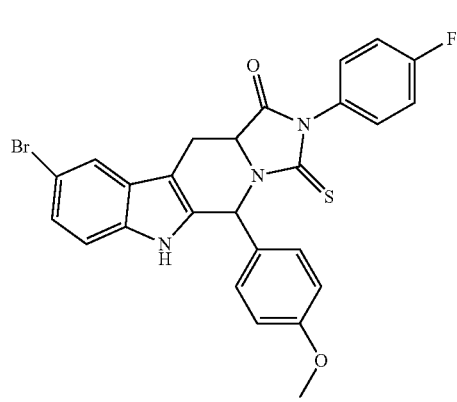
169
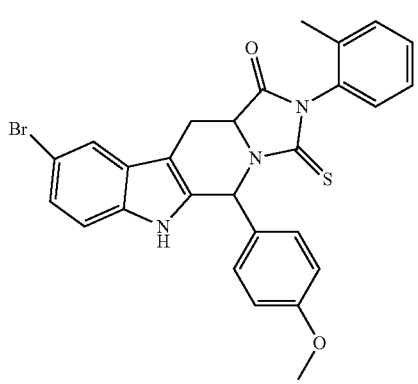
170
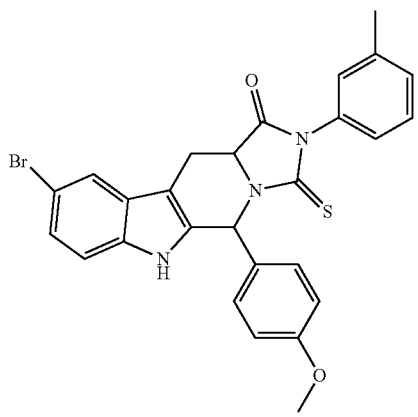
171
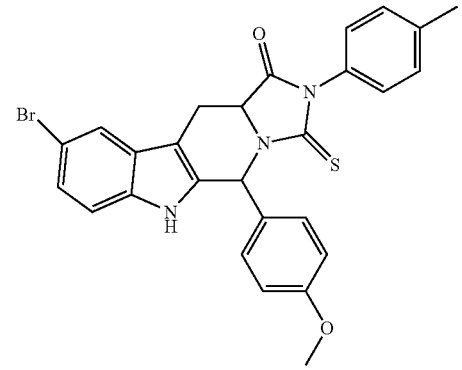
172
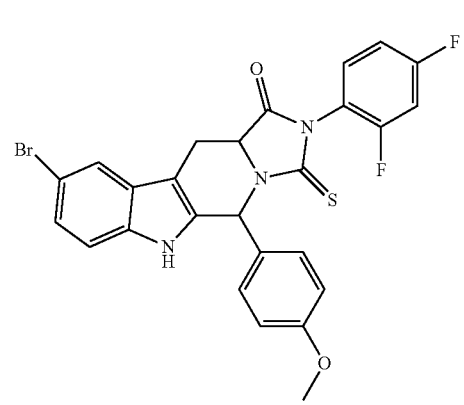

173
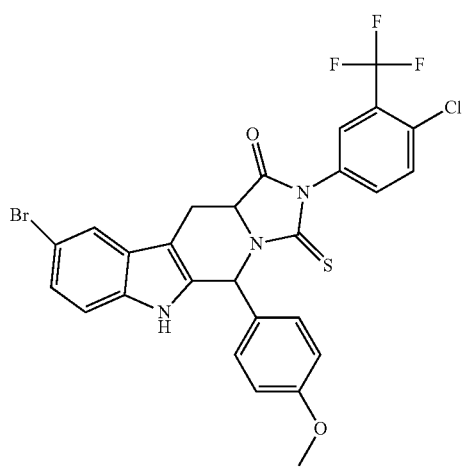
174
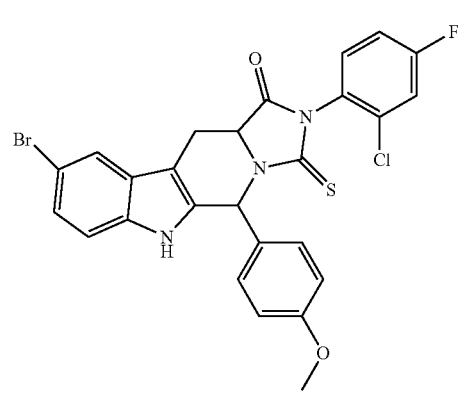
175
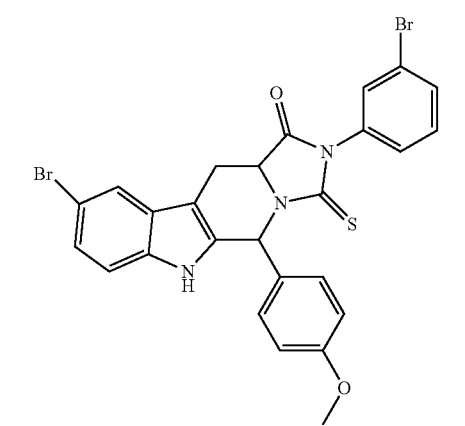
176
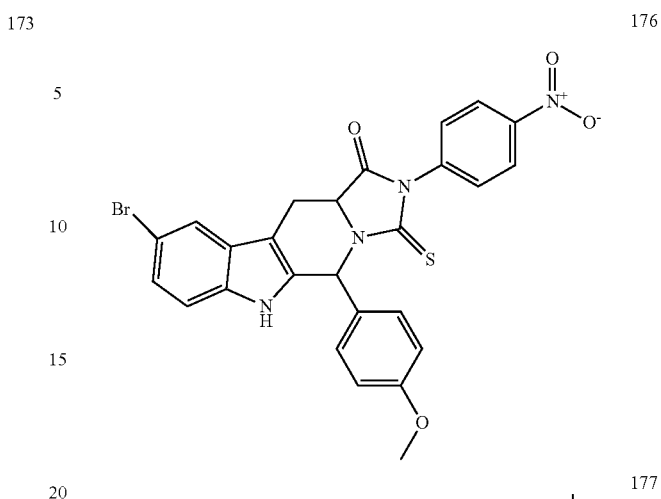
177
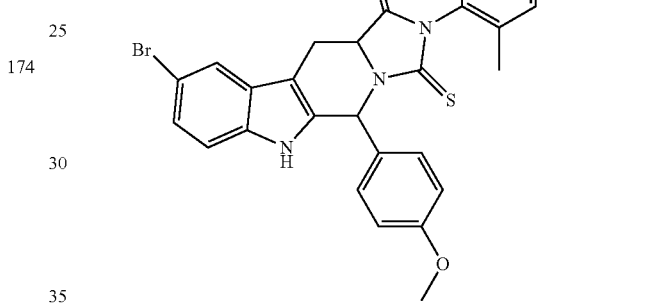
178
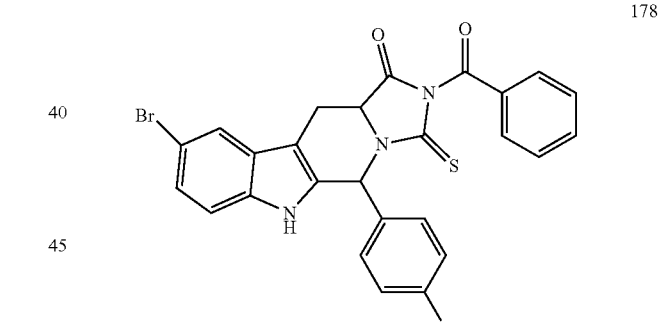
179
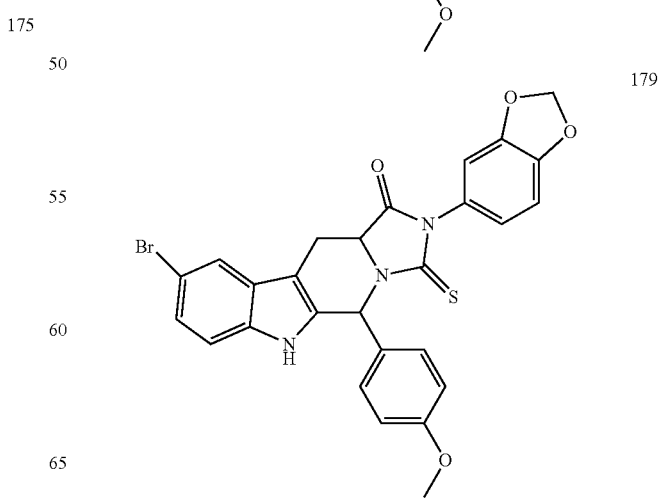

-continued
180
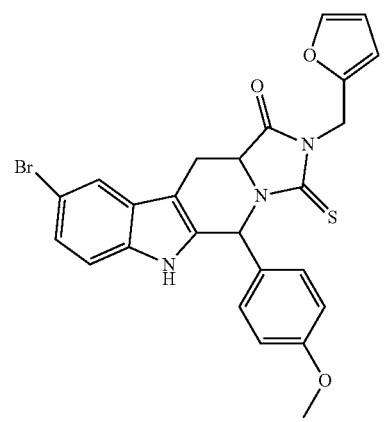
181
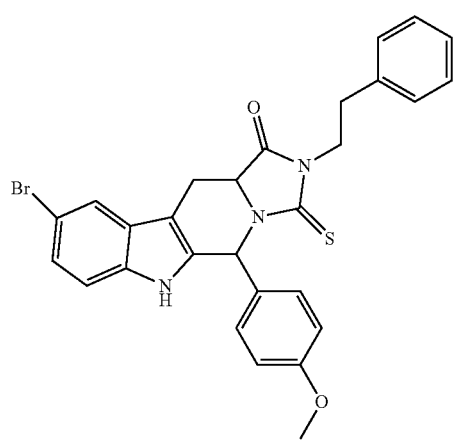
182
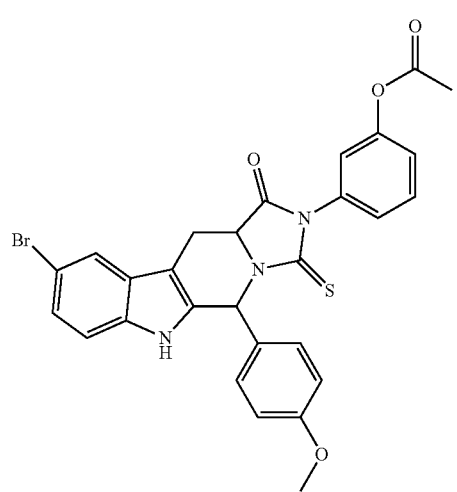
-continued
183
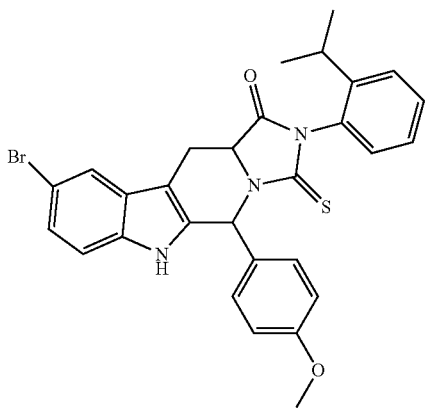
184
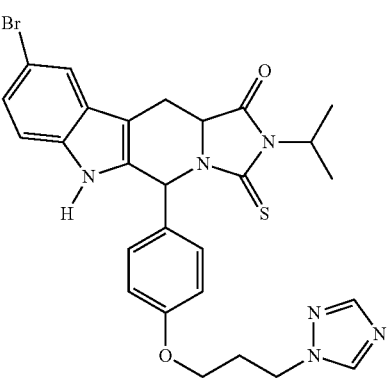
185
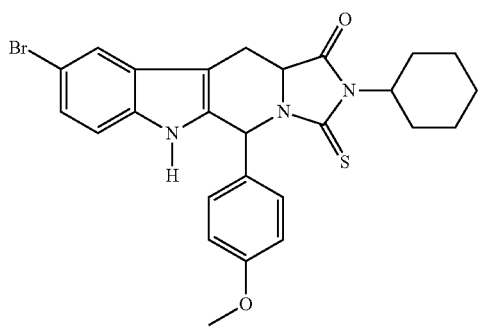
186
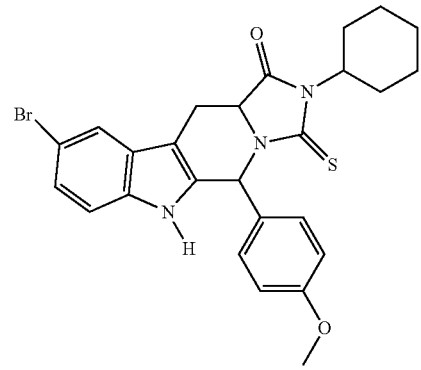

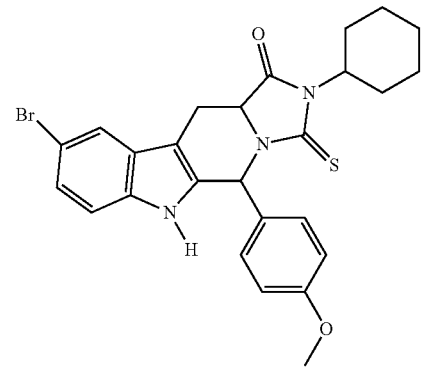
187
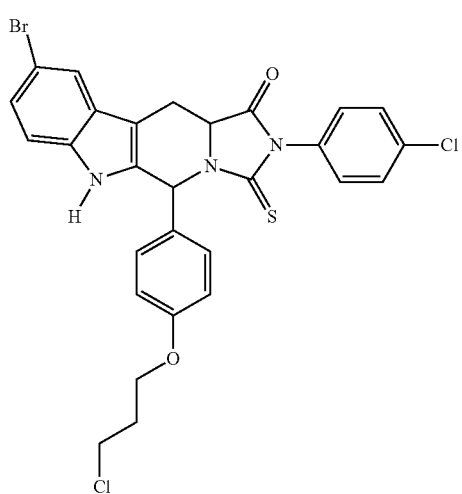
188
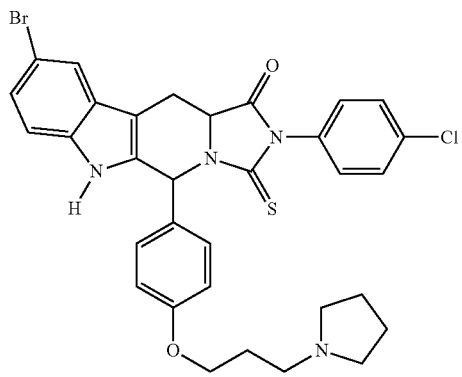
189
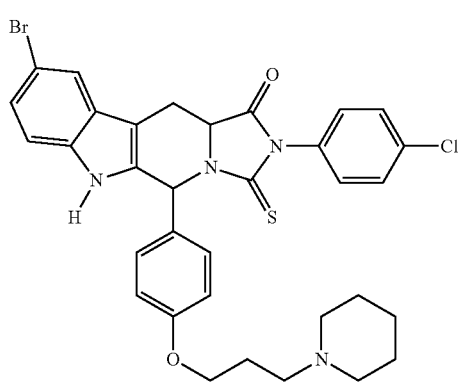
190
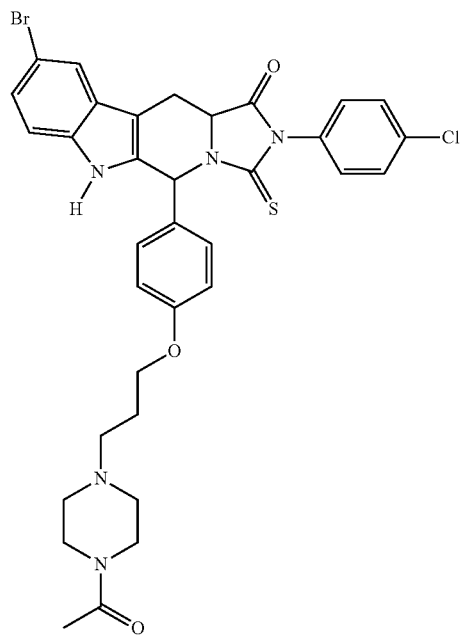
191
192

61
-continued
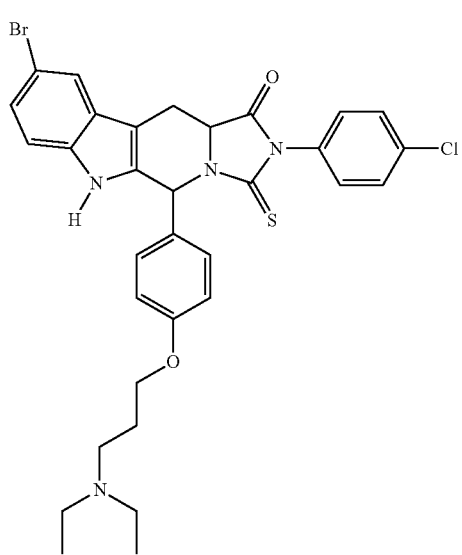
193
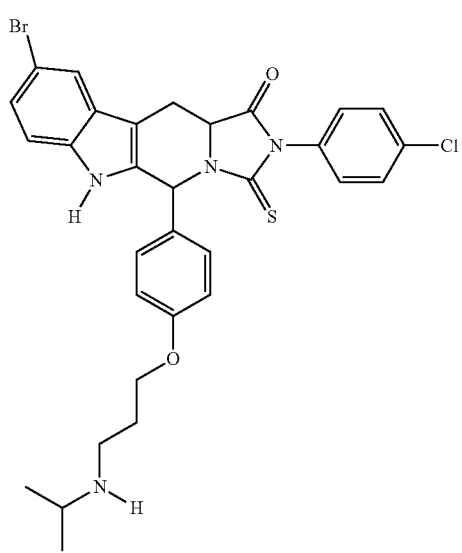
194
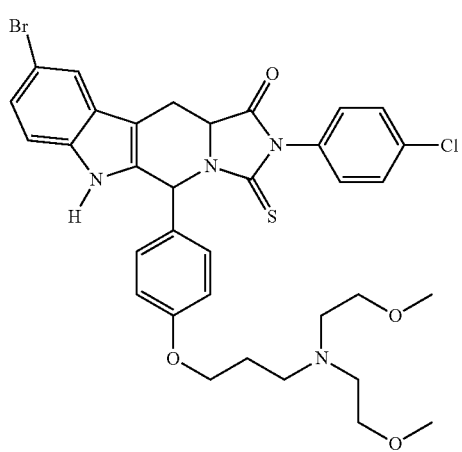
195
62
-continued
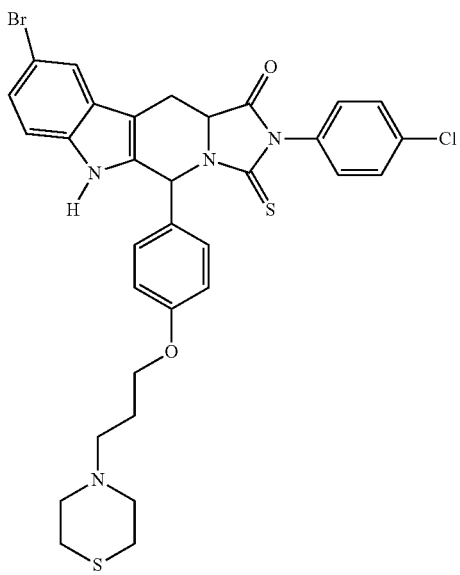
196
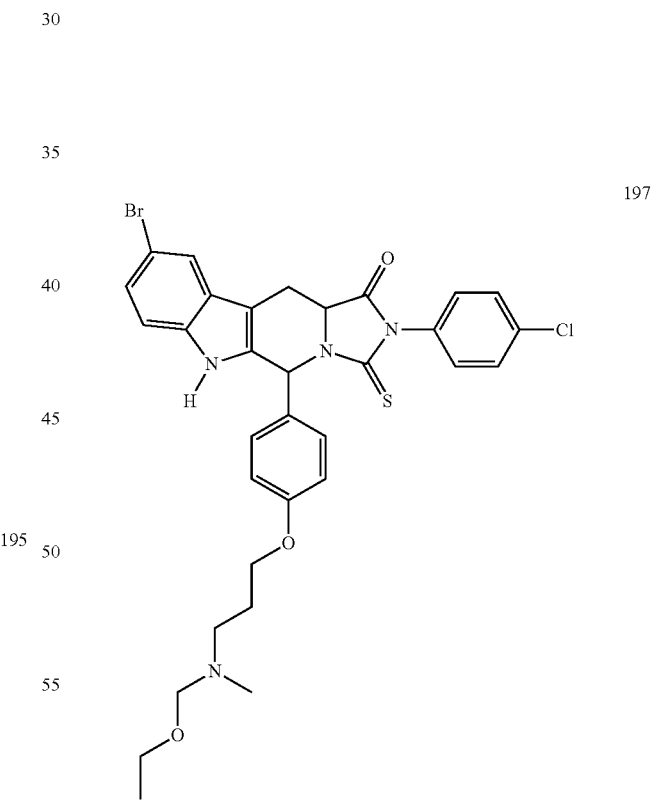
197

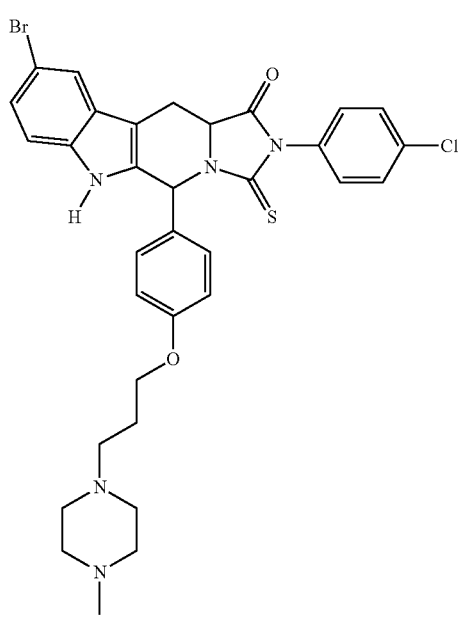

198

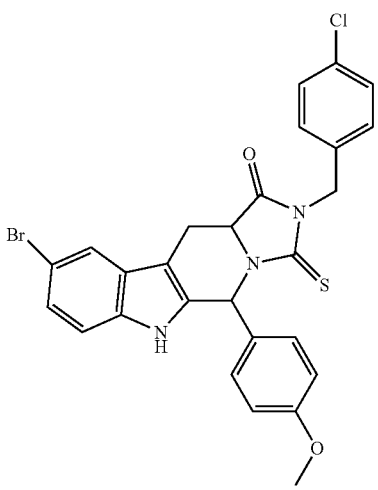

201

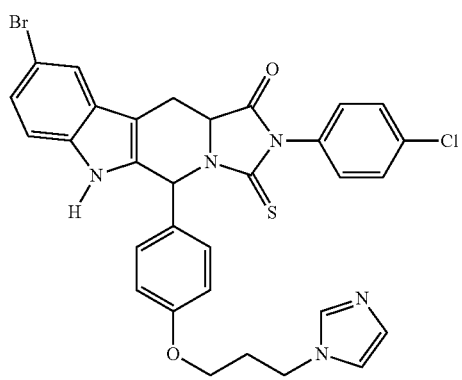

199

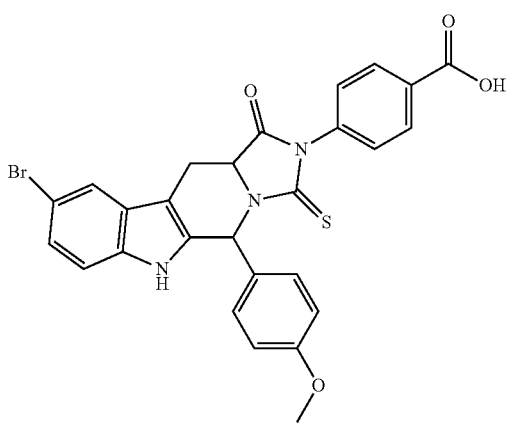

200

In certain embodiments, preferred compounds include those with an EC$_{50}$ in the VEGF ELISA assay described in Example 2 of less than about 2 uM, more preferably between about 2 uM and about 0.04 uM (200 nM to 40 nM); more preferably from about 0.04 uM to about 0.008 uM to (40 nM to 8 nM); and more preferably less than about 0.008 uM (<8 nM). Particularly preferred compounds are Compound NOs: 1-27, particularly, 1, 2, 8, 14, 16, and 17. In one embodiment, the preferred compounds of the invention form a racemic mixture, and in another embodiment the compounds of the invention are in enantiomerically pure composition. More preferably, the compounds of the invention are 5S, 11aR isomer, in an enantiomerically pure composition.

The above compounds are listed only to provide examples that may be used in the methods of the invention. Based upon the instant disclosure, the skilled artisan would recognize other compounds intended to be included within the scope of the presently claimed invention that would be useful in the methods recited herein.

B. Preparation of Compounds of the Invention

Compounds of the invention may be produced in any manner known in the art. By way of example, compounds of the invention may be prepared according to the following general schemes. More specifically, Scheme I may be used to make compounds of Formula (I).

Scheme I

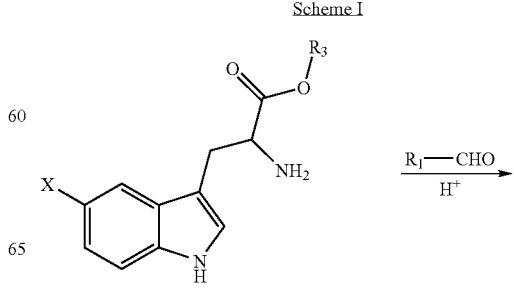

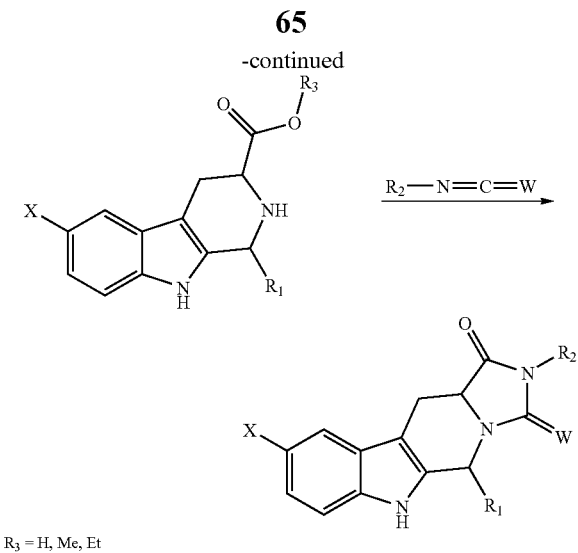

R₃ = H, Me, Et

More particularly, in certain embodiments, exemplary methods of Scheme I for preparing preferred compounds of Formula (I-a) involve the formation of free amine Pictet-Spengler reaction products/intermediates, as described below in Procedure-I.

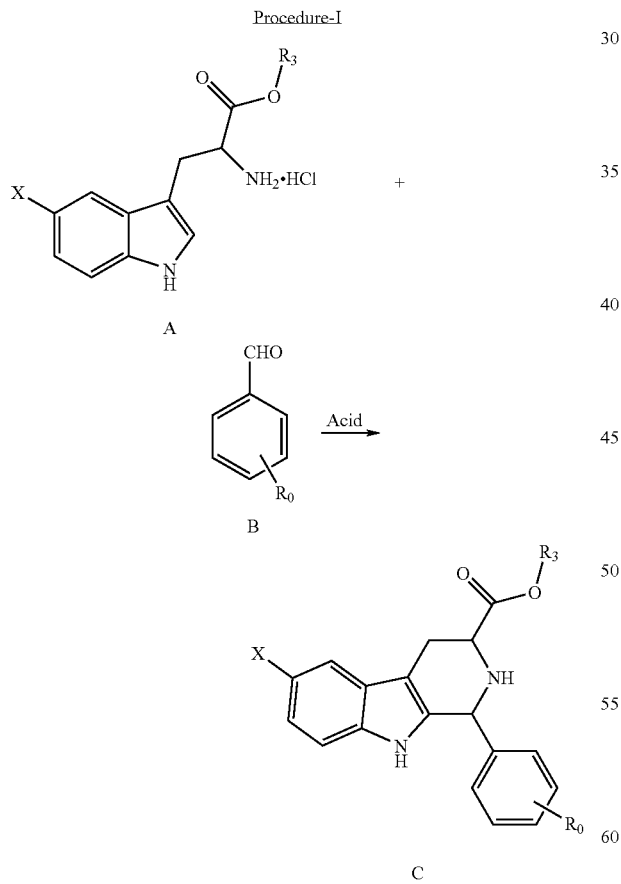

In one embodiment, Procedure-I may involve adding a desired aldehyde (B) to a suspension of 5-substituted tryptophan HCl (A) in 0.1N sulfuric acid. The solution may then be stirred at about 110° C.-120° C. in a closed reaction vessel until the reaction is sufficiently complete, e.g., for about 15 minutes to about 20 hours. After completion of the reaction, the reaction mixture may be cooled to room temperature and the precipitated salt may be filtered. The filtered residue may then be washed with ether, EtOAc or a mixture of DCM and DMF and dried to give the product (III) as a corresponding acid salt. Alternatively, a desired aldehyde (B) may be added to a suspension of 5-substituted tryptophan (A) in acetic acid and refluxed until the reaction is sufficiently complete, e.g., for about 15 minutes to about 20 hours. After completion of the reaction, the reaction mixture may be cooled to room temperature and the corresponding acid salt may be filtered. The filtered residue may then be washed with acetic acid followed by DCM and dried to give the product (C) as a salt. The free amine (C) may be obtained by extraction with EtOAc and washing with aqueous ammonium hydroxide or 1M aq. sodium hydroxide. The free amine reaction product/intermediate, or its salt, may then be used to form other preferred compounds of Formula Ia.

In certain preferred embodiments, compounds of the invention may be resolved to enantiomerically pure compositions or synthesized as enantiomerically pure compositions using any method known in the art. By way of example, compounds of the invention may be resolved by direct crystallization of enantiomeric mixtures, by diastereomeric salt formation of enantiomers, by the formation and separation of diastereoiomers or by enzymatic resolution of a racemic mixture.

By way of example, enantiomerically pure compounds of the invention may be synthesized from enantiomerically pure starting materials obtained in a manner similar to those illustrated in Scheme II or Scheme III (see, e.g., procedure in *Inte J of Pep and Pro Res,* 130(1), 13-21 (1987).

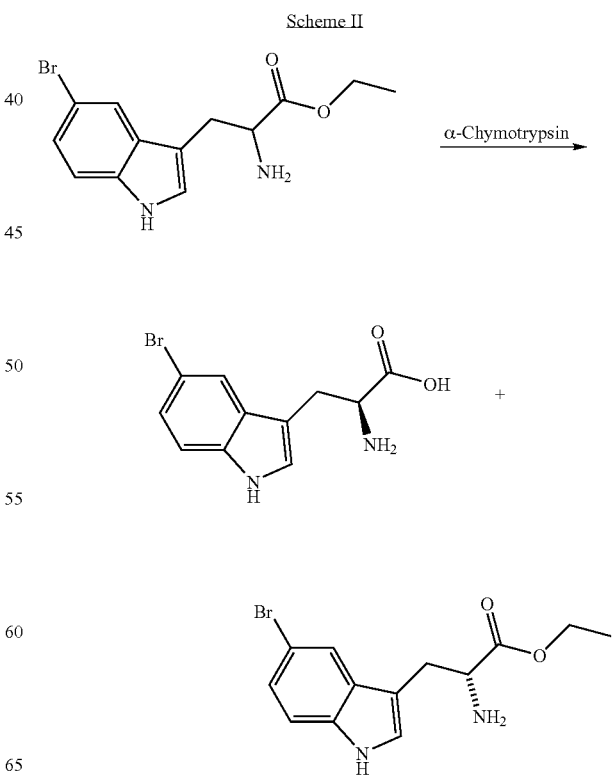

Scheme III

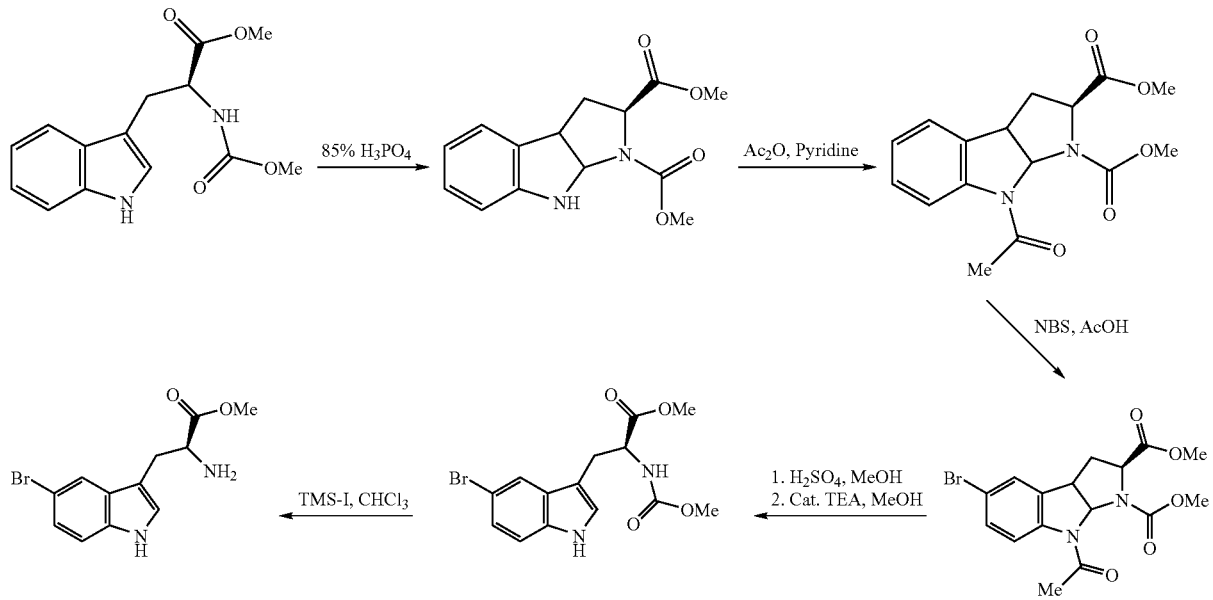

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the inhibition of VEGF production, the inhibition of angiogenesis, and/or the treatment of cancer, diabetic retinopathy, rheumatoid arthritis, psoriasis, atherosclerosis, chronic inflammation, other chronic inflammation-related diseases and disorders, obesity, or exudative macular degeneration using the compounds described herein.

In one embodiment, the invention is directed to methods for inhibiting VEGF production comprising administering a VEGF-expression inhibiting amount of at least one compound of the invention to a subject in need thereof.

In another embodiment, methods for inhibiting angiogenesis are provided comprising administering an anti-angiogenic amount of at least one compound of the invention to a subject in need thereof.

In yet another embodiment, methods for treating cancer, diabetic retinopathy, rheumatoid arthritis, psoriasis, atherosclerosis, chronic inflammation, other chronic inflammation-related diseases and disorders, obesity, or exudative macular degeneration are provided comprising administering a therapeutically effective amount of at least one compound of the invention to a subject in need thereof.

Without intending to be limited by theory, it is believed that the methods of the present invention act through a combination of mechanisms that modulate the activity of VEGF. In preferred embodiments, the methods of the invention comprise administering a therapeutically effective amount of at least one compound of the invention, wherein the compound is an 10S, 3aR isomer.

According to the methods of the invention, the compound(s) may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The terms "VEGF-inhibiting amount", "anti-angiogenic amount", and "therapeutically effective amount", as used herein, refer to an amount of a pharmaceutical agent to treat, ameliorate, or prevent the identified disease or condition, or to exhibit a detectable therapeutic or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 μg/mL to approximately 100 μg/mL, preferably from approximately 5 μg/mL to approximately 50 μg/mL, more preferably from approximately 5 μg/mL to approximately 10 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-$\beta$-cyclodextrin (HPBC), which may be added to any of the above-described compositions to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

F. Combination Therapy

It is also possible to combine any compound of the present invention with one or more other active ingredients useful in the treatment of cancer, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the VEGF-inhibiting and/or anti-angiogenesis activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Compounds of Formula I may be prepared according to Scheme I. By way of example, Compounds 23, 33, 35 and 40 may be prepared as follows. Other preferred compounds of the invention, such as those in Table 4 below, may be similarly prepared.

Example 1A

Synthesis of Compound 2 (Racemic)

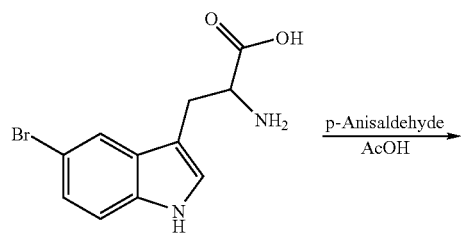

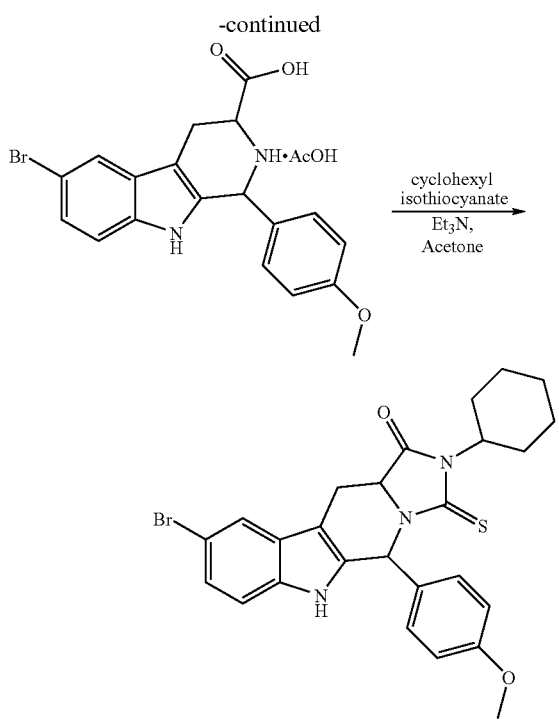

In accordance with Scheme I, p-anisaldehyde (2.16 g, 15.9 mmol, 1.93 mL) is added to a suspension of 5-Bromotryptophan (3 g, 10.6 mmol) in 100 mL of Acetic acid at room temperature. The reaction mixture is then heated to reflux at about 125° C. in silicon oil bath and maintained at that temperature for about 3 hours 20 minutes. The resulting solution is concentrated under vacuum. The residue is triturated with dichloromethane, diethyl ether and hexane to yield powdery brown solid. The resulting acid salts of the desired product are then collected and washed with hexane three times and then, used for next step without purification.

The collected brown solid is suspended in 60 ml of acetone. The suspension is treated with triethylamine (14.37 mmol, 2 mL) and cyclohexyl isothiocyanate (2.03 g, 14.37 mmol, 2.04 mL) to give a homogenous solution. The reaction mixture is refluxed for about 2.5 hours at about 70° C., and then concentrated under vacuum. The residue is purified on silica gel with 10% to 15% to 20% EtOAc in hexane to yield 4.13 g of the desired product (82%). MS (MH+) m/z=525.23, Rt: 4.23.

Example 1B

Synthesis of Compound 14

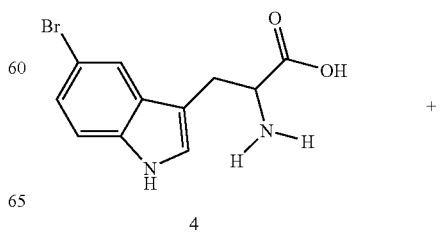

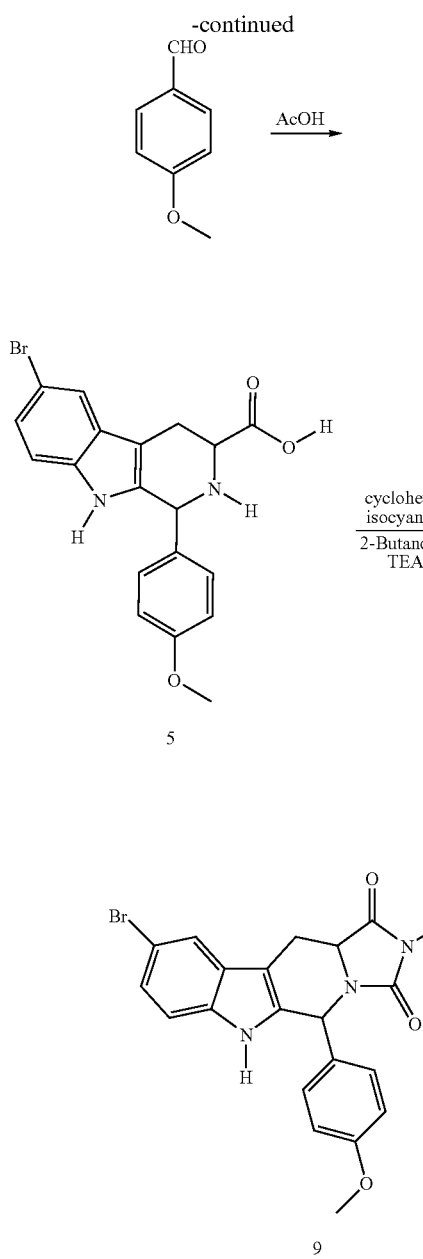

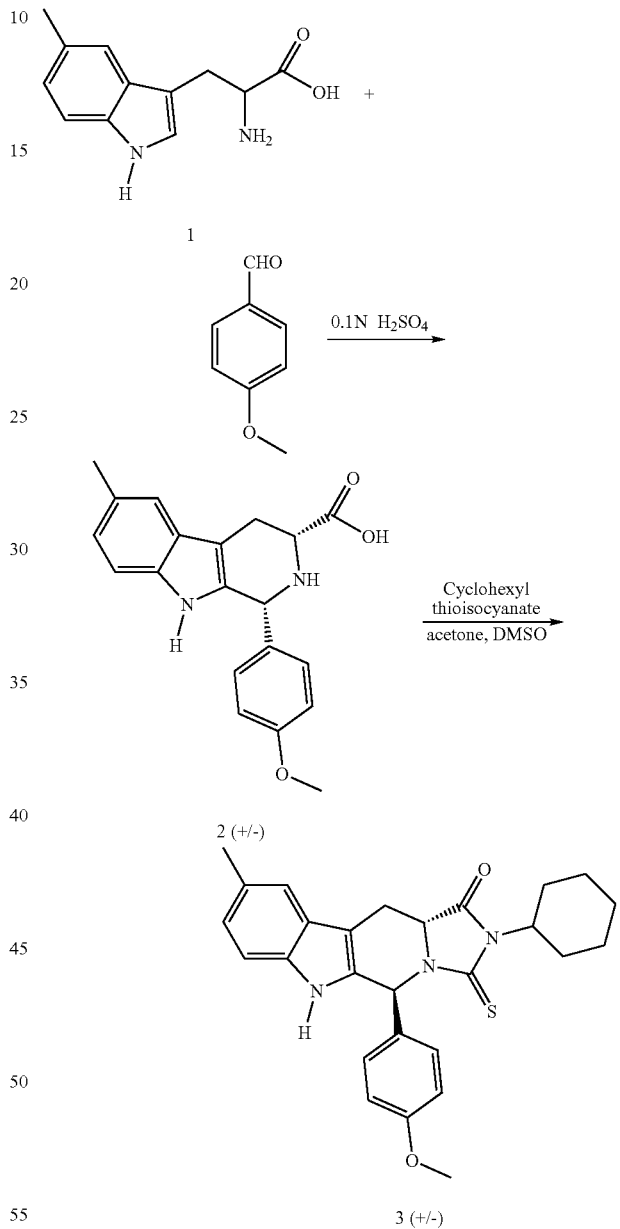

EtOAc in methylene chloride to give 6 as a white powder, 45 mg, 59% yield. MS (ES+) m/z: 508/510.23, Rt: 4.20 min.

Example 1C

Synthesis of Compound 16

In accordance with Scheme I, p-anisaldehyde (0.18 ml, 1.5 mmol) is added to 5-bromotryptophan (283 mg, 1.0 mmol) in AcOH (1.5 ml) and heated to about 110° C. in a capped tube. The solids are dissolved upon heating. After about 2.5 h, the reaction mixture is cooled to room temperature and concentrated on rotavap. The thick oil residue is stirred in $CH_3CN$ (2 ml) and a brownish solid precipitated out. The solid is filtered and washed with $CH_3CN$ (2×) to give 5 as a light brown powder, 0.20 g, 50% yield. The product was 95% pure by LC-MS, contaminated with 3% of 4 and 2% of p-anisaldehyde, and it is used without further purification. MS (ES+) m/z: 401/403.13, Rt: 2.45 min.

To a solution of 5 (55.5 mg, 1.5 mmol) in 2-butanone (1.5 ml) and TEA (0.2 ml) is added cyclohexylisocyanate. The mixture is heated at 100° C. in a capped tube. After 2 h, the reaction mixture was cooled to room temperature, concentrated on rotavap. The residue was chromatographed with 2% EtOAc in methylene chloride to give 6 as a white powder, 45 mg, 59% yield.

In accordance with Scheme I, p-anisaldehyde (0.25 ml, 2.0 mmol) is added to a suspension of 1 (218 mg, 1.0 mmol) in 0.1 $NH_2SO_4$ (5 ml). The reaction mixture is heated to about 100° C. overnight. The reaction mixture is then cooled to room temperature, filtered, the solid washed with water (2×), hexanes (3×) and ether (2×), and dried in air to give 2 as a tan-colored powder, 320 mg, 95% yield. The product was contaminated with 4.7% p-anisaldehyde by LC-MS, and is used without further purification. MS (ES+) m/z: 337.25, Rt: 2.36 min.

Cyclohexyl thioisocyanate (28 μl, 0.2 mmol) is then added to a mixture of 2 (67 mg, 0.2 mmol) in acetone (2.0 ml) and DMSO (0.4 ml) in a 10 ml screw tube. The tube is capped and the mixture heated at to about 70° C. (heating block temperature) for about 36 h. The reaction mixture is then concentrated to dryness and chromatographed (10% EtOAc in hexanes) to give 3 (Compound 16) as a yellowish solid, 55 mg, 60% yield. MS (ES+) m/z: 460.27, Rt: 4.64 min.

Example 1D

Synthesis of Compound 17

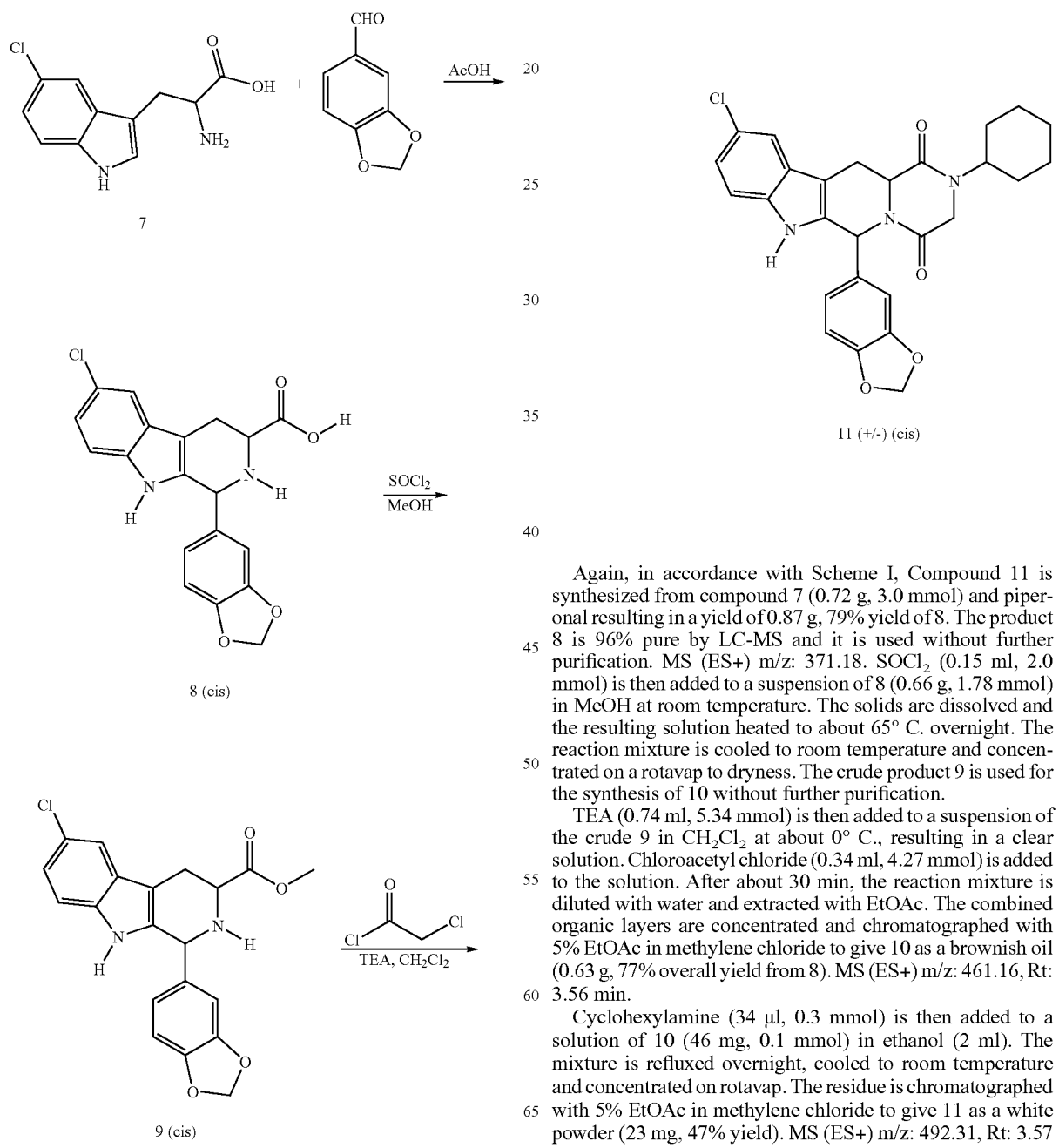

Again, in accordance with Scheme I, Compound 11 is synthesized from compound 7 (0.72 g, 3.0 mmol) and piperonal resulting in a yield of 0.87 g, 79% yield of 8. The product 8 is 96% pure by LC-MS and it is used without further purification. MS (ES+) m/z: 371.18. SOCl₂ (0.15 ml, 2.0 mmol) is then added to a suspension of 8 (0.66 g, 1.78 mmol) in MeOH at room temperature. The solids are dissolved and the resulting solution heated to about 65° C. overnight. The reaction mixture is cooled to room temperature and concentrated on a rotavap to dryness. The crude product 9 is used for the synthesis of 10 without further purification.

TEA (0.74 ml, 5.34 mmol) is then added to a suspension of the crude 9 in CH₂Cl₂ at about 0° C., resulting in a clear solution. Chloroacetyl chloride (0.34 ml, 4.27 mmol) is added to the solution. After about 30 min, the reaction mixture is diluted with water and extracted with EtOAc. The combined organic layers are concentrated and chromatographed with 5% EtOAc in methylene chloride to give 10 as a brownish oil (0.63 g, 77% overall yield from 8). MS (ES+) m/z: 461.16, Rt: 3.56 min.

Cyclohexylamine (34 μl, 0.3 mmol) is then added to a solution of 10 (46 mg, 0.1 mmol) in ethanol (2 ml). The mixture is refluxed overnight, cooled to room temperature and concentrated on rotavap. The residue is chromatographed with 5% EtOAc in methylene chloride to give 11 as a white powder (23 mg, 47% yield). MS (ES+) m/z: 492.31, Rt: 3.57 min.

Example 1E

Preparation of Chiral Starting Materials

Compounds of the invention may optionally be prepared as enantiomerically pure compositions by using enantiomerically pure starting materials, preferably prepared as follows.

Enzymatic resolution of 5-Bromo-tryptophan

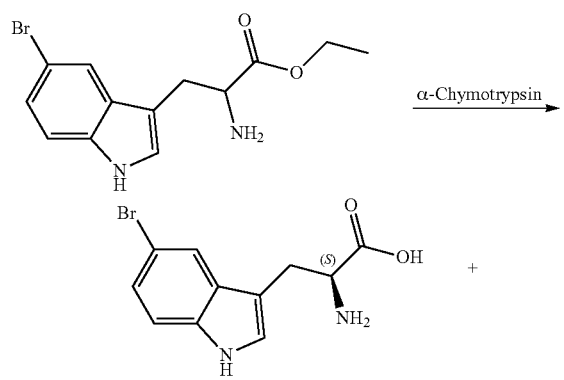

In accordance with Scheme II, a racemic ester (4.15 g, 13.34 mmol) is dissolved in acetonitrile (60 ml) and diluted with water (120 ml). The pH of the mixture is adjusted to 7.0 using 1 N HCl. Potassium chloride (230 mg) and α-chymotrypsin (40 mg) are added. The pH of the mixture is maintained at 7.0 using 0.5 N NaOH throughout the resolution by use of an automatic titrator. The reaction is monitored by LC-MS. After about 3 h, additional α-chymotrypsin (30 mg) is added, and asymmetric hydrolysis is completed in about another 3 h. The resulting white cloud mixture is concentrated on rotavap to remove acetonitrile, diluted with EtOAc (100 ml) and basified to pH=12-13 by 5 N NaOH. The mixture is then filtered through celite. The aqueous fraction is extracted with EtOAc (3×). The combined organics are washed with 0.5 N NaOH, dried over $Na_2SO_4$ and concentrated to give the unhydrolyzed D-isomer as a tan-colored solid, 1.97 g, 48% yield. Chiral chromatography, 97% pure and >99% ee. The combined aqueous layers are acidified to pH=6.0. The resulting white solid is filtered, washed with water (2×) and dried in oven (95° C.) to give the S-isomer, 1.54 g, 42% yield. LC-MS: 100% pure.

Chiral synthesis of 5-Bromo-tryptophan

Alternatively, enantiomerically pure starting materials may be synthesized in accordance with Scheme III as follows (see, e.g., Taniguchi, M.; Hino, T. *Tetrahedron* 1981, 37, 1487; Irie, K.; Ishida, A.; Nakamura, T.; Oh-Ishi, T. *Chem. Pharm. Bull.* 1984, 32, 2126).

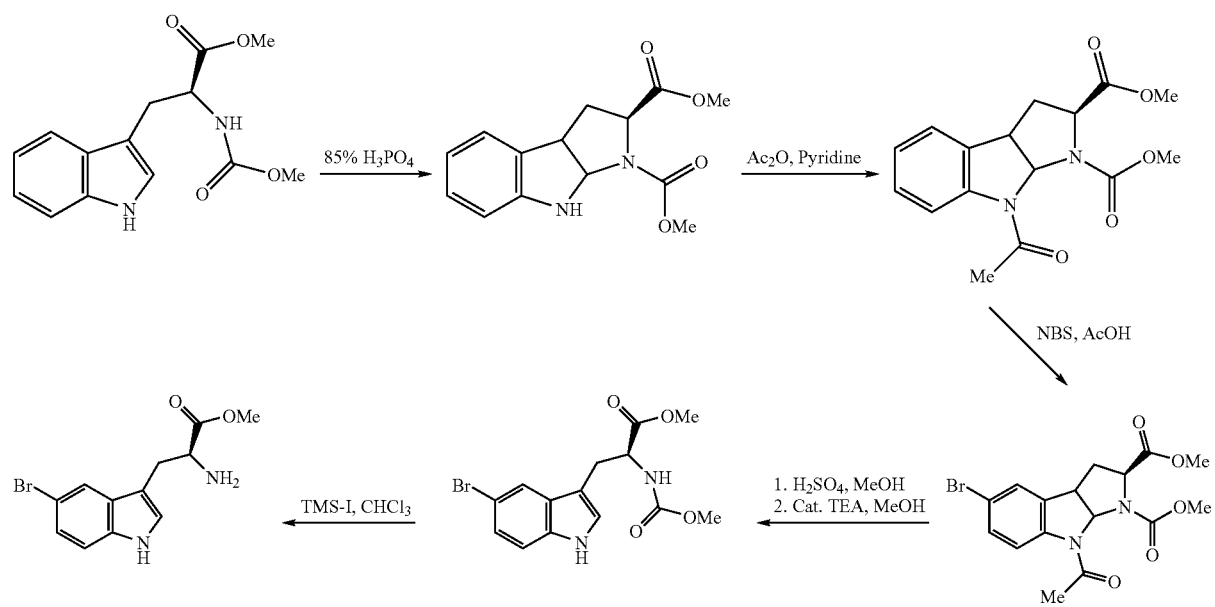 [SMILES: COC(=O)N[C@@H](Cc1c[nH]c2ccccc12)C(=O)OC ; COC(=O)[C@@H]1CC2c3ccccc3NC2N1C(=O)OC ; COC(=O)[C@@H]1CC2c3ccccc3N(C(C)=O)C2N1C(=O)OC ; COC(=O)[C@@H](N)Cc1c[nH]c2ccc(Br)cc12 ; COC(=O)N[C@@H](Cc1c[nH]c2ccc(Br)cc12)C(=O)OC ; COC(=O)[C@@H]1CC2c3cc(Br)ccc3N(C(C)=O)C2N1C(=O)OC]

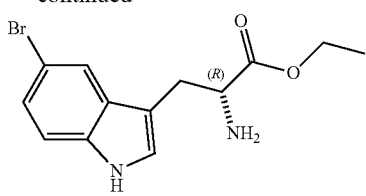

Methyl 5-Bromo-(D)-Tryptophan Ester may also prepared through the same sequence.

Example 2

Assay to Evaluate Affect on Hypoxia-Inducible Endogenous VEGF Expression

The ability of the compounds of the invention to modulate hypoxia-inducible endogenous VEGF expression may be analyzed as follows. VEGF protein levels may be monitored by an ELISA assay (R&D Systems). Briefly, HeLa cells may be cultured for 24-48 hours under hypoxic conditions (1% $O_2$, 5% $CO_2$, balanced with nitrogen) in the presence or absence of a compound of the invention. The conditioned media may then be assayed by ELISA, and the concentration of VEGF calculated from the standard ELISA curve of each assay.

A dose-response analysis may be performed using the ELISA assay and conditions described above. The conditions for the dose-response ELISA are analogous to those described above. A series of, e.g., seven different concentrations may be analyzed. In parallel, a dose-response cytotoxicity assay may be performed using CellTiter Glo (Promega) under the same conditions as the ELISA to ensure that the inhibition of VEGF expression was not due to the cytotoxicity. Dose-response curves may be plotted using percentage inhibition versus concentration of the compound, and $EC_{50}$ and $CC_{50}$ values may be generated for each compound with the maximal inhibition set as 100% and the minimal inhibition as 0%. Preferred compounds of the invention will have an $EC_{50}$ of less than 50, preferably less than 10, more preferably less than 2, even more preferably less than 0.5, and even more preferably less than 0.01.

FIG. 1 shows the ability of a typical compound of the invention, Compound No. 2 to inhibit endogenous VEGF production in tumor cells under hypoxic conditions. The ELISA $EC_{50}$ is 0.0025, while its $CC_{50}$ (0.22 μM cytotoxicity) is greater than 20 nm. The $EC_{50}$ for a series of preferred compounds of the invention is provided in Table 4.

TABLE 4

| Compound | Stereochemistry | LCMS [MH+] | LCMS Retention Time (min) | ELISA $EC_{50}$ uM |
|---|---|---|---|---|
| 1 | Trans-racemic | 422.35 | 4.64 | * |
| 2 | (Trans-racemic) | 446.33 | 4.3 | * |
| 3 | (Trans-racemic) | 460.33 | 4.26 | * |
| 4 | (Trans-racemic) | 434.33 | 4.3 | * |
| 5 | (Trans-racemic) | 380.31 | 3.9 | * |
| 6 | (Trans-racemic) | 404.29 | 3.69 | * |
| 7 | (Trans-racemic) | 418.27 | 3.7 | ** |
| 8 | (Trans-racemic) | 418.27 | 3.65 | ** |
| 9 | (Trans-racemic) | 540.24 | 4.02 | **** |
| 10 | (Trans-racemic) | 512.28 | 4.07 | **** |
| 11 | (Trans-racemic) | 408.37 | 3.92 | ** |
| 12 | (Trans-racemic) | 432.36 | 3.73 | * |
| 13 | (Trans-racemic) | 432.36 | 3.68 | *** |
| 14 | (Trans-racemic) | 446.33 | 3.75 | ** |
| 15 | (Trans-racemic) | 460.21 | 3.73 | ** |
| 16 | (Trans-racemic) | 484.15 | 3.5 | ***** |
| 17 | (Trans-racemic) | 484.15 | 3.48 | ***** |
| 18 | (Trans-racemic) | 498.14 | 3.45 | ***** |
| 19 | (Trans-racemic) | 488.23 | 4.39 | **** |
| 20 | (Trans-racemic) | 512.22 | 4.02 | ***** |
| 21 | (Trans-racemic) | 512.20 | 4.0 | ***** |
| 22 | (Trans-racemic) | 524.16 | 4.0 | ***** |
| 23 | (Trans-racemic) | 460.27 | 4.64 | **** |
| 24 | (Trans-racemic) | 460.33 | 3.86 | *** |
| 25 | (Trans-racemic) | 494.26 | 4.02 | ***** |
| 26 | (Trans-racemic) | 621, 623 | 3.19 | *** |
| 27 | Trans-racemic | 524, 526 | 4.77 | ***** |
| 28 | (Trans-racemic) | 526.28 | 4.03 | **** |
| 29 | (Trans-racemic) | 522.20 | 4.17 | **** |
| 30 | (Trans-racemic) | 502.33 | 4.27 | *** |
| 31 | (Trans-racemic) | 478.25 | 4.12 | *** |
| 32 | (Trans-racemic) | 458 | 3.32 | *** |
| 33 | (Cis-racemic) | 390.31 | 3.45 | *** |
| 34 | (Trans-racemic) | 458 | 3.34 | ** |
| 35 | (Racemic) | 466.27 | 4.09 | ** |
| 36 | (Trans-racemic) | 450 | 3.97 | * |
| 37 | (Trans-racemic) | 458 | 3.31 | * |
| 38 | (Trans-racemic) | 472 | 4.20 | * |
| 39 | (Trans-racemic) | 462 | 3.24 | ** |
| 40 | (Trans-racemic) | 446.21 | 4.48 | ** |

TABLE 4-continued

| Compound | Stereochemistry | LCMS [MH+] | LCMS Retention Time (min) | ELISA $EC_{50}$ uM |
|---|---|---|---|---|
| 41 | (Trans-racemic) | 446.21 | 4.48 | ** |
| 42 | (Trans-racemic) | 406.19 | 4.1 | ** |
| 43 | (Trans-racemic) | 458.17 | 3.93 | ** |
| 44 | (Cis-racemic) | 458.29 | 3.90 | ** |
| 45 | (Cis-racemic) | 444.32 | 4.01 | ** |
| 46 | (Trans-racemic) | 454.21 | 4.0 | * |
| 47 | (Trans-racemic) | 458 | 4.52 | * |
| 48 | (Trans-racemic) | 430.29 | 3.95 | * |
| 49 | (Trans-racemic) | 446 | 4.62 | * |
| 50 | (Racemic) | 424.23 | 3.7 | * |
| 51 | (Trans-racemic) | 498.18 | 3.88 | * |
| 52 | (Trans-racemic) | 406 | 4.16 | * |
| 53 | (Trans-racemic) |  |  | * |
| 54 | (Racemic) | 430.29 | 3.81 | * |
| 55 | (Trans-racemic) | 454.20 | 3.52 | * |
| 56 | (Trans-racemic) | 416.26 | 4.45 | * |
| 57 | (Trans-racemic) | 440 | 3.94 | * |
| 58 | (Trans-racemic) |  |  | * |
| 59 | (Trans-racemic) | 422.19 | 3.75 | * |
| 60 | (Racemic) | 390.29 | 3.67 | * |
| 61 | (Trans-racemic) | 404 | 3.97 | * |
| 62 | (Trans-racemic) | 436.23 | 3.85 | * |
| 63 | (Trans-racemic) |  |  | * |
| 64 | (Trans-racemic) |  |  | * |
| 65 | (Trans-racemic) |  |  | * |
| 66 | (Racemic) | 376.27 | 3.47 | * |
| 67 | (Trans-racemic) | 408 | 3.22 | * |
| 68 | (Trans-racemic) | 410 | 3.45 | * |
| 69 | (Trans-racemic) | 458 | 4.00 | * |
| 70 | (Trans-racemic) | 420.24 | 4.27 | * |
| 71 | (Trans-racemic) |  |  | * |
| 72 | (Racemic) | 400.25 | 4.02 | * |
| 73 | (Trans-racemic) |  |  | * |
| 74 | (Trans-racemic) | 482.21 | 4.24 | * |
| 75 | (Trans-racemic) |  |  | * |
| 76 | (Trans-racemic) |  |  | * |
| 77 | (Trans-racemic) |  |  | * |
| 78 | (Trans-racemic) | 484.19 | 3.98 | * |
| 79 | (Trans-racemic) | 468.24 | 4.25 | * |
| 80 | (Trans-racemic) | 454 | 4.07 | * |
| 81 | (Trans-racemic) | 454 | 4.07 | * |
| 82 | (Trans-racemic) | 468 | 4.32 | * |
| 83 | (Trans-racemic) | 454 | 4.05 | * |
| 84 | (Trans-racemic) | 454 | 4.20 | * |
| 85 | (Trans-racemic) | 404 | 2.06 | * |
| 86 | (Trans-racemic) | 406 | 2.13 | * |
| 87 | (Trans-racemic) | 446 | 2.35 | * |
| 88 | (Trans-racemic) | 440 | 2.03 | * |
| 89 | (Trans-racemic) | 454 | 2.08 | * |
| 90 | (Trans-racemic) | 454 | 2.08 | * |
| 91 | (Trans-racemic) | 454 | 2.10 | * |
| 92 | (Trans-racemic) | 458 | 2.05 | * |
| 93 | (Trans-racemic) | 454 | 2.16 | * |
| 94 | (Trans-racemic) | 468 | 2.23 | * |
| 95 |  |  |  | ***** |
| 96 |  |  |  | ***** |
| 97 |  |  |  | ***** |
| 98 |  |  |  | ***** |
| 99 |  |  |  | ***** |
| 100 |  | 555.3 | 2.46 | **** |
| 101 |  | 569.3 | 2.59 | ***** |
| 102 |  | 583.3 | 2.66 | **** |
| 103 |  | 583.3 | 2.68 | ***** |
| 104 |  | 609.3 | 2.83 | ***** |
| 105 |  | 613.3 | 2.58 | **** |
| 106 |  | 625.3 | 2.56 | *** |
| 107 |  | 454.3 [M − H] | 3.61 | ***** |
| 108 |  | 484.3 | 3.93 | **** |
| 109 |  | 510.3 | 4.19 | **** |
| 110 |  | 514.4 | 3.69 | **** |
| 111 |  | 568.3 | 4.43 | ***** |
| 112 |  | 595.3 | 2.94 | ***** |
| 113 |  | 579.4 | 2.89 | ***** |
| 114 |  | 551.4 | 2.91 | *** |
| 115 |  | 623.2 | 2.99 | ***** |

TABLE 4-continued

| Compound | Stereochemistry | LCMS [MH+] | LCMS Retention Time (min) | ELISA EC$_{50}$ uM |
|---|---|---|---|---|
| 116 | | 524.4 | 4.34 | ***** |
| 117 | | 566.5 [M − H] | 4.36 | ***** |
| 118 | | 523.5 | 3.38 | *** |
| 119 | | 523.5 | 3.38 | ** |
| 120 | | 515.4 | 2.47 | ** |
| 121 | | 516.4 | 3.30 | *** |
| 122 | | 479.4 | 3.27 | ** |
| 123 | | 460.3 | 2.35 | ** |
| 124 | | 492.3 | 2.34 | *** |
| 125 | | 471.3 | 2.42 | ** |
| 126 | | 472.3 | 3.25 | ** |
| 127 | | 539.3 | 3.89 | ***** |
| 128 | | 520.3 | 2.69 | **** |
| 129 | | 552.4 | 2.60 | **** |
| 130 | | 531.3 | 3.00 | *** |
| 131 | | 532.3 | 3.69 | **** |
| 132 | | 476.3 | 2.67 | *** |
| 133 | | 508.4 | 2.55 | *** |
| 134 | | 487.3 | 2.97 | **** |
| 135 | | 488.3 | 3.64 | *** |
| 136 | | 513.24 | 3.66 | *** |
| 137 | | | | **** |
| 138 | | 554.16 | 3.94 | ***** |
| 139 | | 576.21 | 3.81 | **** |
| 140 | | 576.22 | 3.78 | ***** |
| 141 | | 577.26 | 3.43 | ***** |
| 142 | | 548.23 | 3.78 | ***** |
| 143 | | 526.24 | 3.79 | **** |
| 144 | | 540.29 | 3.86 | **** |
| 145 | | 554.32 | 3.91 | ***** |
| 146 | | 544.23 | 3.76 | ***** |
| 147 | | 499.28 | 3.34 | *** |
| 148 | | 566.5 [M − H] | 4.33 | ** |
| 149 | | 647.97 | 3.27 | ***** |
| 150 | | 581.56 | 2.85 | ***** |
| 151 | | 595.47 | 2.87 | ***** |
| 152 | | 638.47 | 2.74 | ***** |
| 153 | | 597.43 | 2.78 | **** |
| 154 | | 583.44 | 2.85 | ***** |
| 155 | | 569.44 | 2.83 | ***** |
| 156 | | 643.48 | 2.88 | **** |
| 157 | | 613.42 | 2.86 | *** |
| 158 | | 599.44 | 2.83 | ***** |
| 159 | | 610.47 | 2.65 | ***** |
| 160 | | 578.40 | 2.82 | **** |
| 161 | | 577.51 | 3.83 | **** |
| 162 | | 584.46 | 4.33 | ***** |
| 163 | | 584.45 | | ***** |
| 164 | | 552.41 | 4.18 | *** |
| 165 | | 552.37 | 4.31 | ***** |
| 166 | | 536.41 | 4.13 | **** |
| 167 | | 536.43 | 4.16 | ***** |
| 168 | | 534.43 | 4.14 | ***** |
| 169 | | 532.44 | 4.18 | *** |
| 170 | | 532.45 | 4.23 | ***** |
| 171 | | 532.39 | 4.24 | ***** |
| 172 | | | | ***** |
| 173 | | | | ***** |
| 174 | | 570.3 | 4.36 | *** |
| 175 | | | | ***** |
| 176 | | | | ***** |
| 177 | | | | *** |
| 178 | | | | *** |
| 179 | | | | ***** |
| 180 | | | | ***** |
| 181 | | | | ***** |
| 182 | | | | ***** |
| 183 | | | | *** |
| 184 | | 579.52 | 3.48 | ***** |
| 185 | | 525 | 4.49 | ***** |
| 186 | | | | ***** |
| 187 | | 525 | | * |
| 188 | | 614.51 | | ***** |
| 189 | | 649.36 | | **** |
| 190 | | 663.37 | | **** |
| 191 | | 563.80 | | ***** |
| 192 | | 665.35 | | ***** |
| 193 | | 651.39 | | **** |
| 194 | | 637.38 | | **** |
| 195 | | 596.41 | | ***** |
| 196 | | 682.31 | | ***** |
| 197 | | 667.36 | | **** |
| 198 | | 678.39 | | ***** |
| 199 | | 646.32 | | ***** |
| 200 | | 560.21 | | **** |
| 201 | | 564.23 [M − H] | | ***** |

Wherein:
1 star, >1 uM (1000 nM)
2 stars, 0.2 to 1 uM (200 nM to 1000 nM)
3 stars, 0.04 uM to o.2 uM (40 nM to 200 nM)
4 stars, 0.008 uM to 0.04 uM (8 nM to 40 nM)
5 stars, <0.008 uM (<8 nM)

Example 3

Compounds of the Invention Inhibit VEGF Expression and Tumor Growth in an In Vivo Tumor Growth PD Model Compounds of the invention also show activity in the following pharmacodynamic model that assesses intratumor VEGF levels. Briefly, HT1080 cells (a human fibrosarcoma cell line) may be implanted subcutaneously in nude mice. After seven days, mice may be administrated compounds orally at a desired dosage range, e.g., 200 mg/kg/day, for seven days. The tumors may then be excised from mice and homogenized in Tris-HCl buffer containing proteinase inhibitors. Moulder et al., *Cancer Res.* 61(24):8887-95 (2001). Intratumor VEGF levels are subsequently measured using a human VEGF ELISA kit (R&D System). Protein concentrations of the homogenates are measured with a Bio-Rad Protein assay kit and intratumor VEGF levels are normalized to the protein concentrations.

Preferred compounds of the invention, when used for one week on a 100 mm$^3$ tumor, will generally inhibit tumor growth by at least 50%, as compared to the vehicle-treated control groups (data not shown).

Example 4

Compounds of the Invention do not Effect the Activity of PDE5

The compounds of the invention are tested to assess their effect on phosphodiesterase 5 (PDE5) activity. The effect on PDE5 activity is determined using the High-Efficiency Fluorescence Polarization Assay (HEFP) kit from Molecular Devices. The HEFP assay measures the activity of PDE-5 by using fluorescein-labeled derivatives of cGMP as a substrate. When hydrolyzed by PDE-5, fluorescein-labeled cGMP derivatives are able to bind to a binding reagent. The cGMP substrate:binding reagent complex results in a highly polarized fluorescent state.

Figure 2:
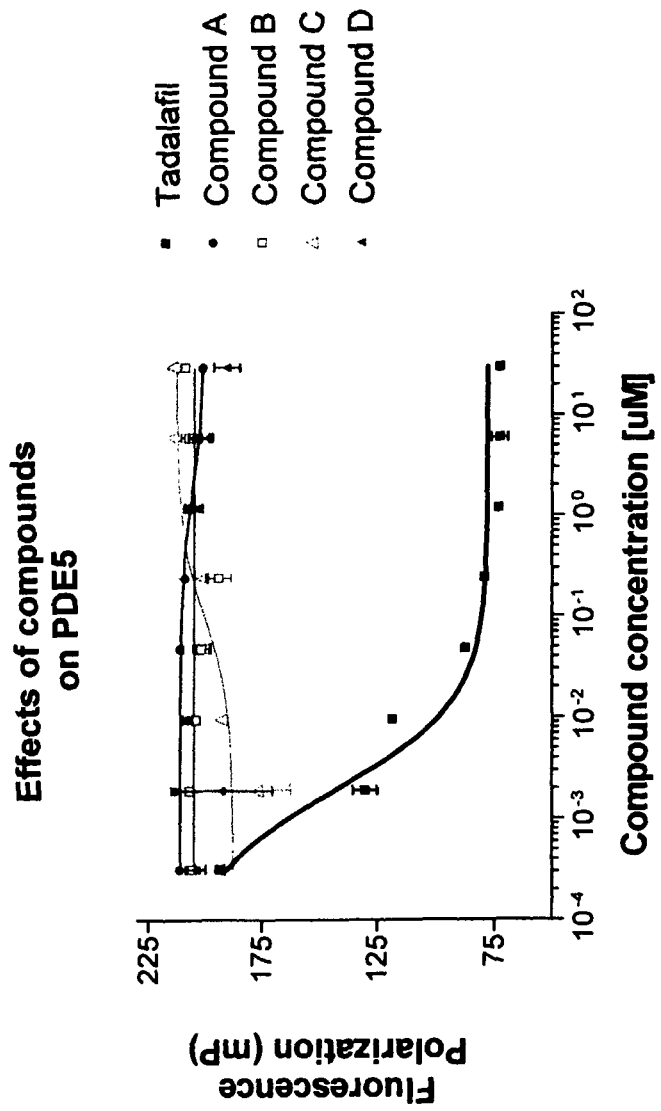
FIG. 2 illustrations that the activity of phosphdiesterase 5 (PDE-5) is not effected by certain compounds of the invention.

FIG. 2 shows the results of the compounds of the invention on PDE-5 activity. After combining recombinant PDE5 (Cal-BioChem) and the cGMP substrate, the mixture is incubated at room temperature for 45 minutes in the presence or absence of compounds or a positive control (Tadalafil). The reaction is stopped upon addition of the binding reagent. Fluorescence polarization is determined on a Viewlux using a setting recommended by the manufacturer. As is evident from FIG. 2, the compounds of the invention do not inhibit the activity of PDE-5 in comparison to the positive control.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed:

1. A compound having a structure selected from the group consisting of:

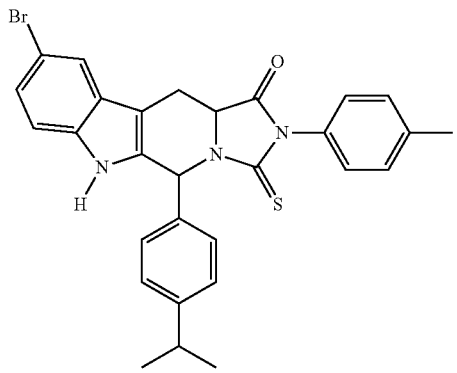

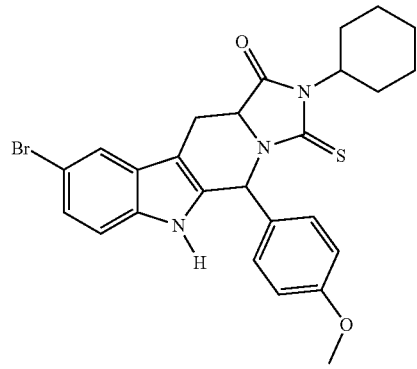

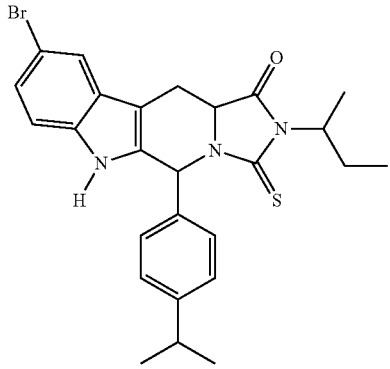

-continued

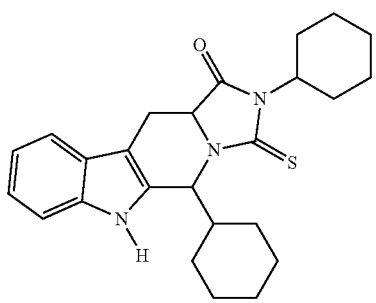

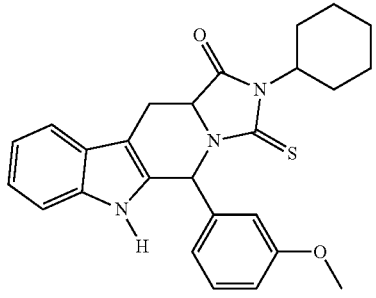

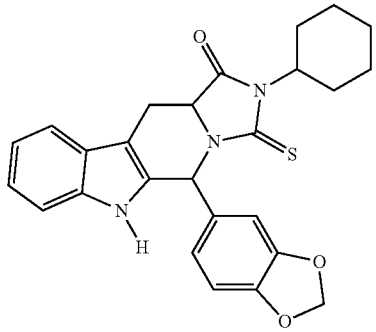

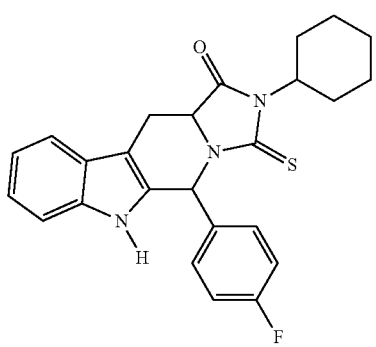

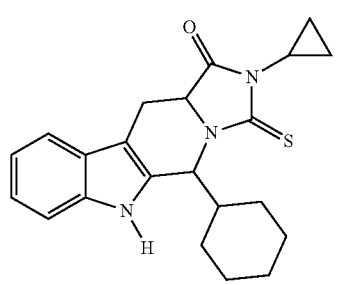

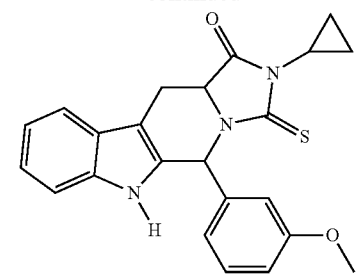
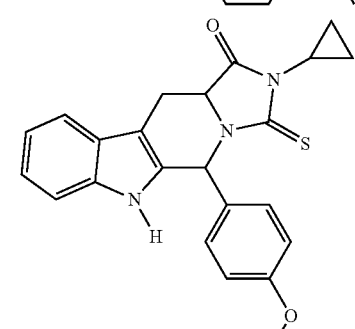
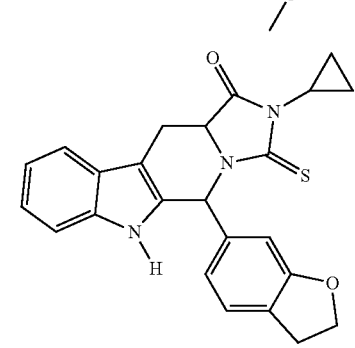
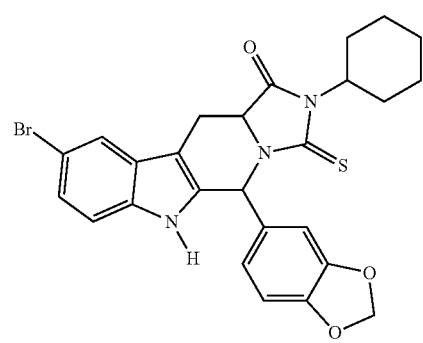
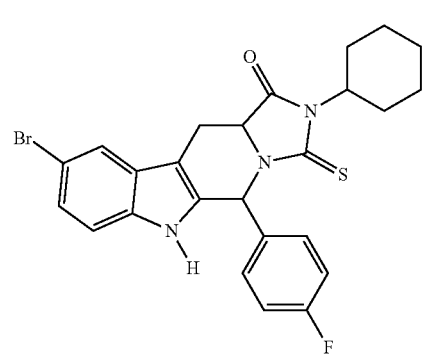
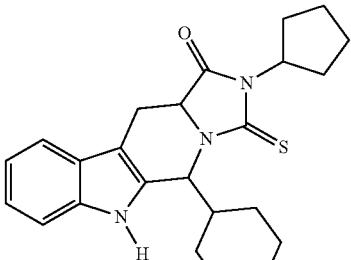
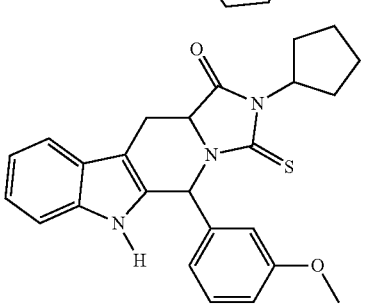
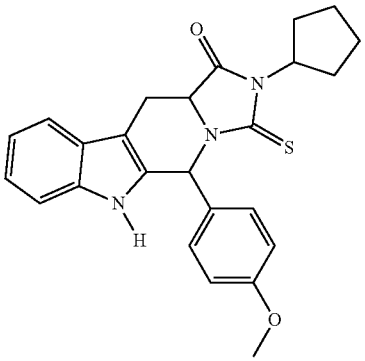
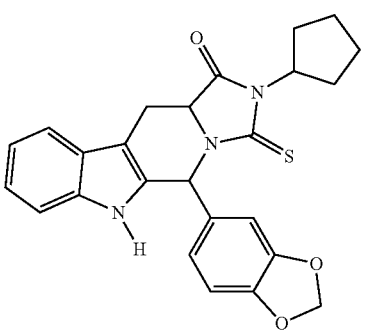
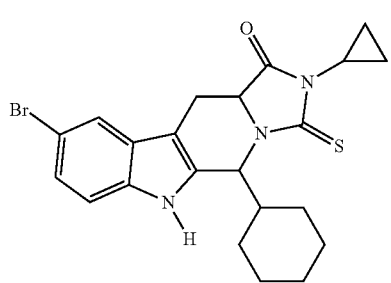

89
-continued
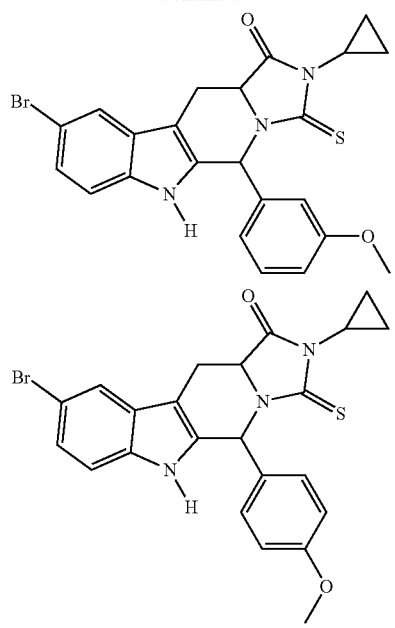
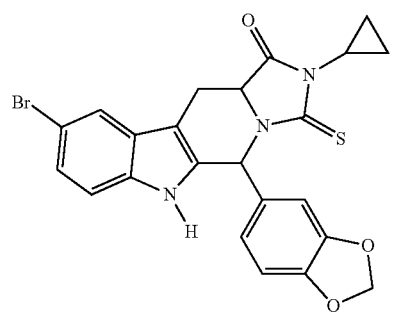
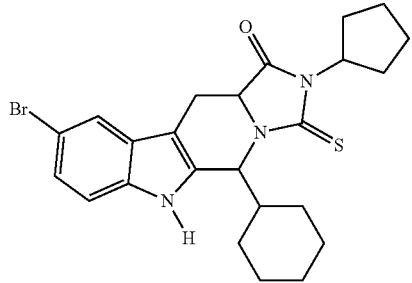
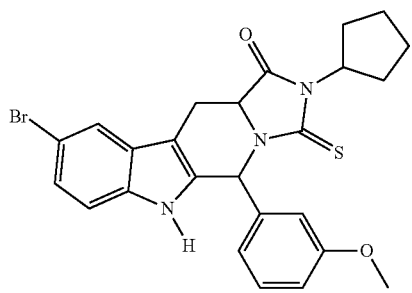
90
-continued
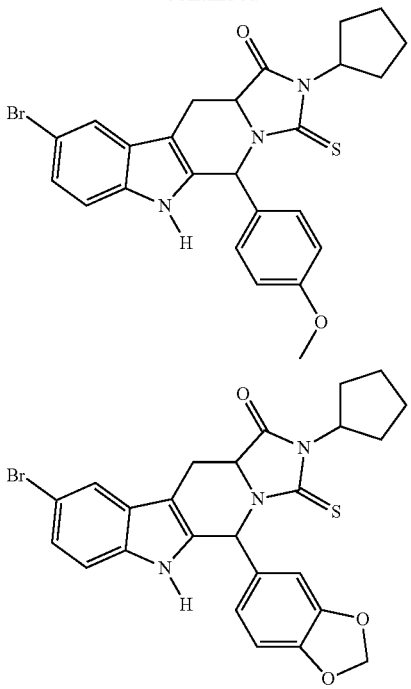
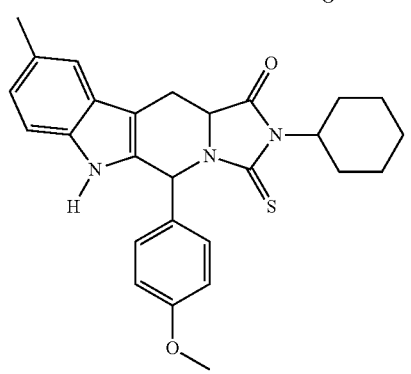
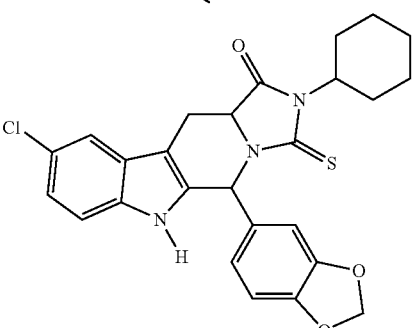
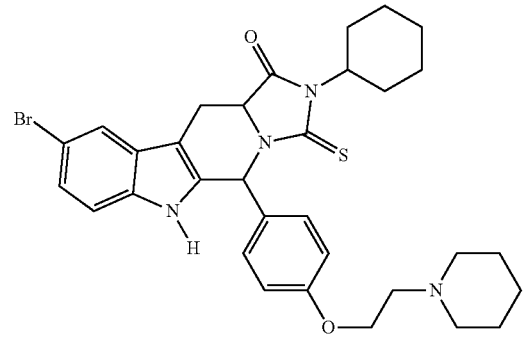

91
-continued
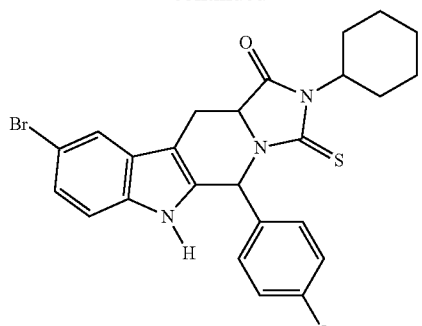
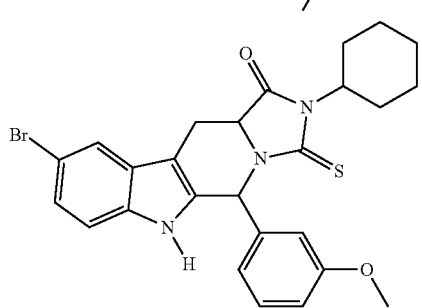
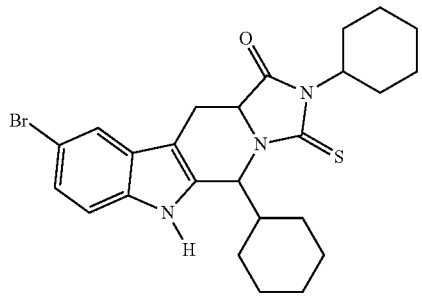
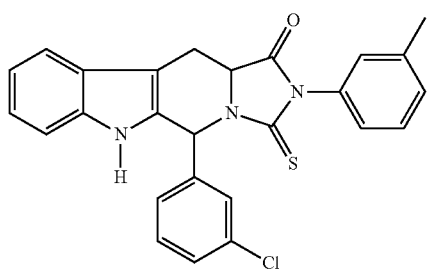
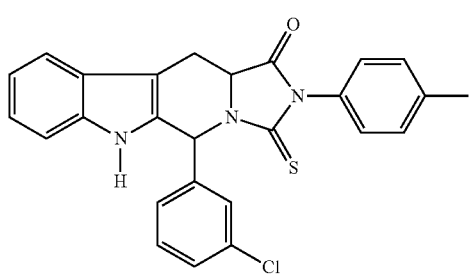
92
-continued
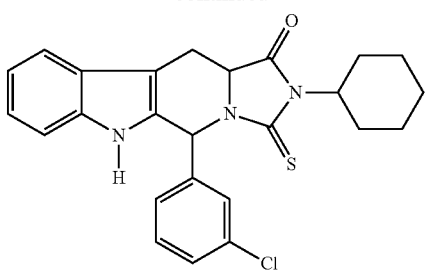
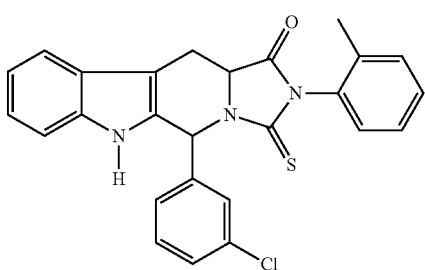
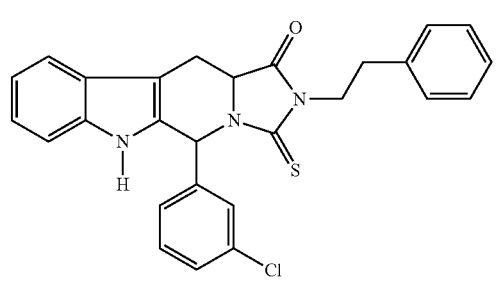
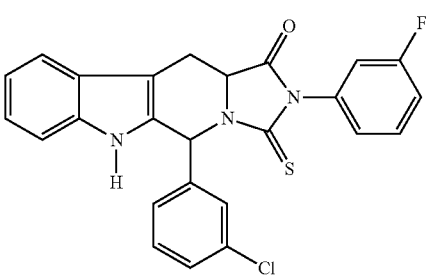
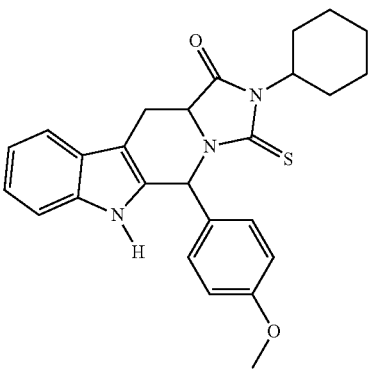

-continued
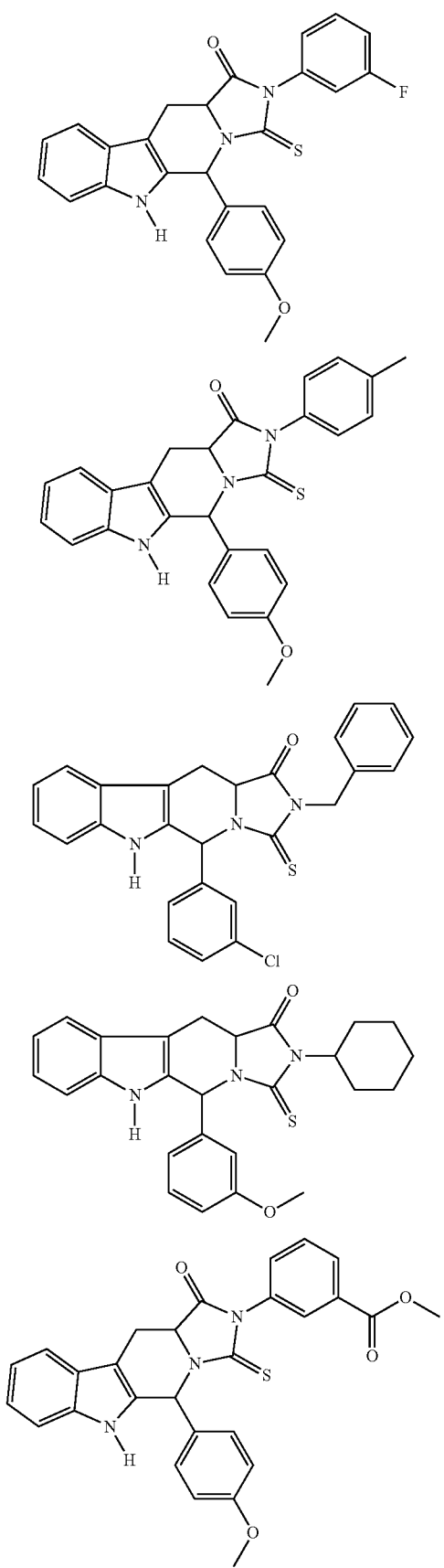
-continued
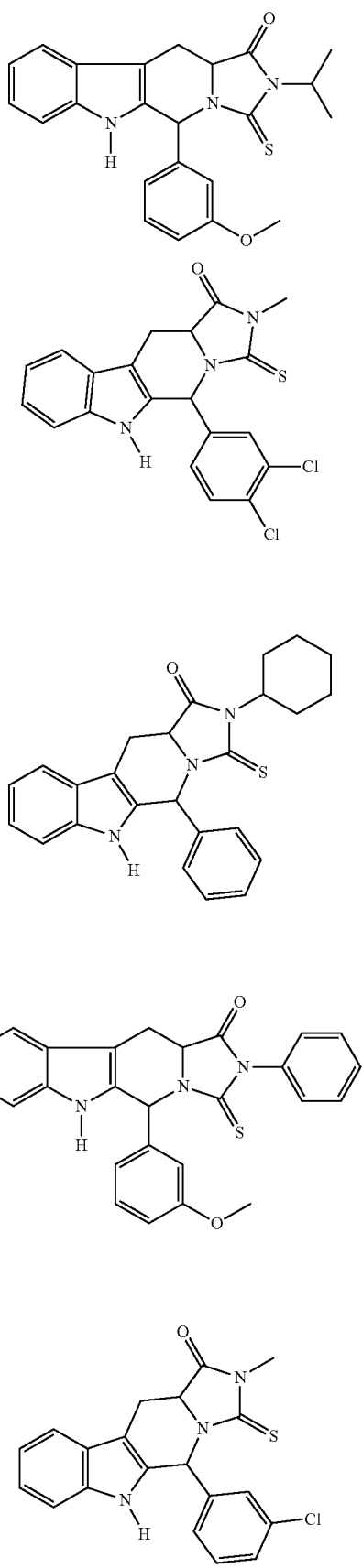

95
-continued
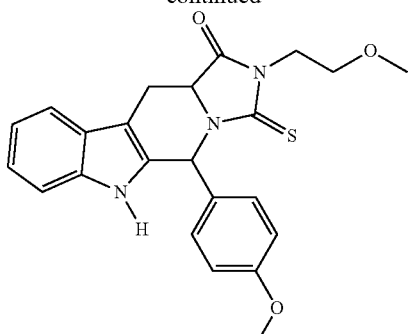
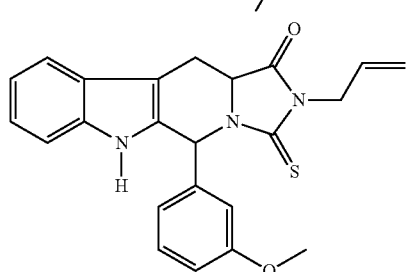
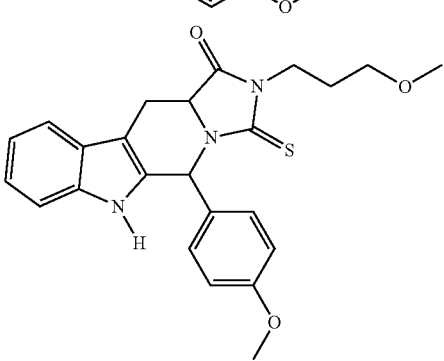
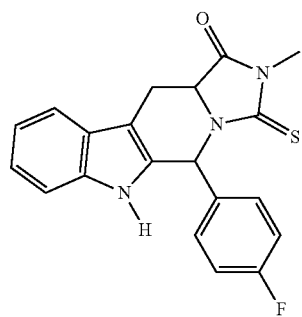
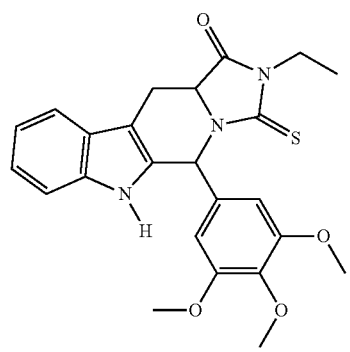
96
-continued
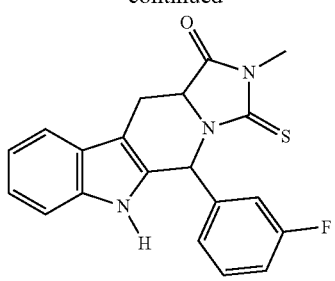
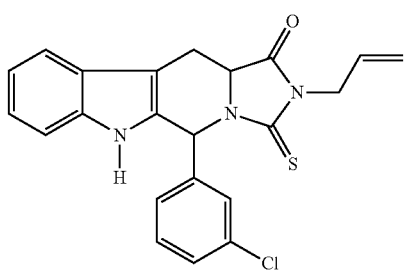
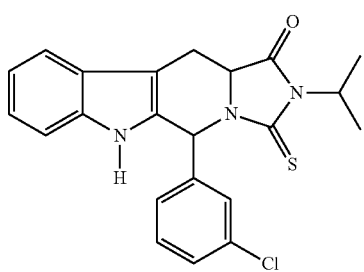
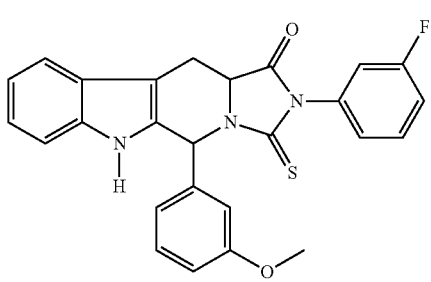
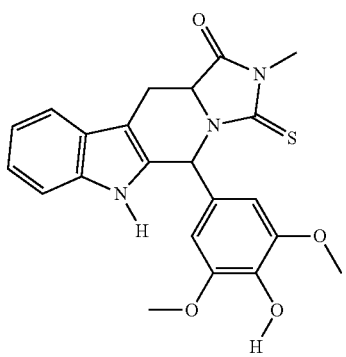

97
-continued
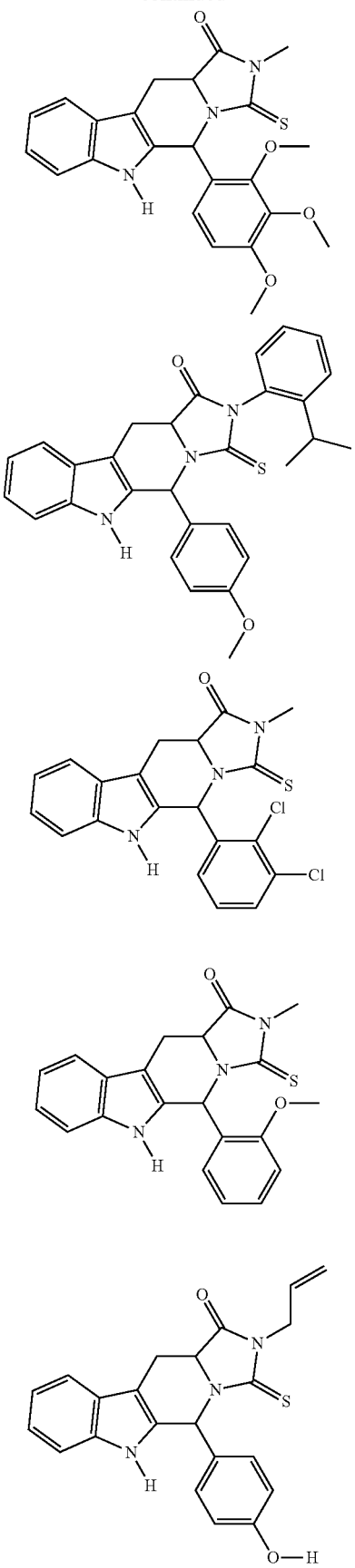
98
-continued
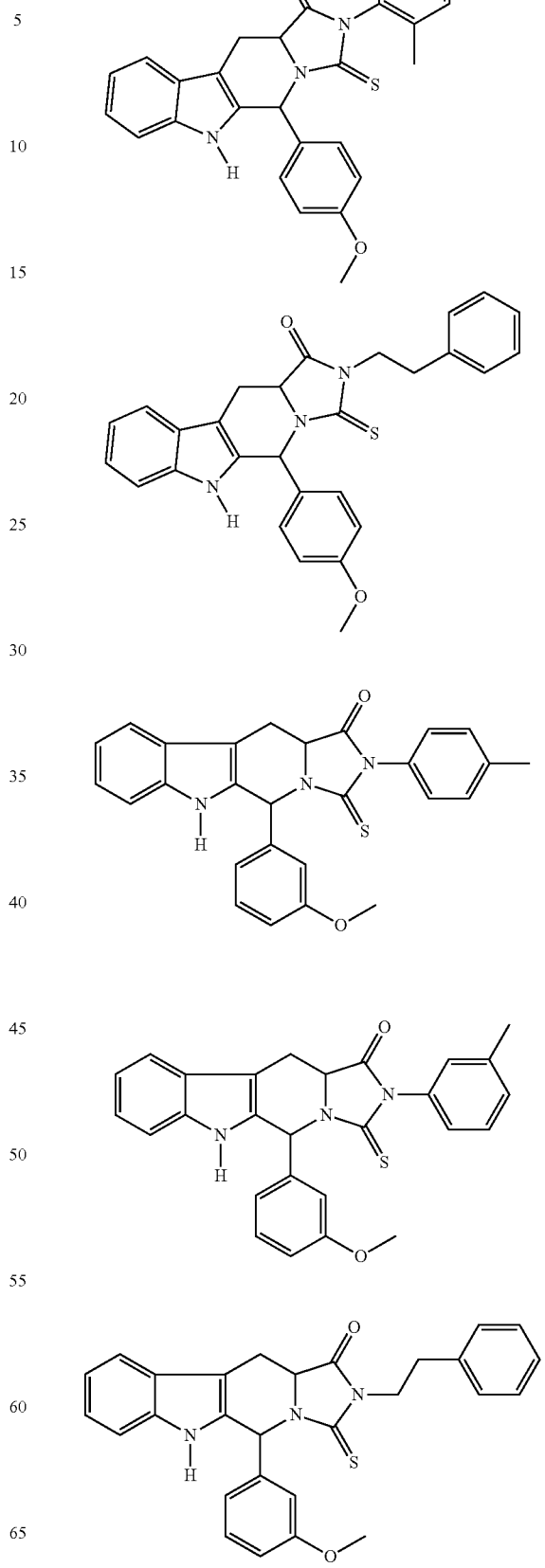

99
-continued
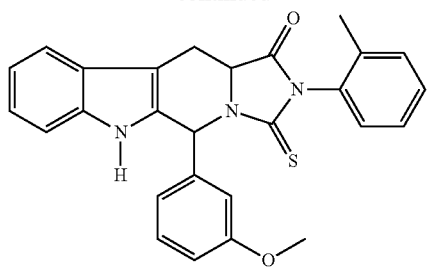
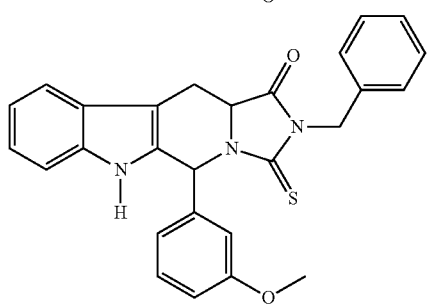
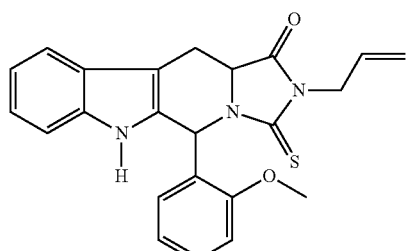
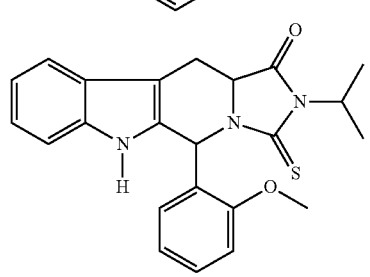
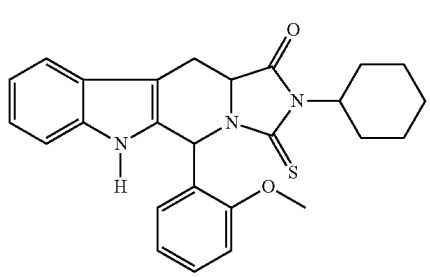
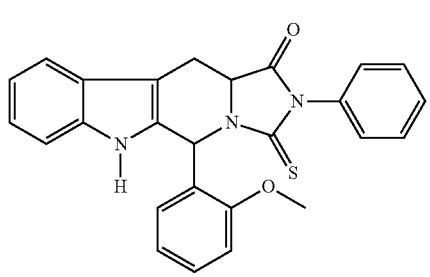
100
-continued
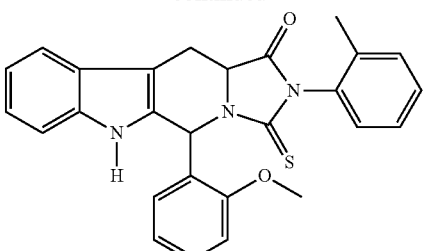
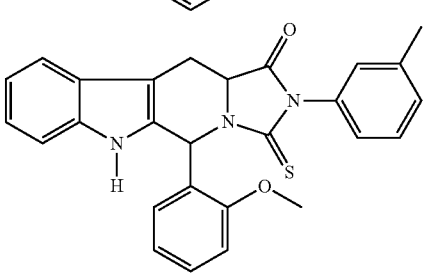
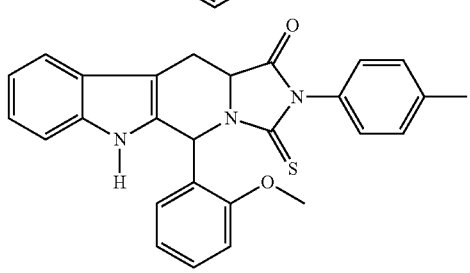
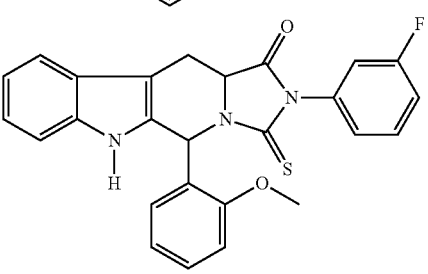
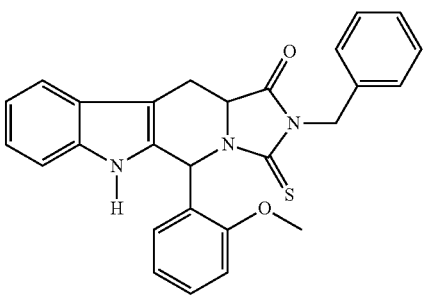
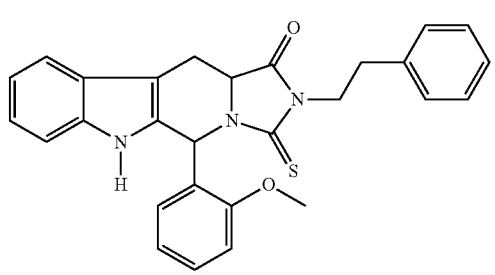

101
-continued
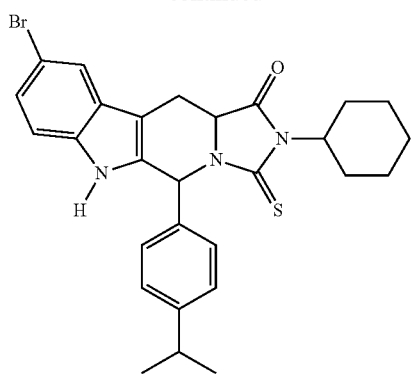
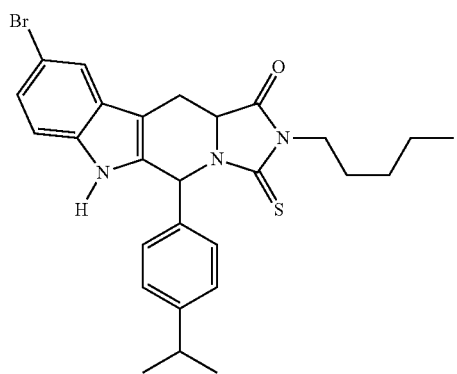
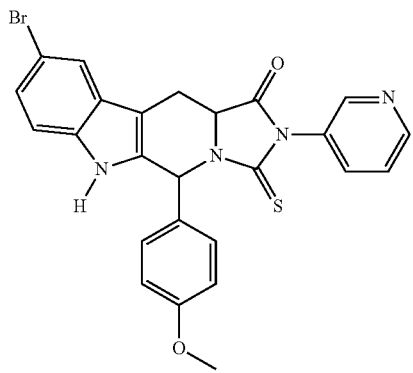
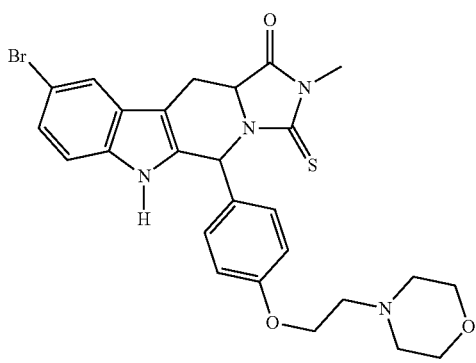
102
-continued
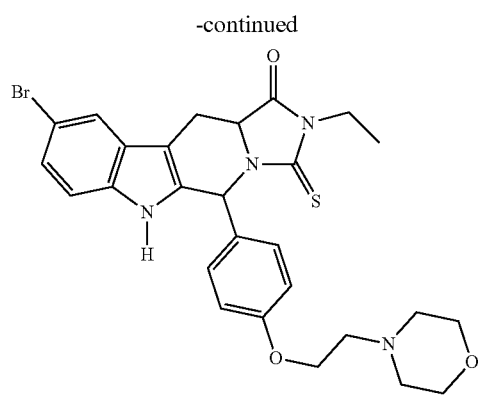
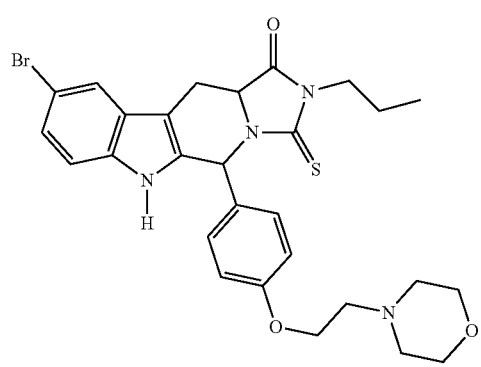
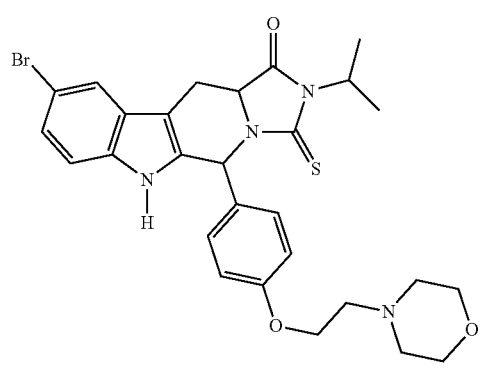
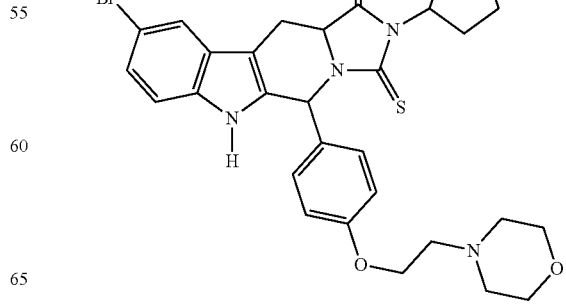

103
-continued
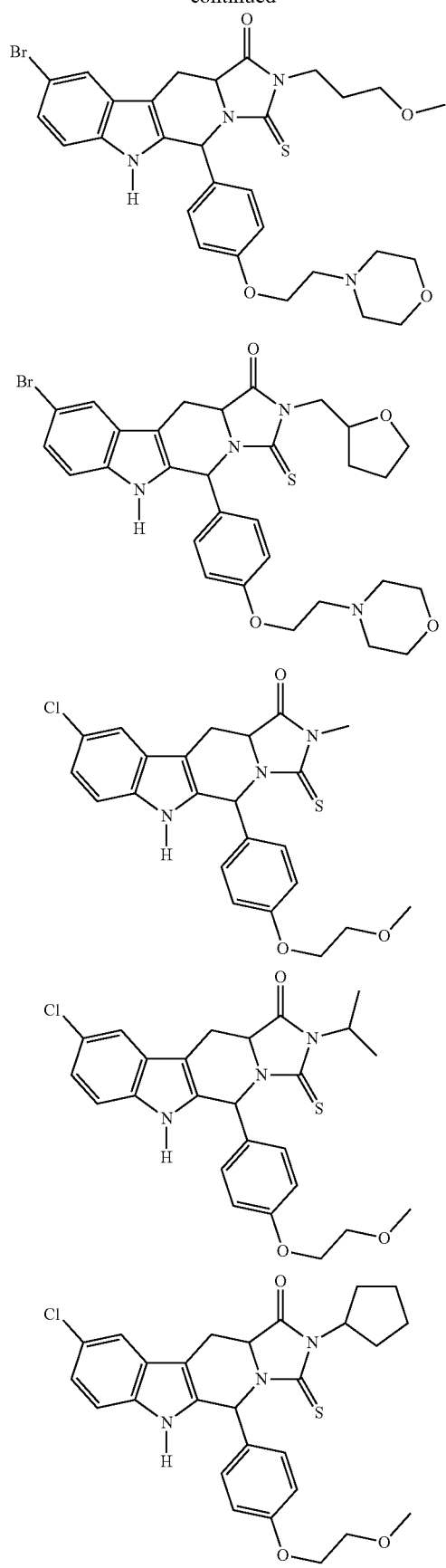
104
-continued
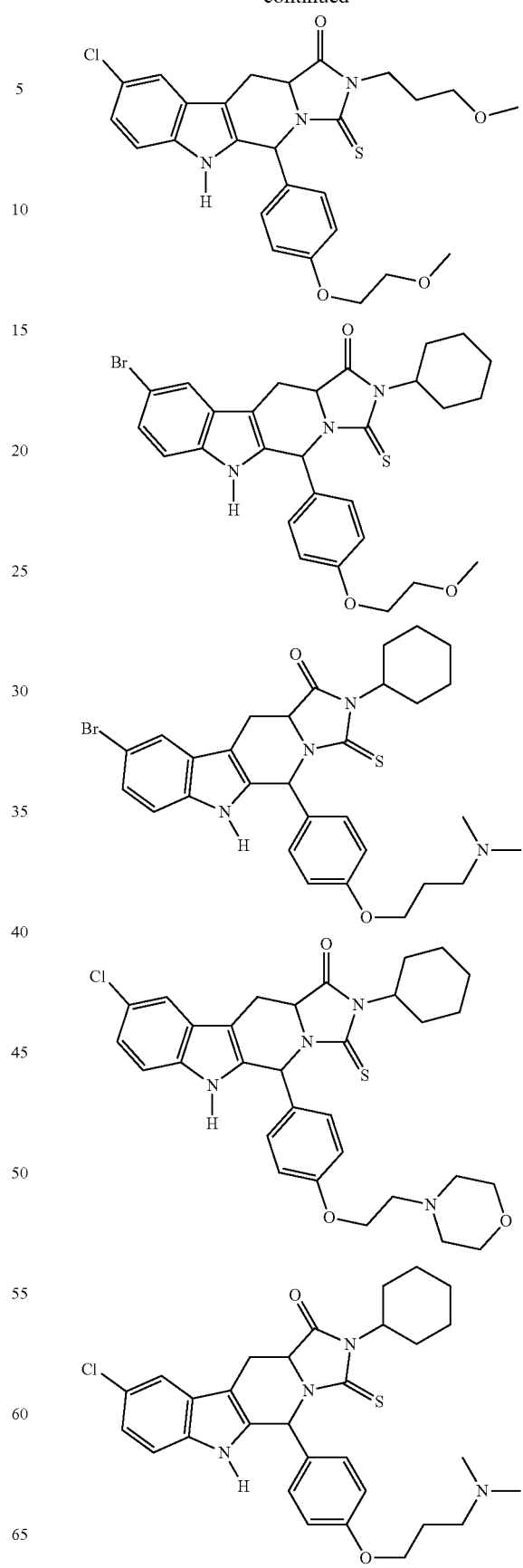

105
-continued
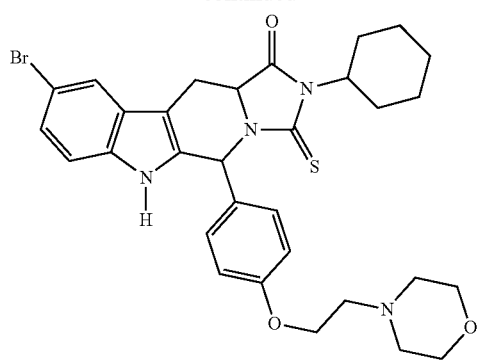
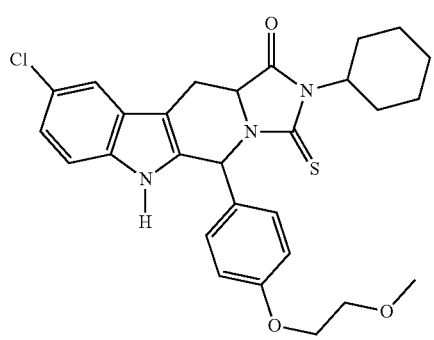
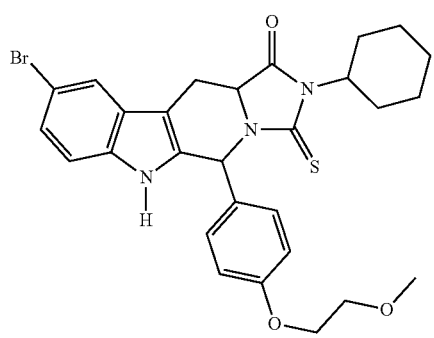
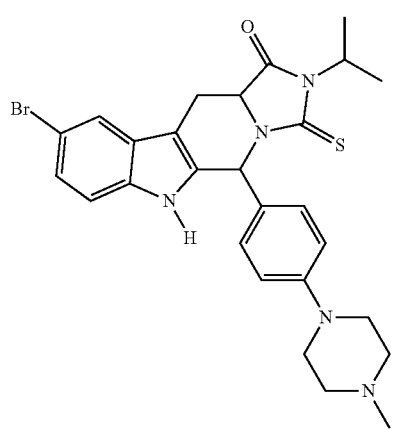
106
-continued
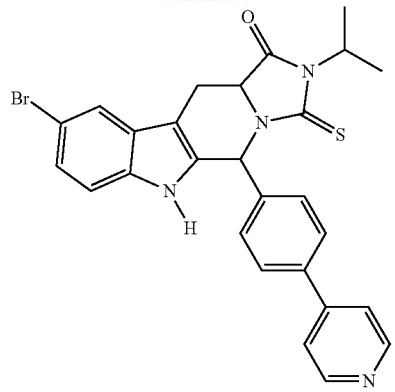
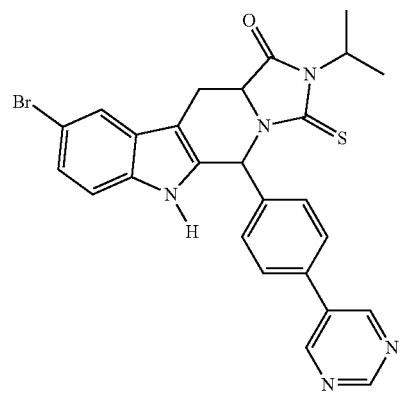
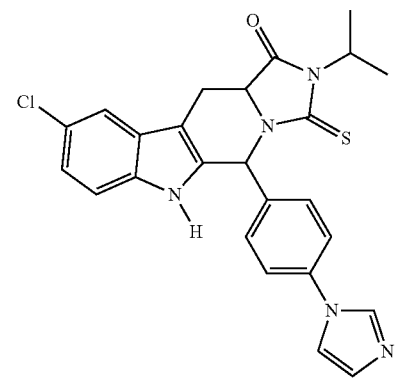
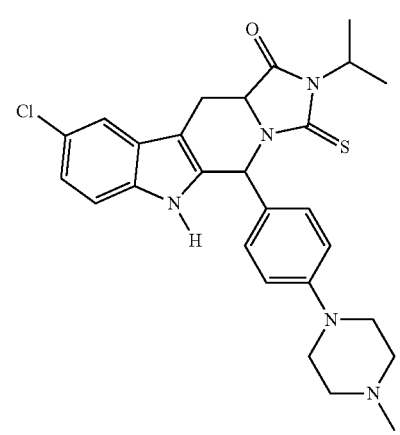

107
-continued
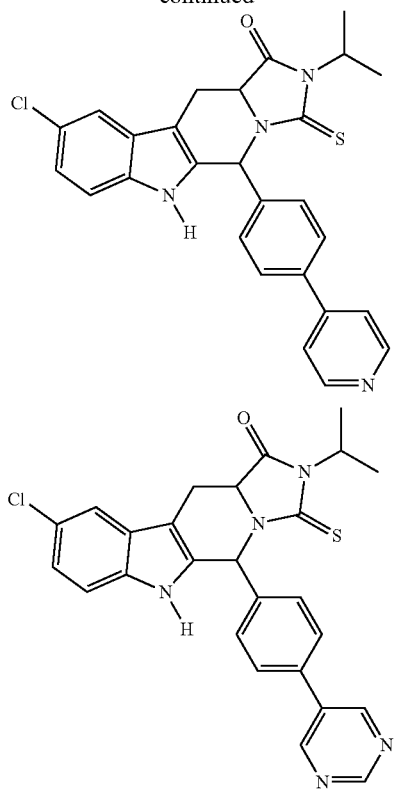
108
-continued
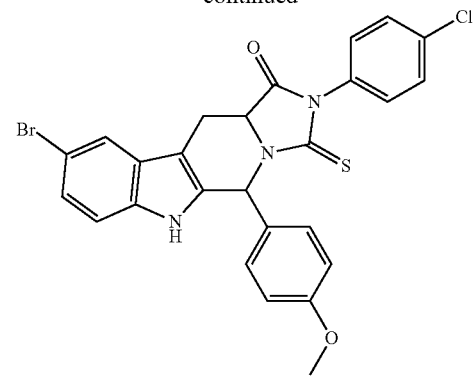
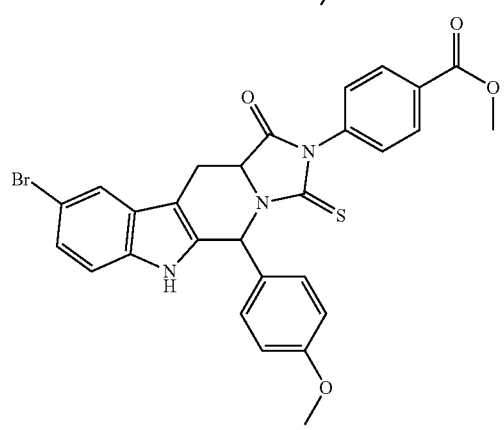
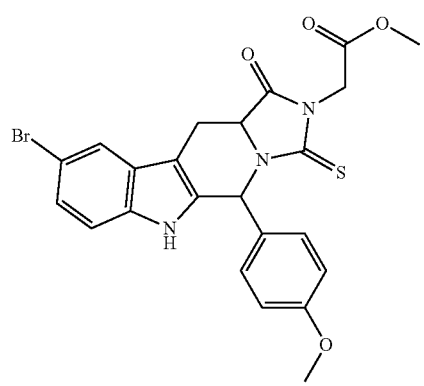
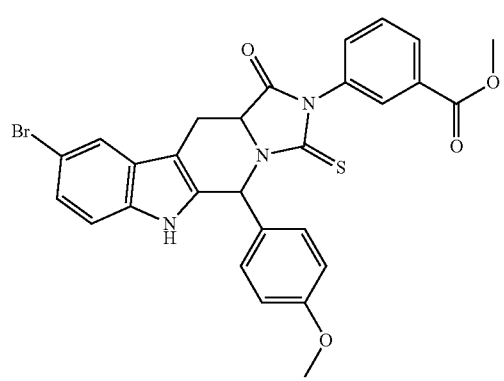
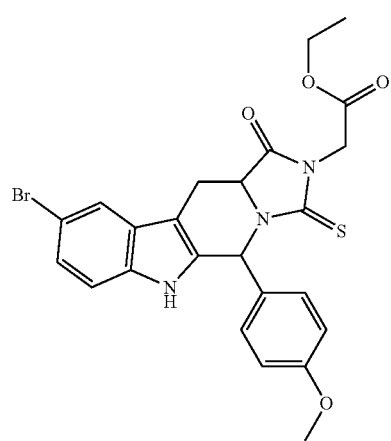

109
-continued
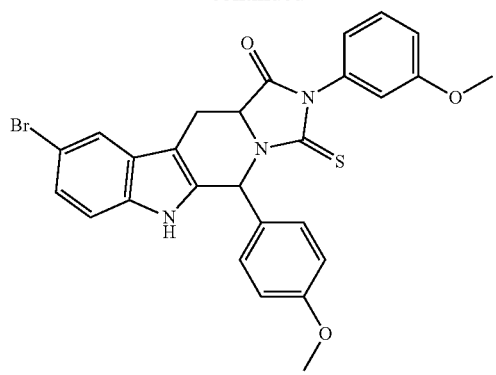
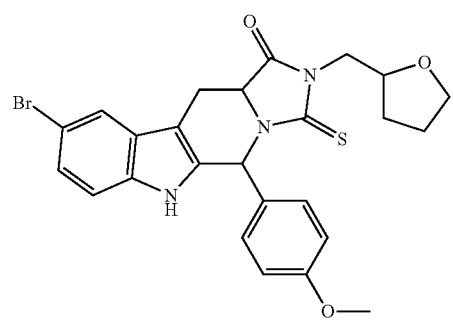
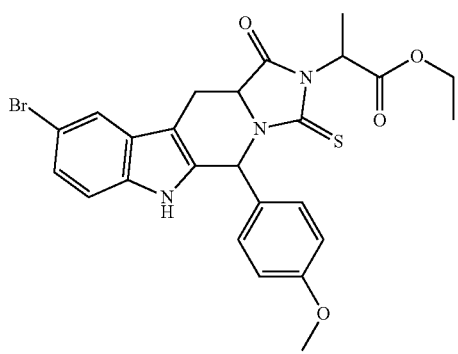
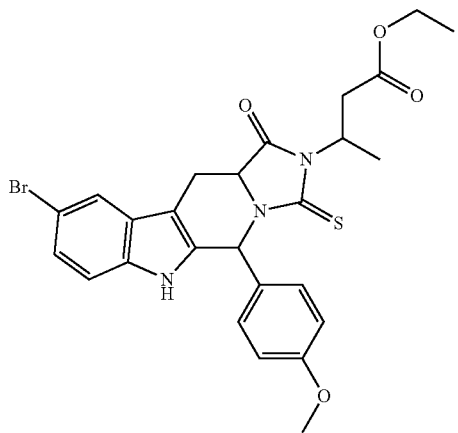
110
-continued
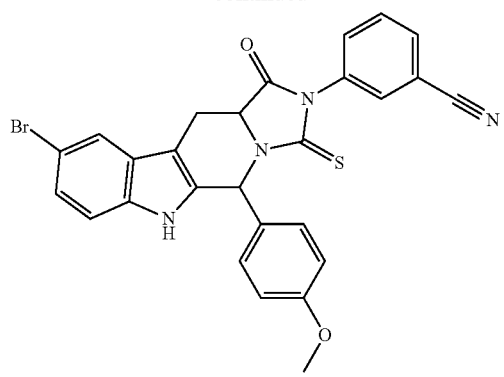
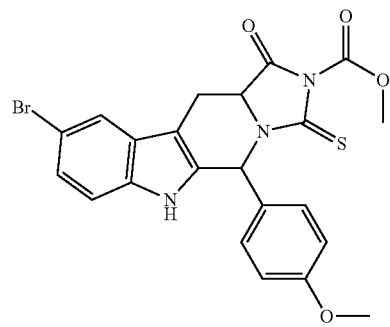
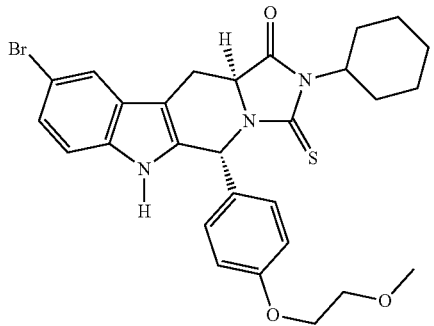
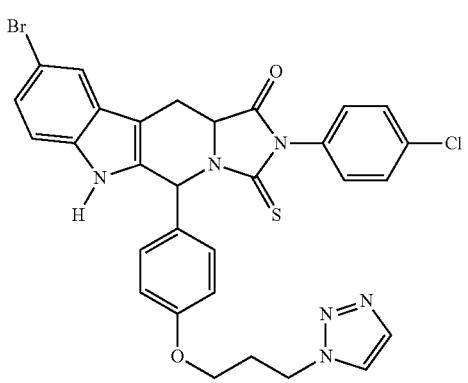

111
-continued
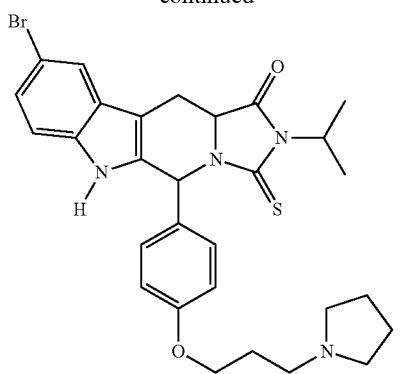
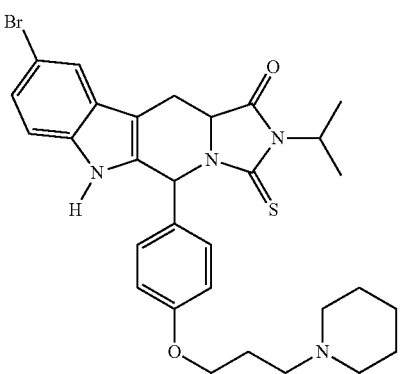
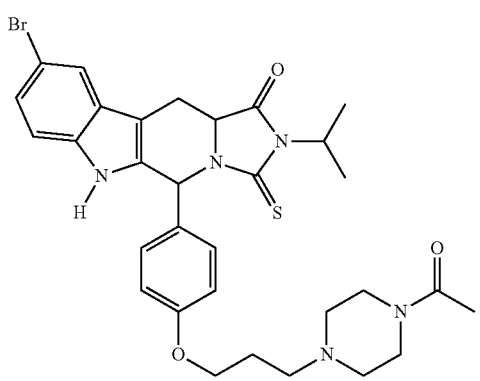
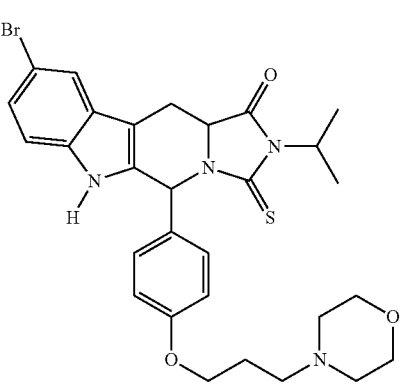
112
-continued
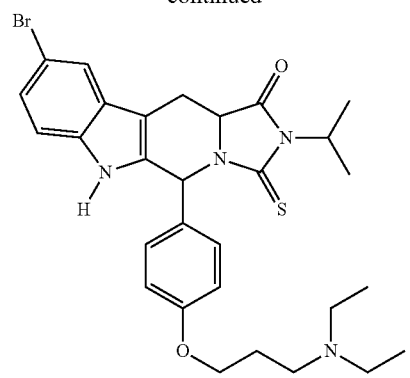
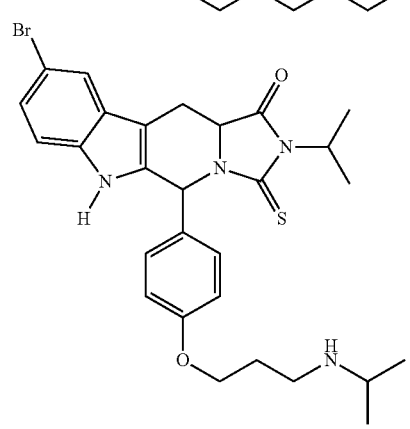
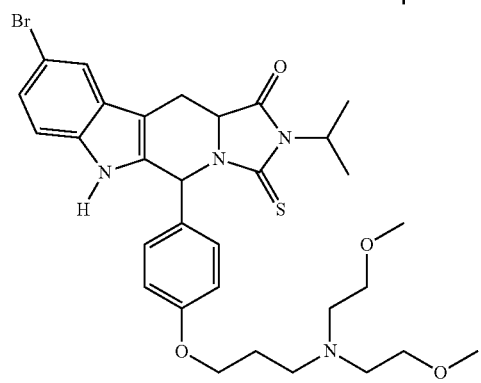
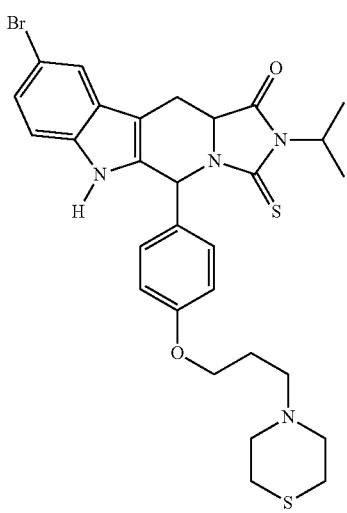

113
-continued
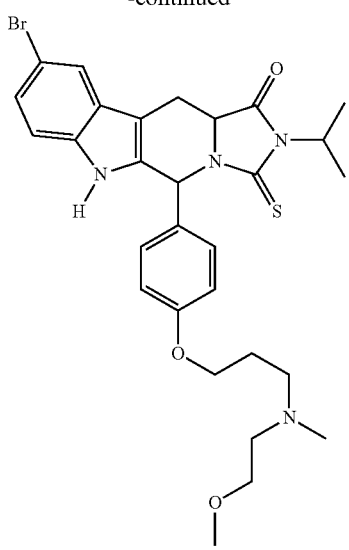
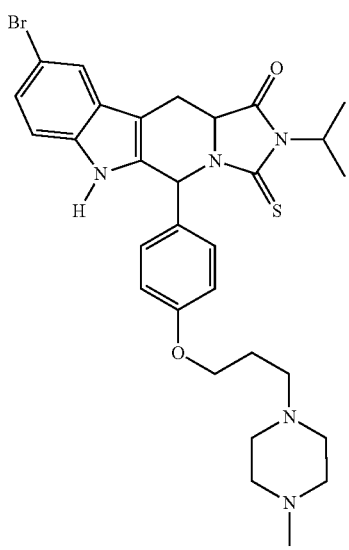
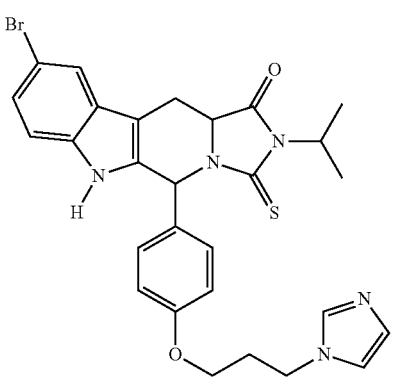
114
-continued
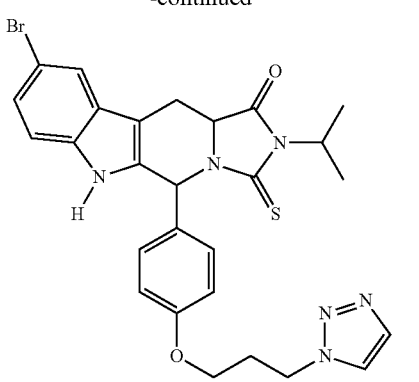
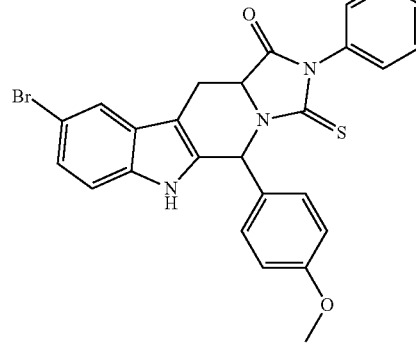
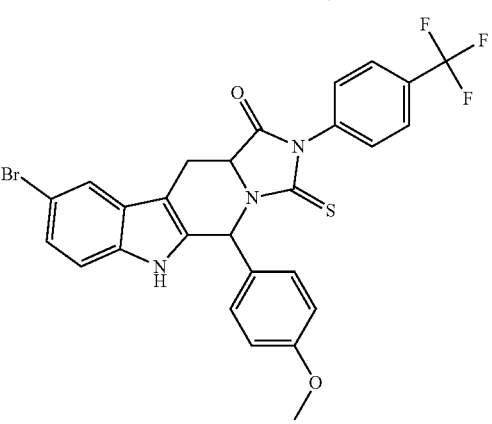
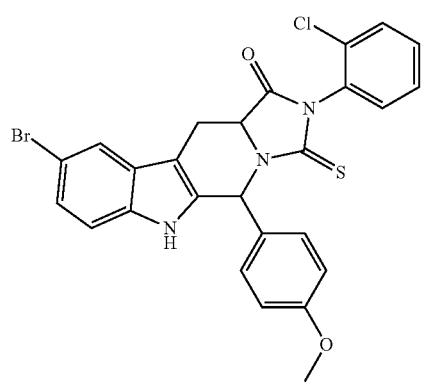

115
-continued
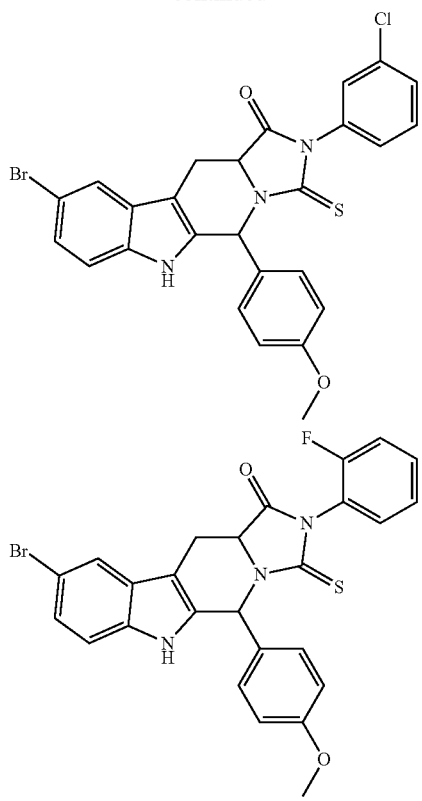
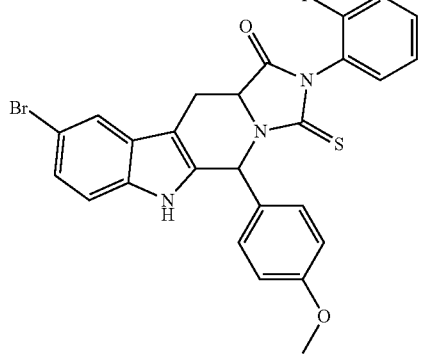
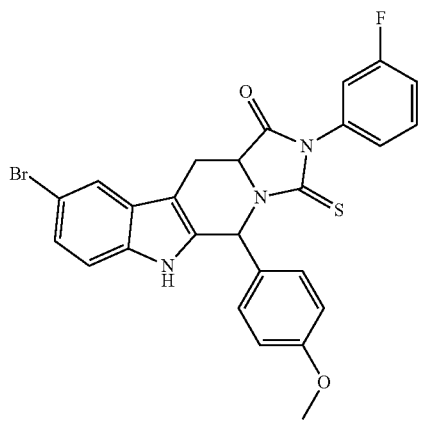
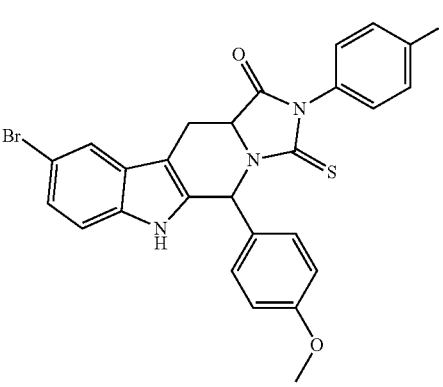
116
-continued
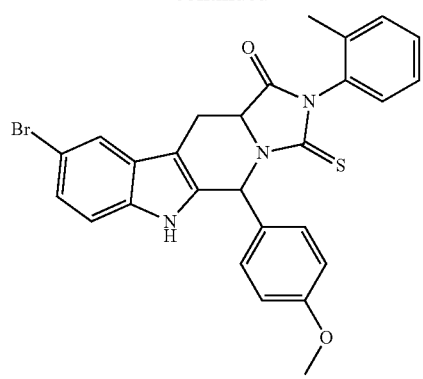
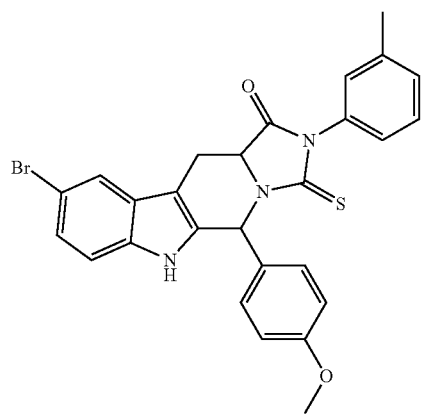
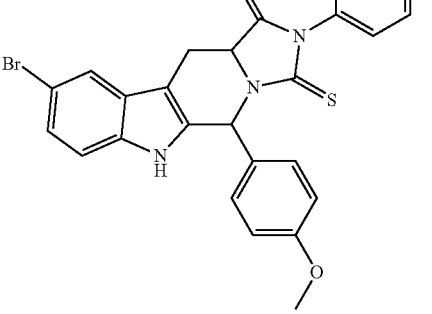
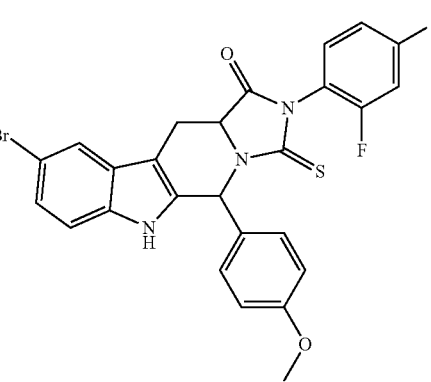

117
-continued
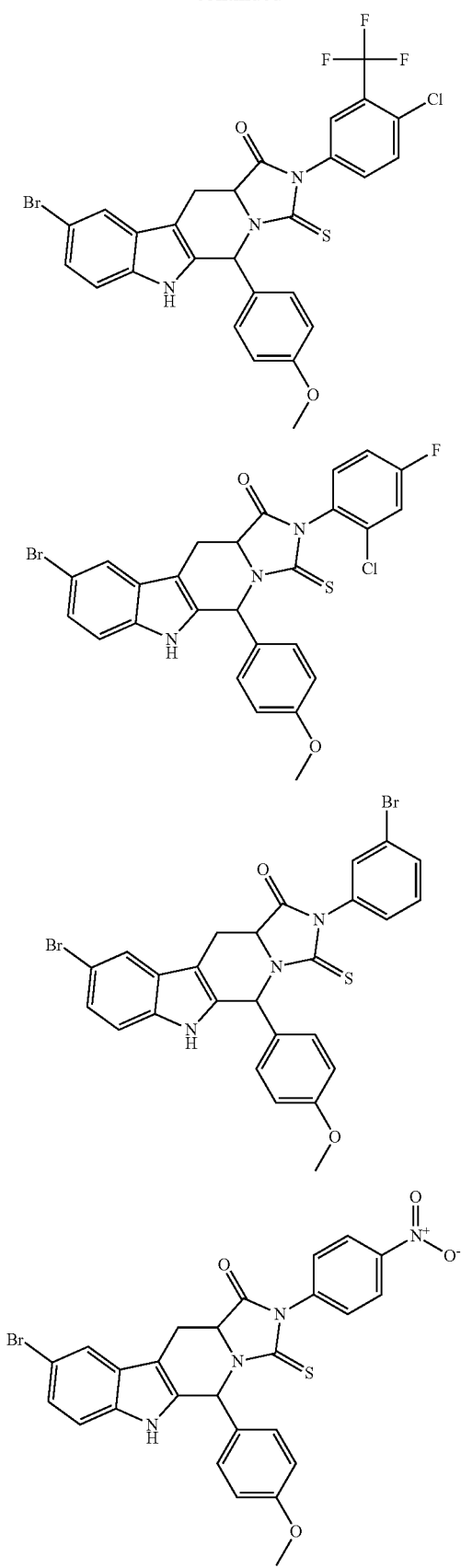
118
-continued
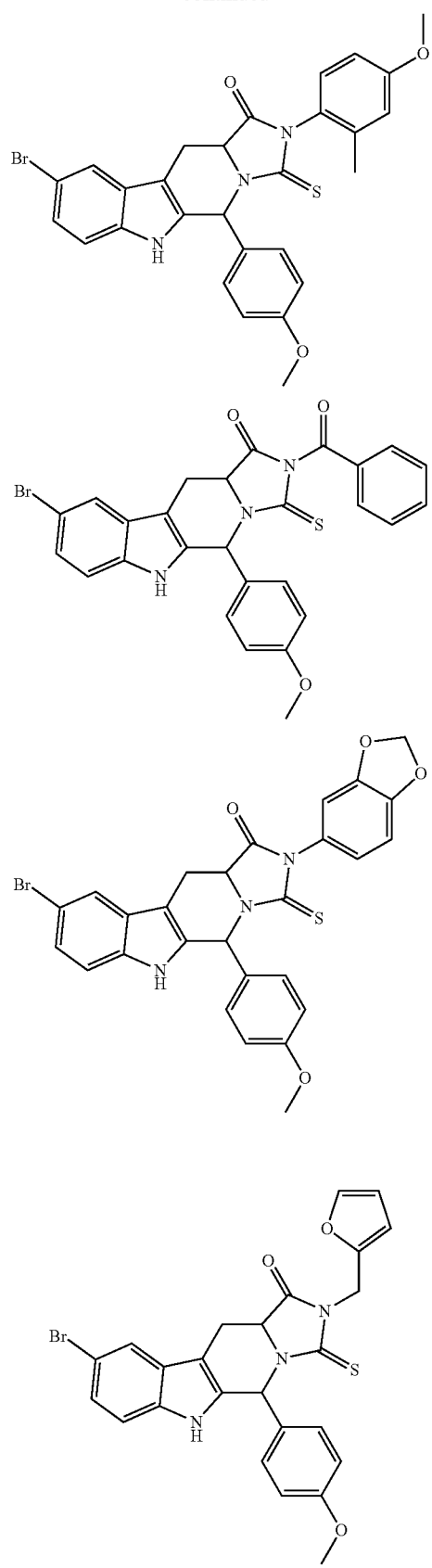

119
-continued
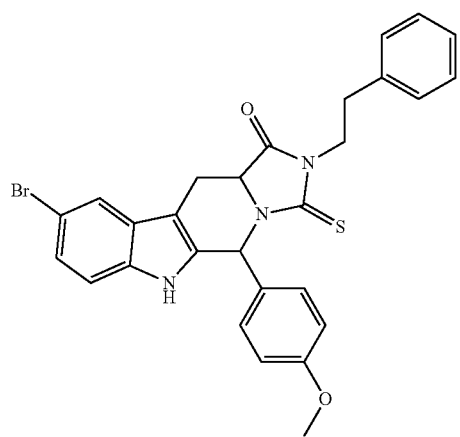
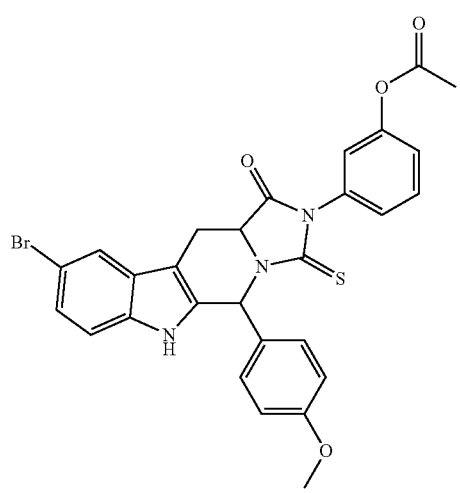
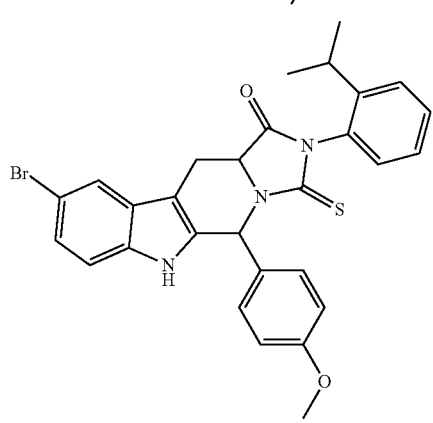
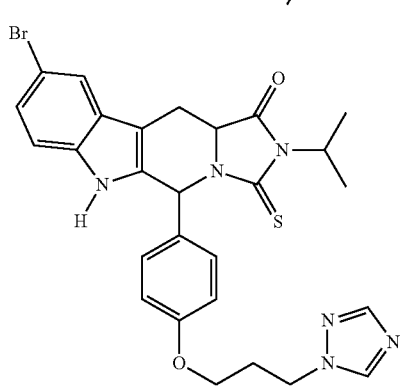
120
-continued
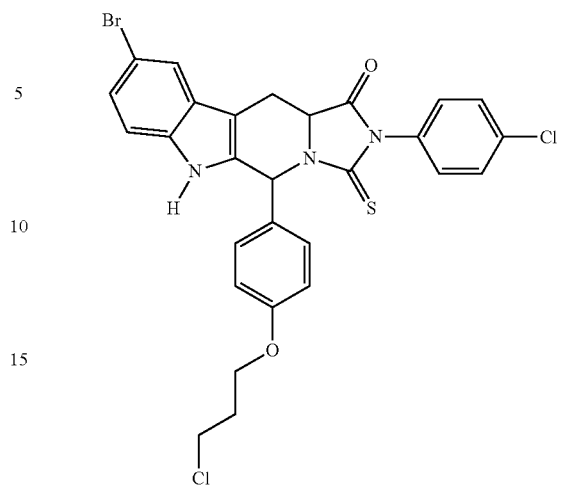
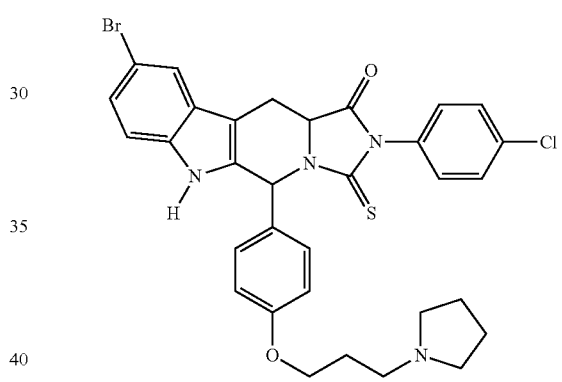
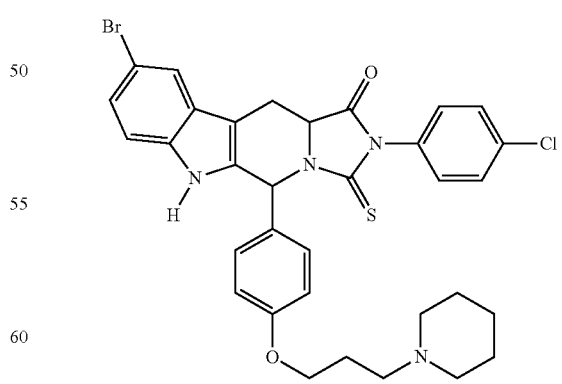

121
-continued
122
-continued
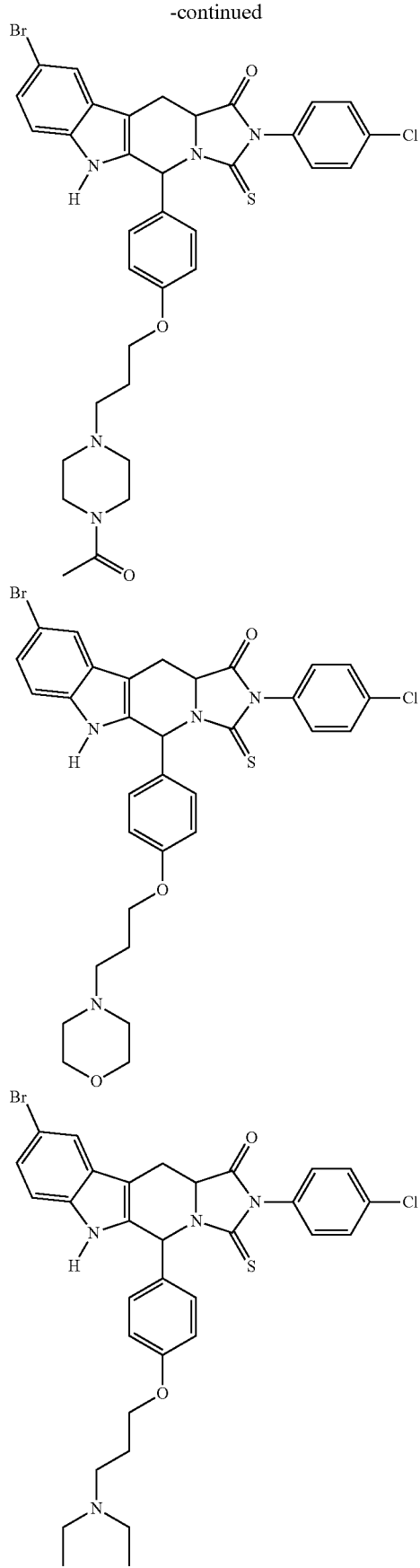
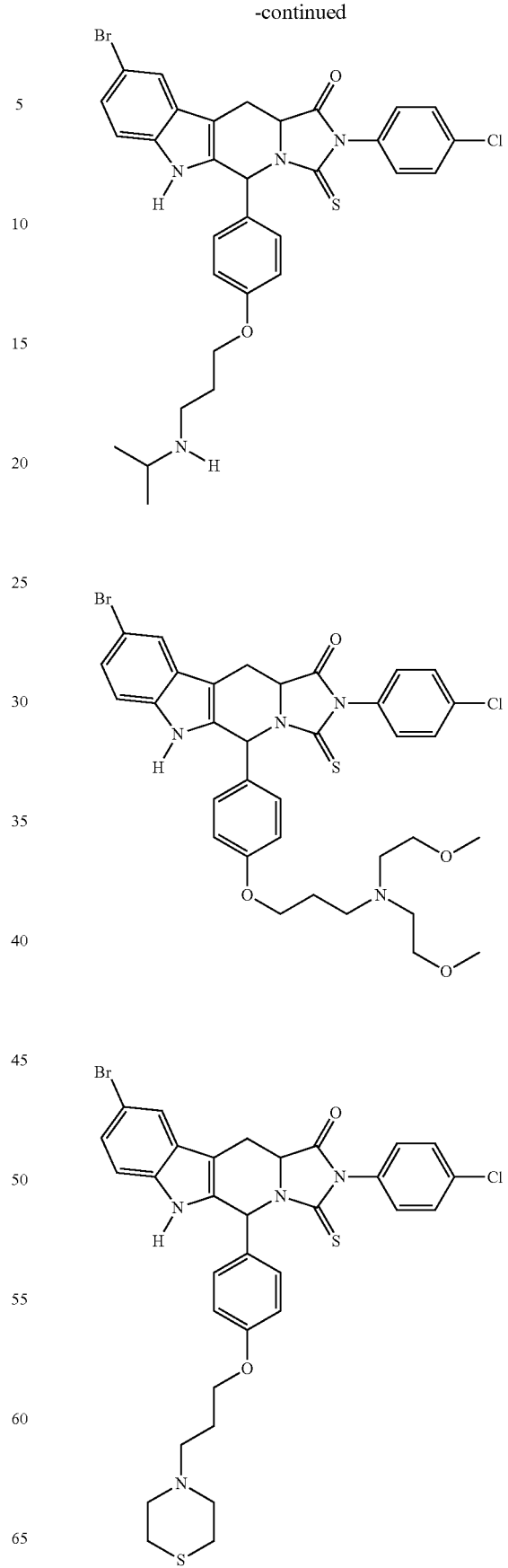

123
-continued
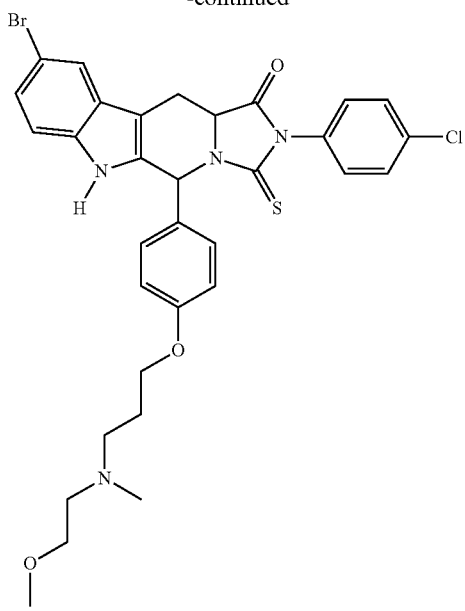
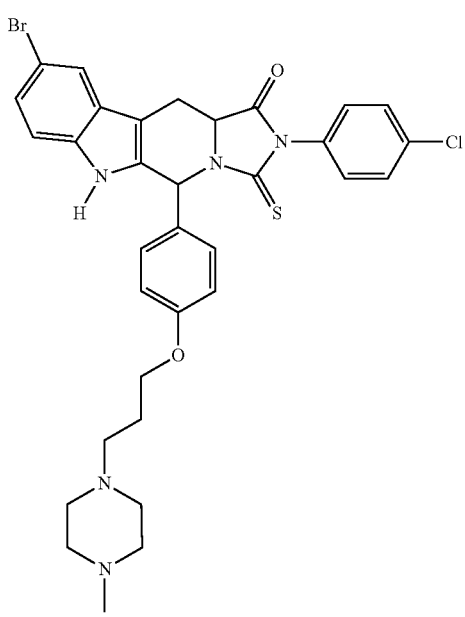 [SMILES: COCCN(C)CCCOc1ccc(C2c3[nH]c4ccc(Br)cc4c3CC3C(=O)N(c4ccc(Cl)cc4)C(=S)N32)cc1]
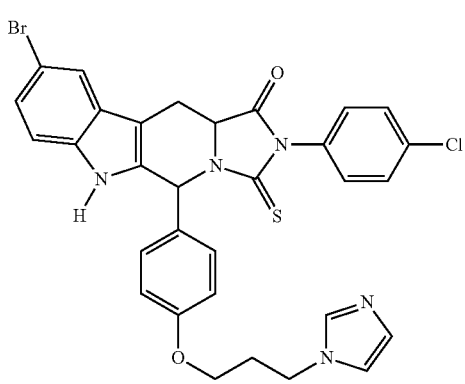
124
-continued
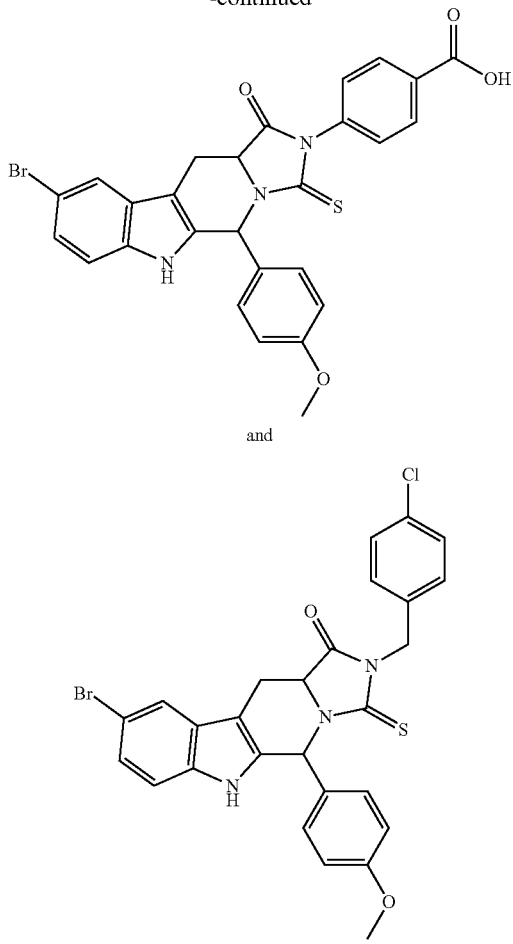
and
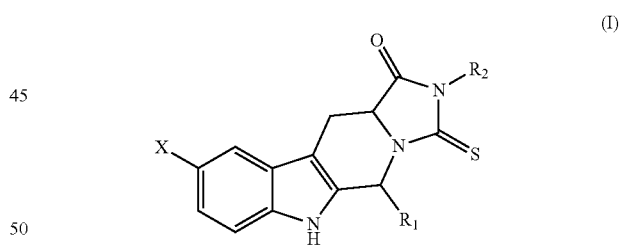
or a pharmaceutically acceptable salt, racemate or stereoisomer thereof.
2. A compound of Formula I,
(I)
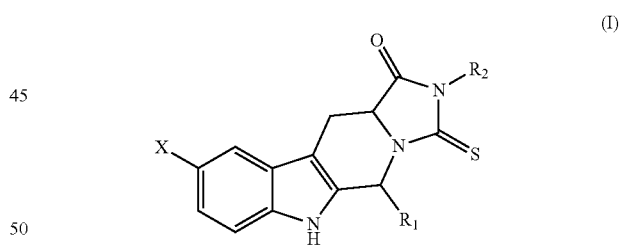
or a pharmaceutically acceptable salt, racemate or stereoisomer of said compound; wherein
X is hydrogen, a hydroxyl, a halogen, methyl or methoxy;
$R_1$ is selected from the group consisting of:
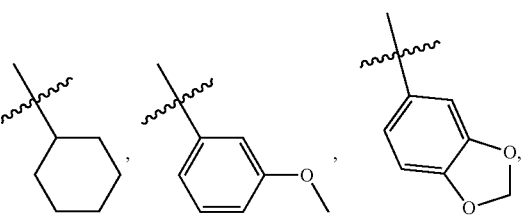

125
-continued
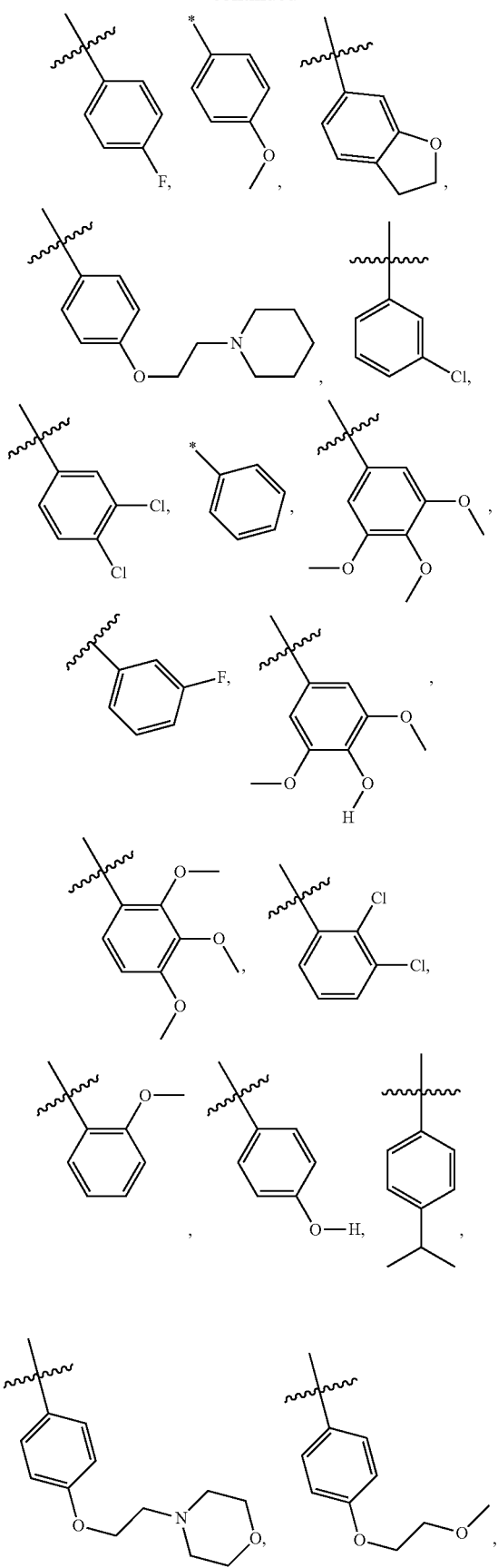
126
-continued
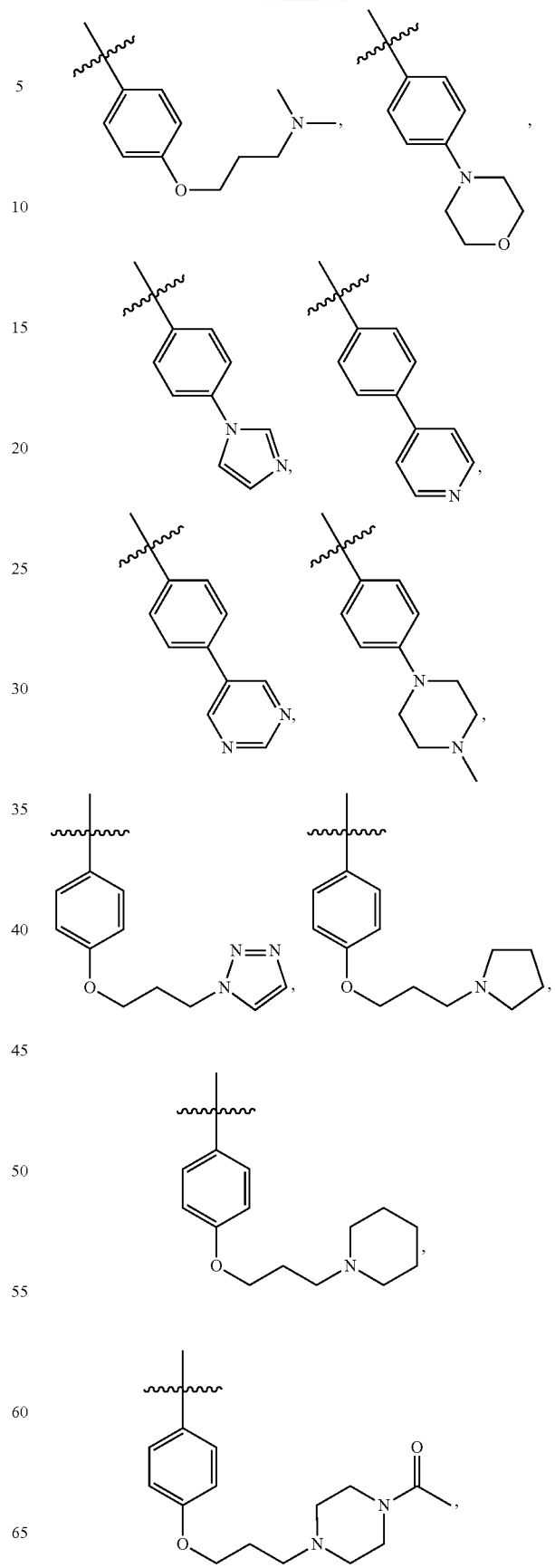

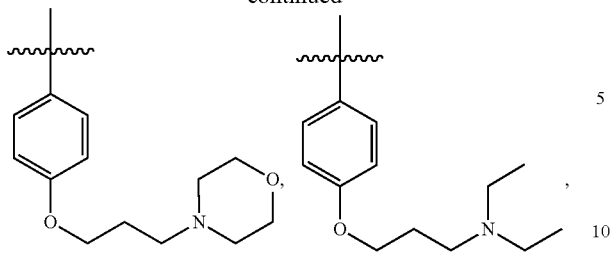
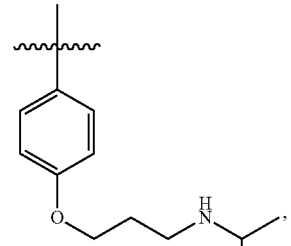
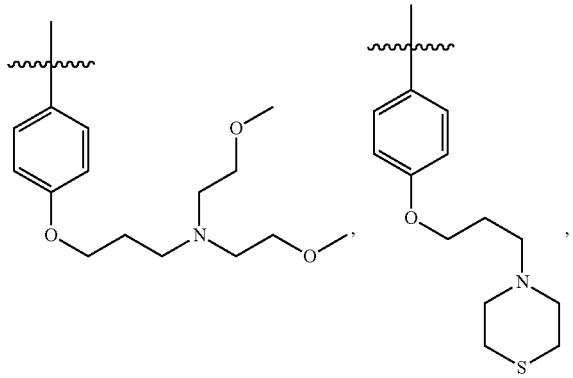
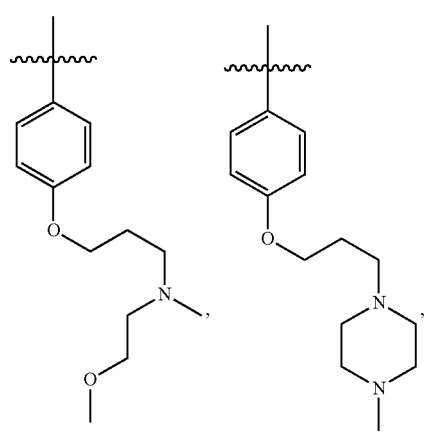
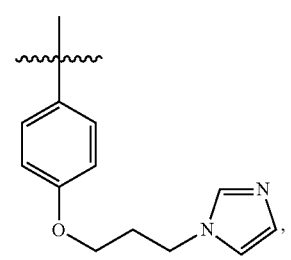
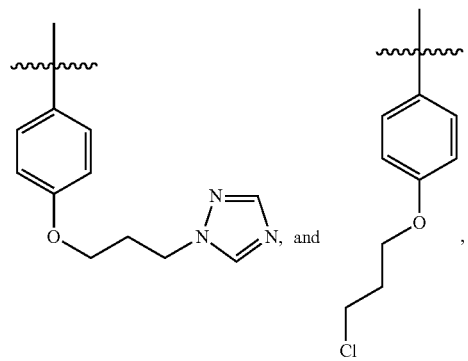
wherein ∿∿ indicates a point of attachment; and R₂ is selected from the group consisting of:
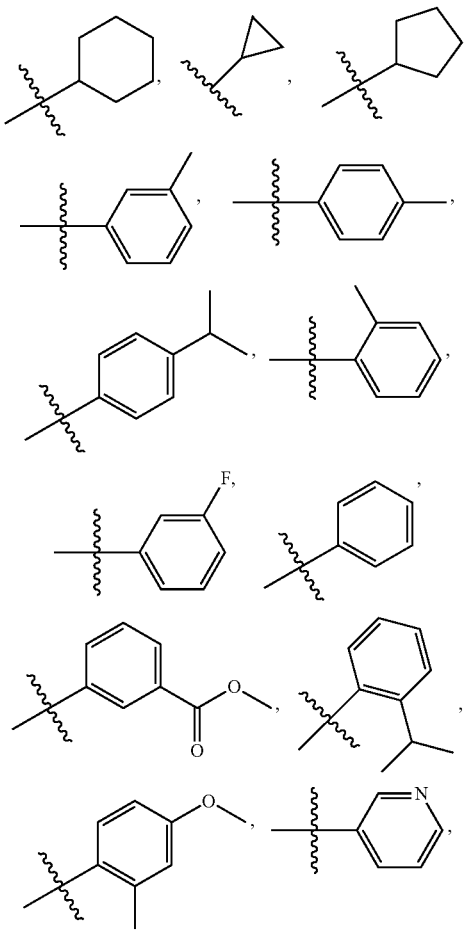
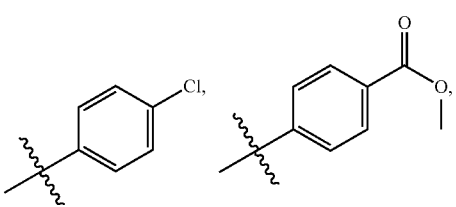

-continued
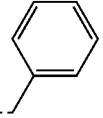
wherein ∼∼∼ and * each indicate a point of attachment, wherein, when R₁ is
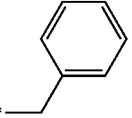
then R₂ is
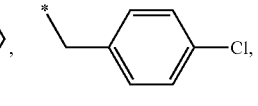

wherein, when R₁ is
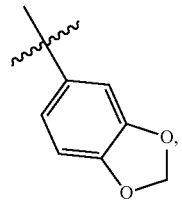 [SMILES: *c1ccc2c(c1)OCO2]
then R₂ is selected from the group consisting of:
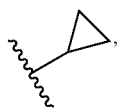 , 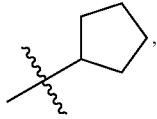 , 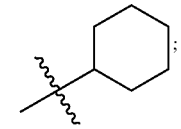 ;
and
  wherein, when R₁ is
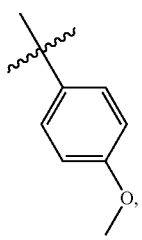 [SMILES: *c1ccc(OC)cc1]
then R₂ is selected from the group consisting of:
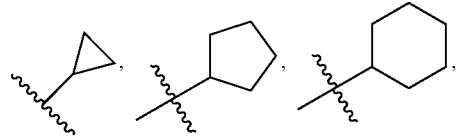
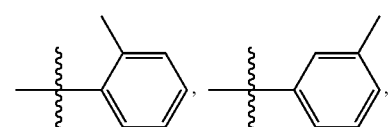
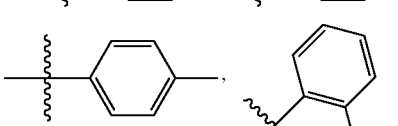
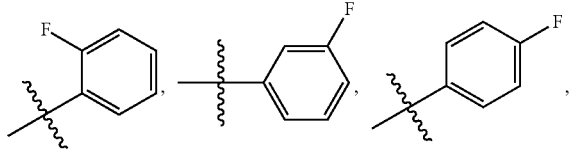
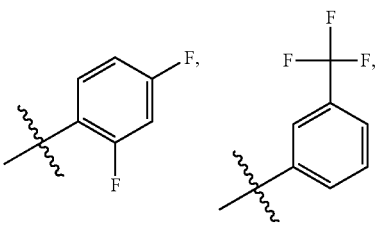
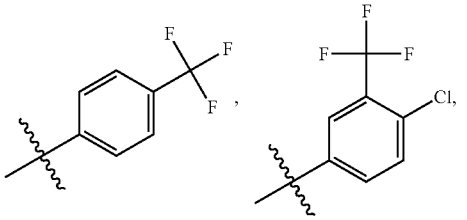
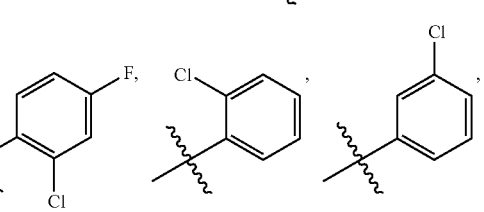
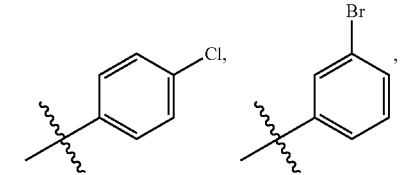
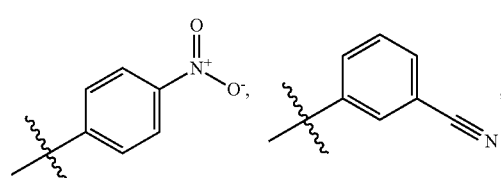
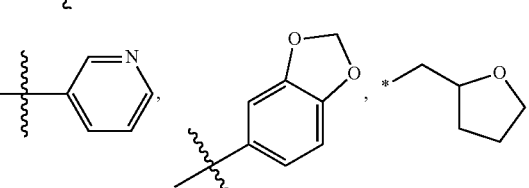
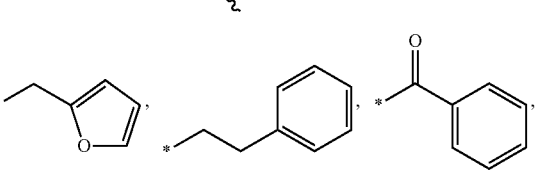
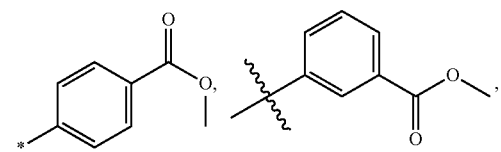
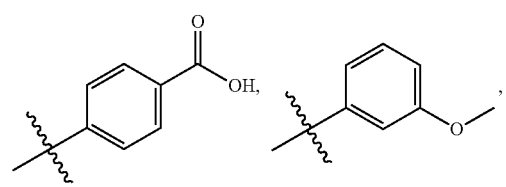

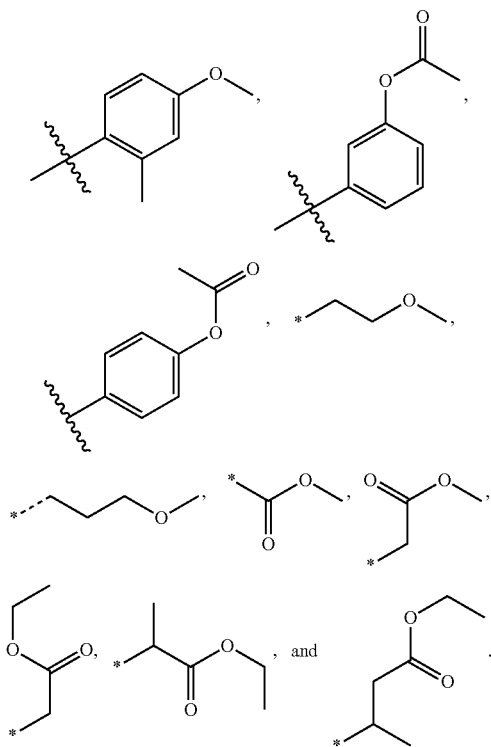
3. The compound of claim 2, wherein said compound is an 10S, 3aR isomer of a compound of Formula I.
4. The compound of claim 2, wherein said compound is an 5S, 11aR isomer of a compound of Formula I.
5. The compound of claim 2, wherein:
$R_1$ is selected from the group consisting of:
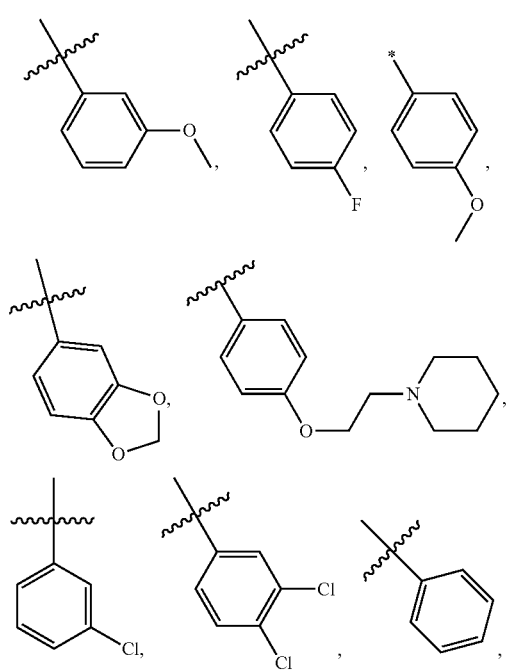
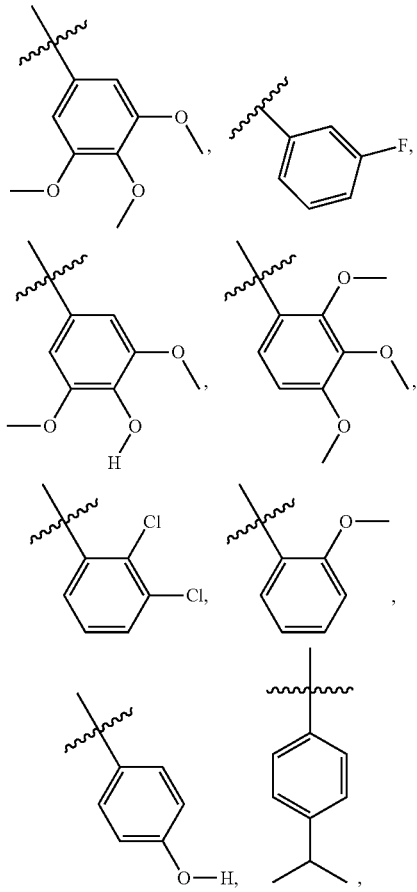
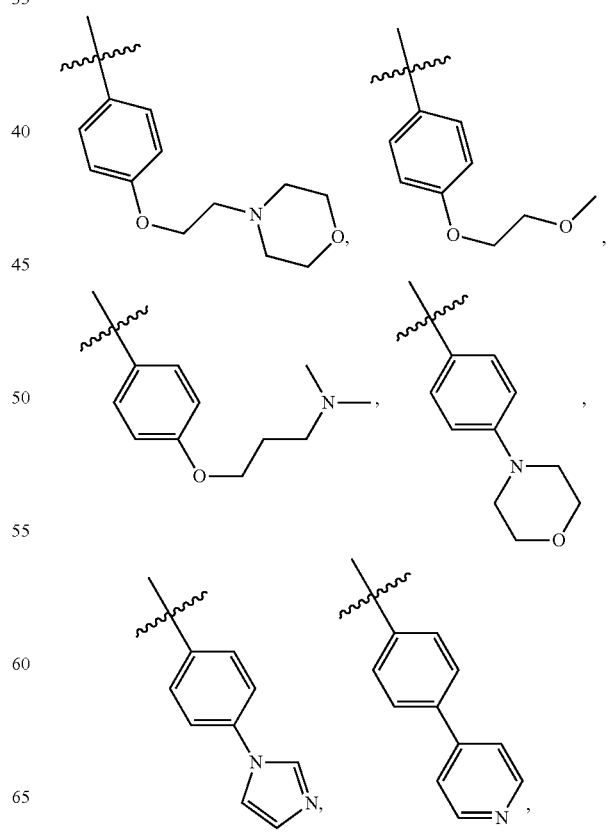

135
-continued
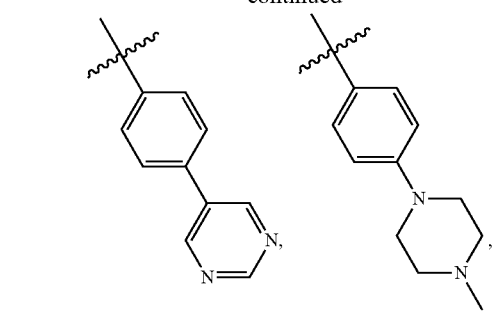
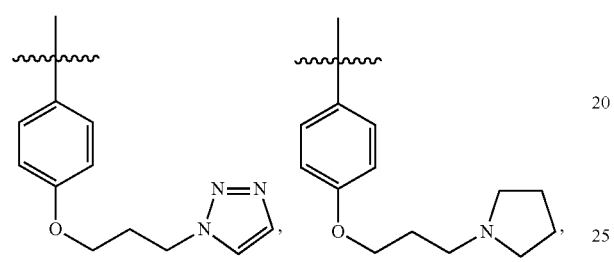
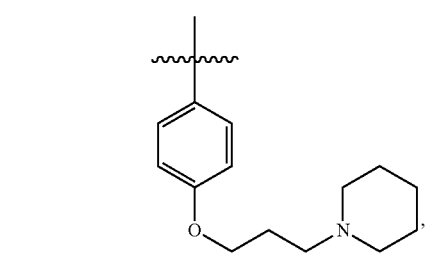
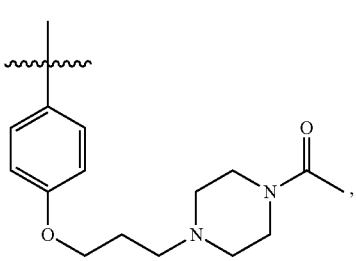
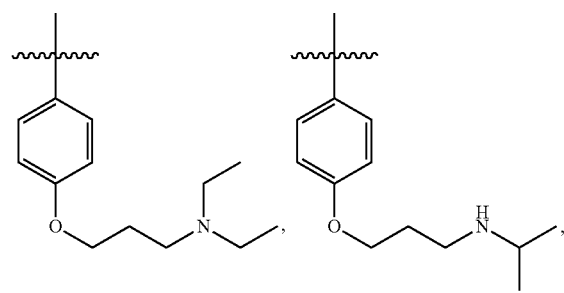
136
-continued
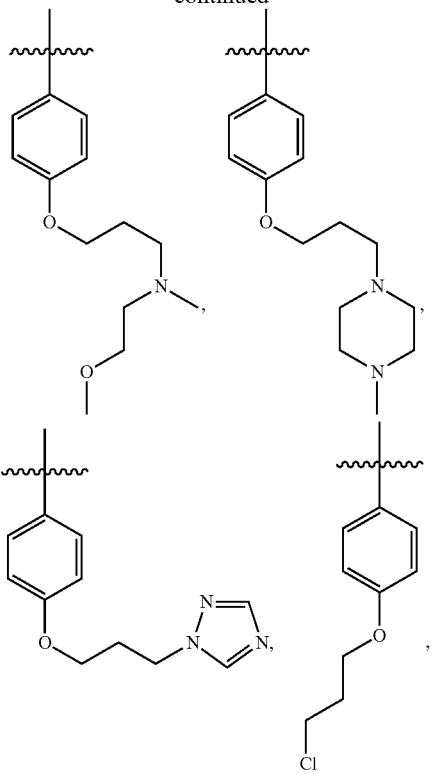
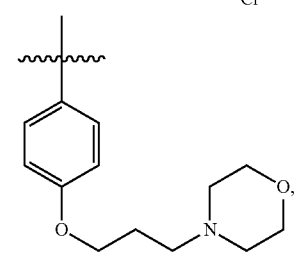
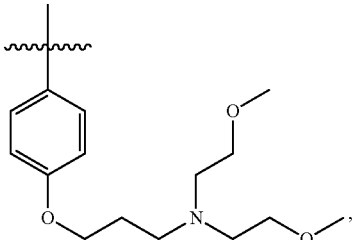
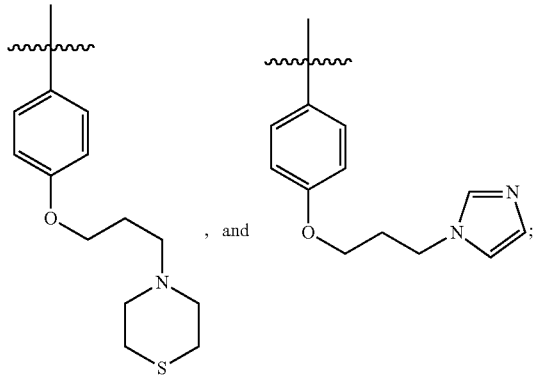 [SMILES: *c1ccc(OCCCN2CCSCC2)cc1 ; *c1ccc(OCCCn2ccnc2)cc1]

and
$R_2$ is selected from the group consisting of:
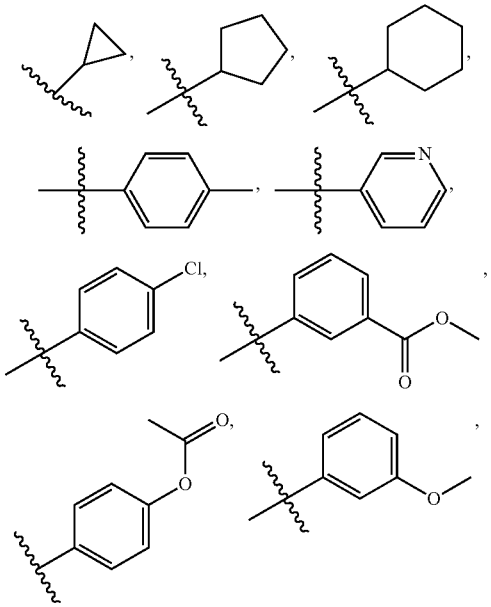
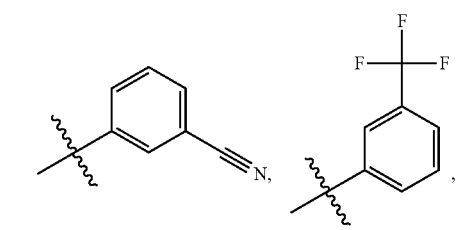
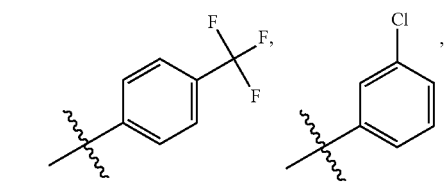
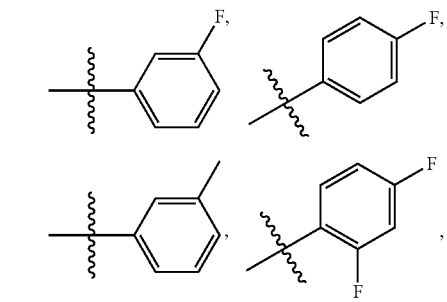
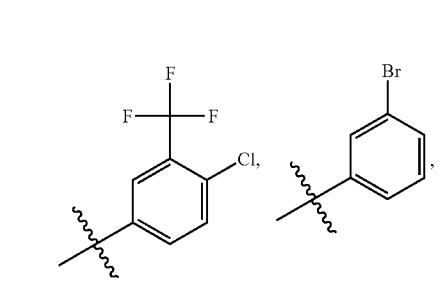
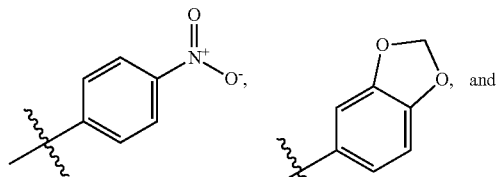
wherein, when $R_1$ is
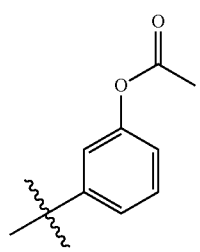 [SMILES: *c1cccc(OC(C)=O)c1]
then $R_2$ is
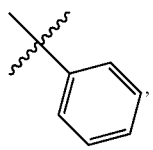
wherein, when $R_1$ is
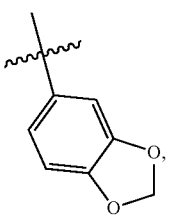 [SMILES: *c1ccc2c(c1)OCO2]
then $R_2$ is selected from the group consisting of:
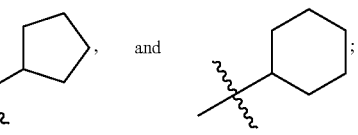

and
wherein, when R$_1$ is
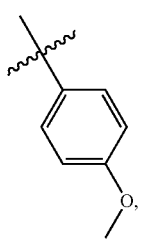
then R$_2$ is selected from the group consisting of:
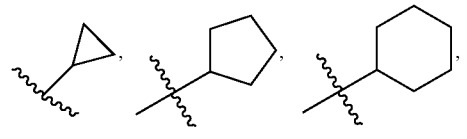
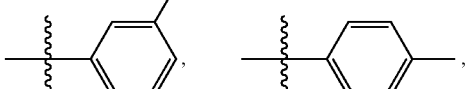
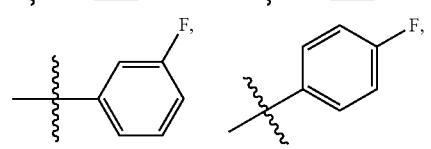
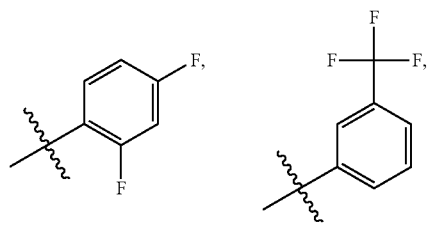
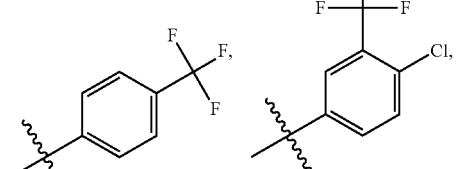
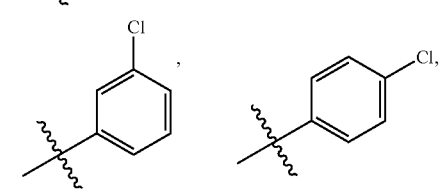
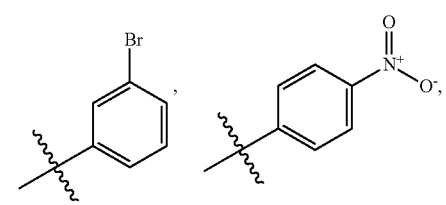
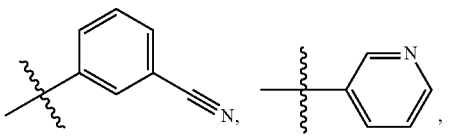
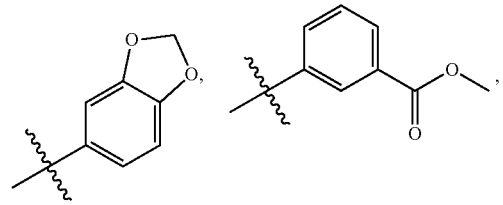
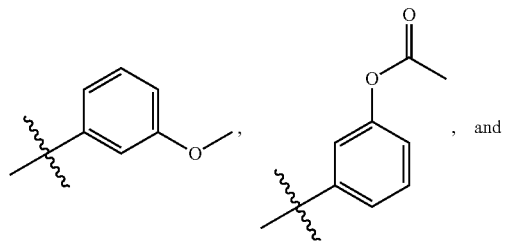
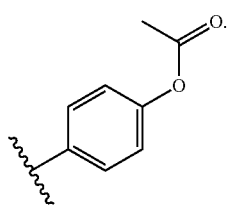 [SMILES: *c1ccc(OC(C)=O)cc1]
6. The compound of claim 2, wherein R$_1$ is selected from the group consisting of:
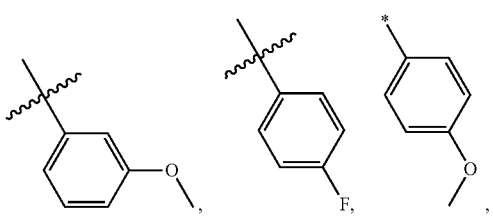
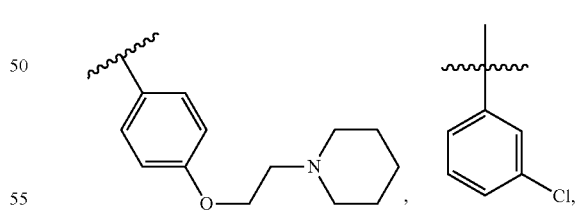
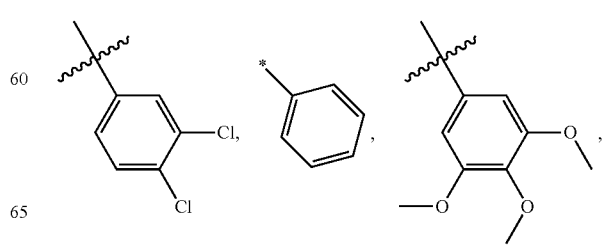

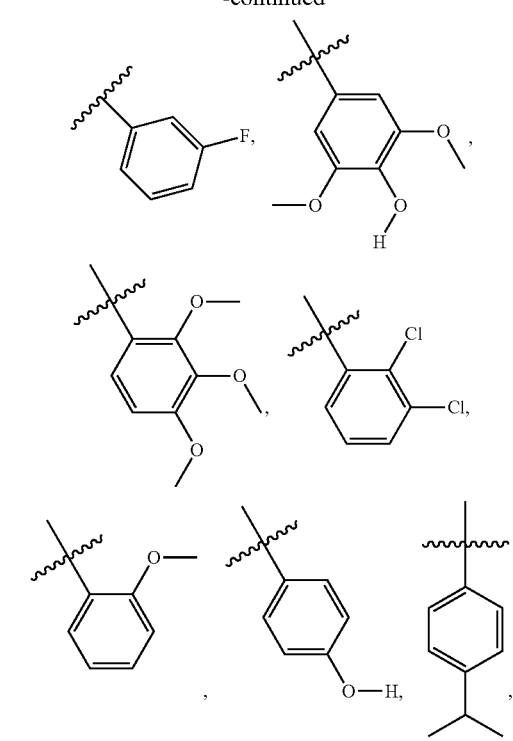
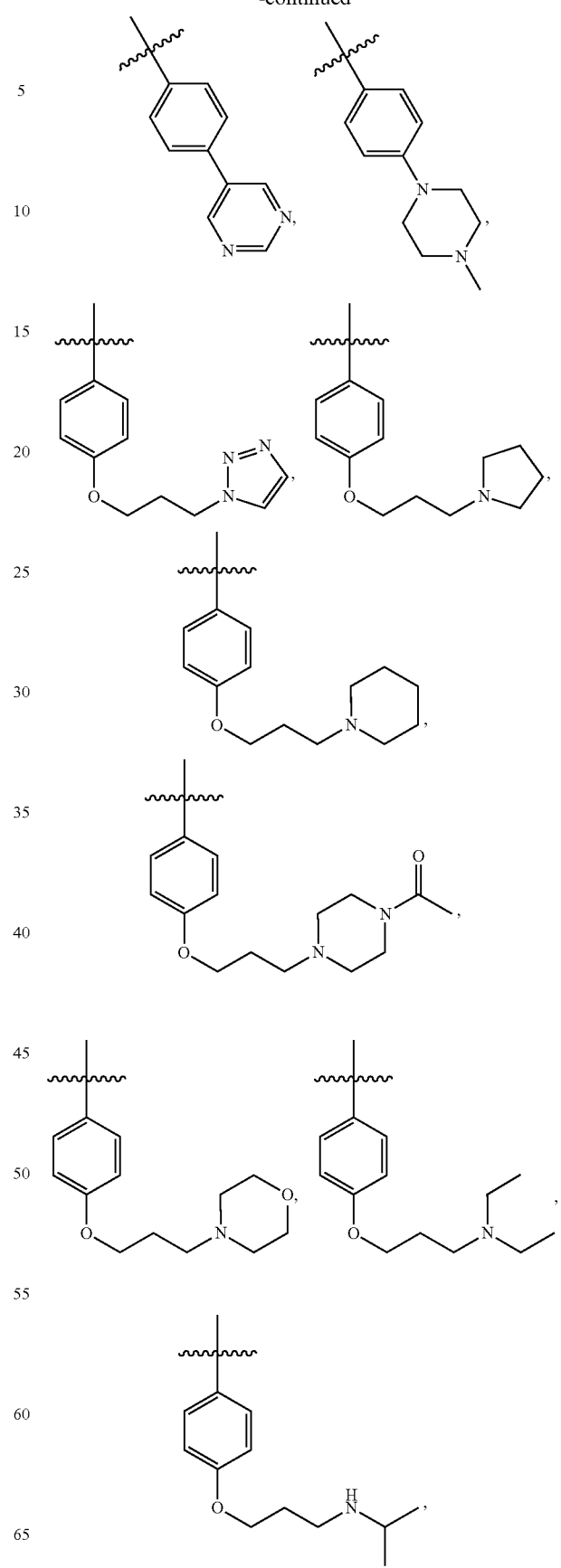

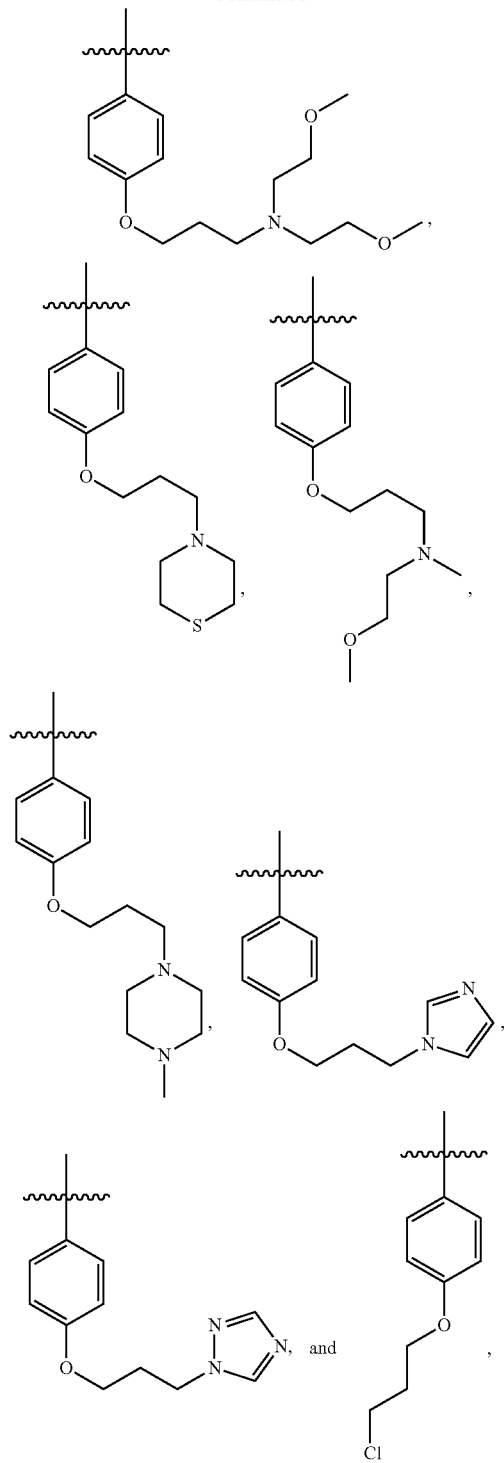
wherein ⁓ indicates a point of attachment, and R₂ is selected from the group consisting of:
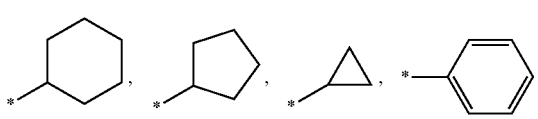
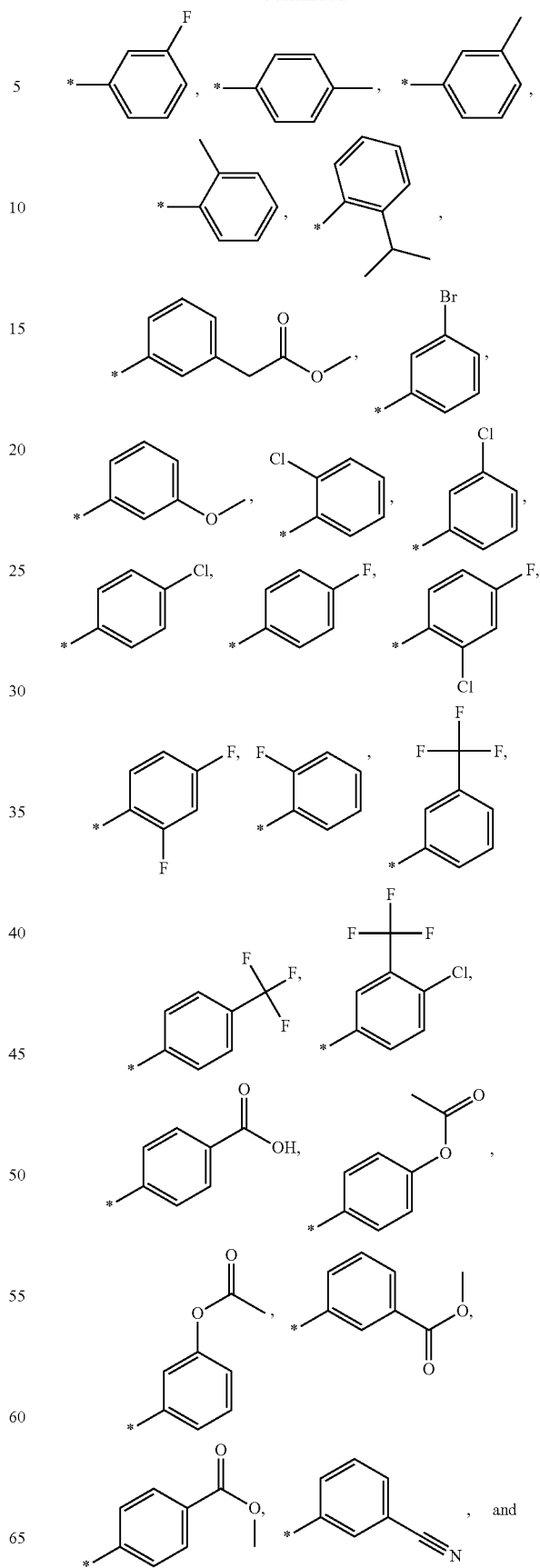

-continued
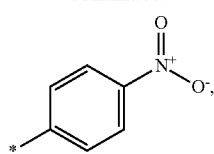
wherein * indicates a point of attachment,
wherein, when R₁ is
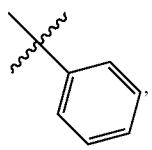 [SMILES: *c1ccccc1]
then R₂ is
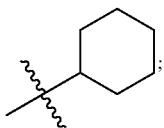 [SMILES: *C1CCCCC1]
and
wherein, when R₁ is
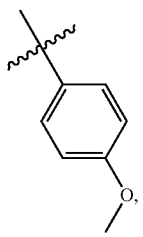 [SMILES: *c1ccc(OC)cc1]
then R₂ is selected from the group consisting of:
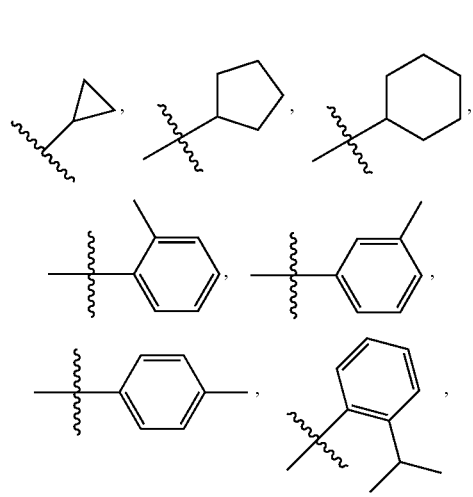
-continued
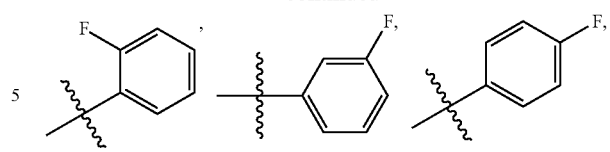
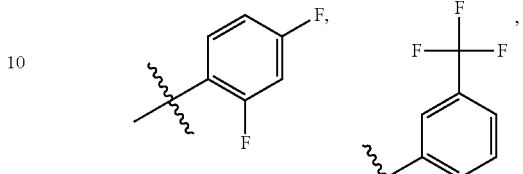
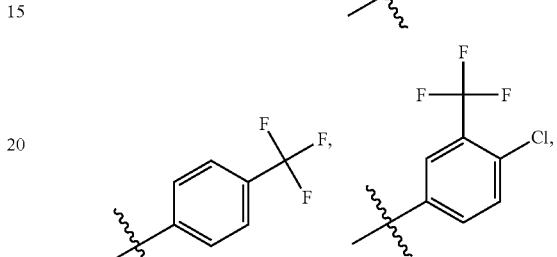
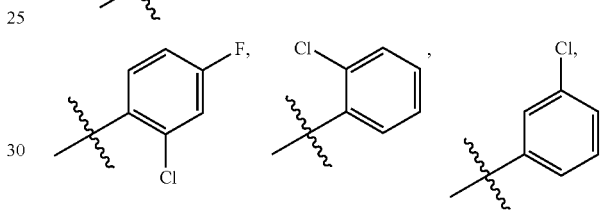
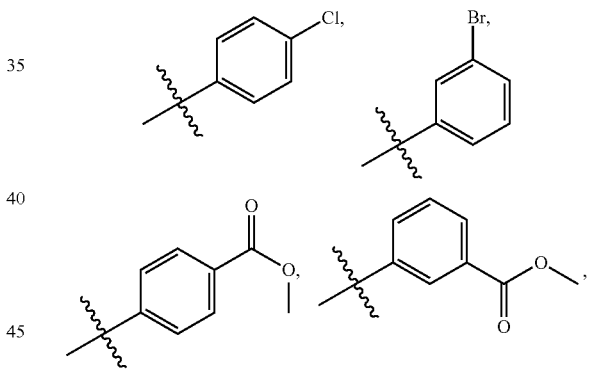
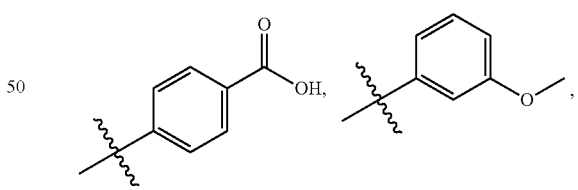
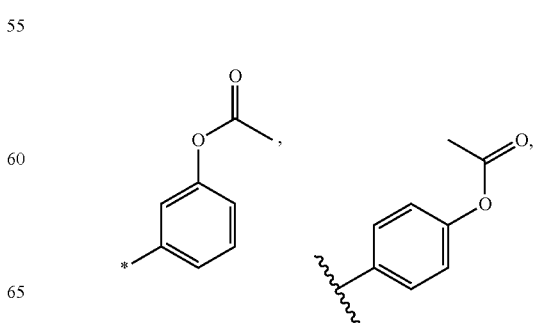

-continued
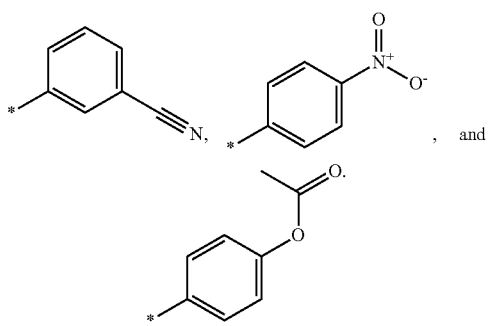
7. The compound of claim 2, wherein $R_1$ is:
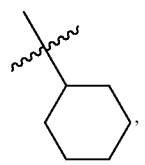 [SMILES: *C1CCCCC1]
wherein ∿∿ indicates a point of attachment, and $R_2$ is selected from the group consisting of:
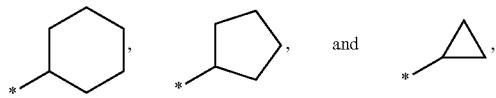
wherein * indicates a point of attachment.
8. The compound of claim 2, wherein $R_1$ is selected from the group consisting of:
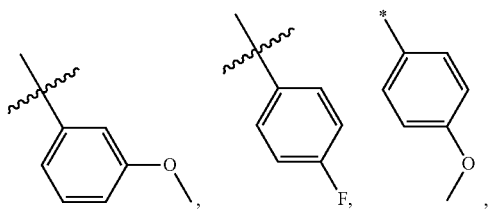
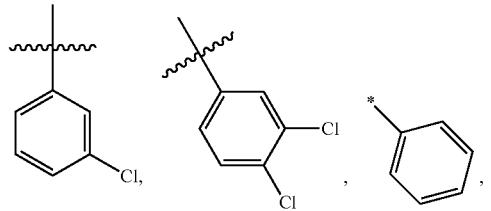
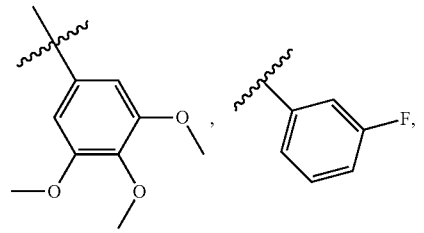
-continued
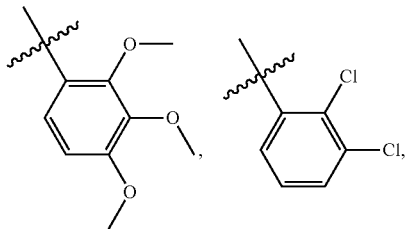
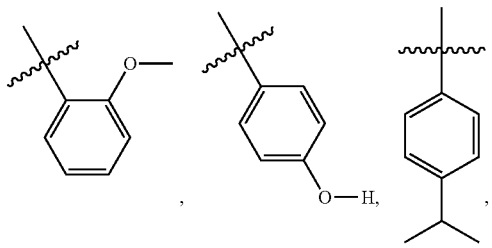
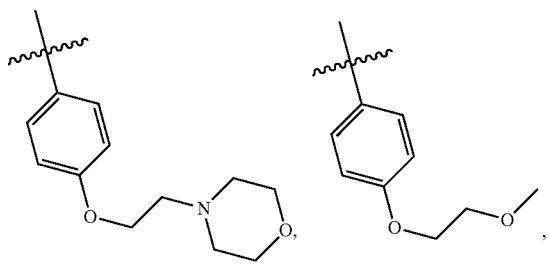
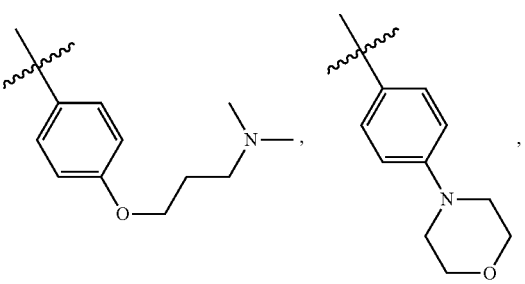
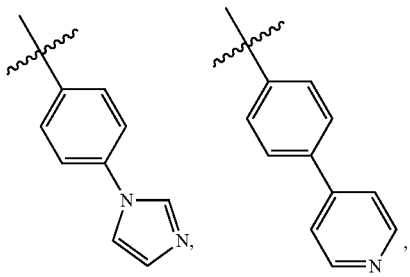
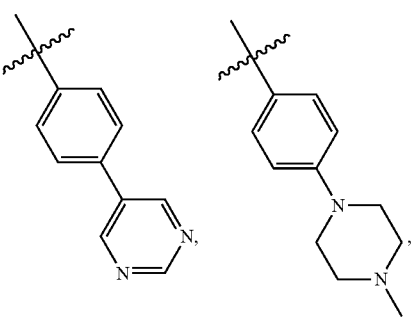

149
-continued
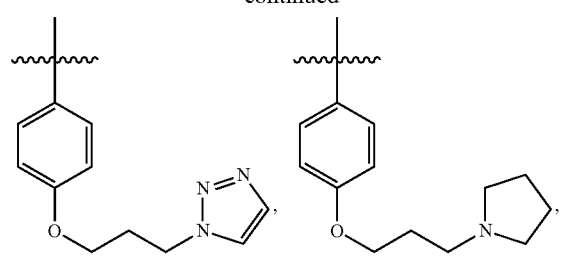
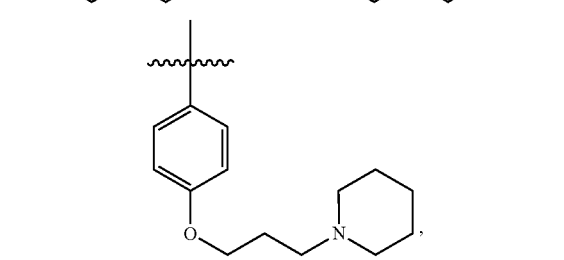
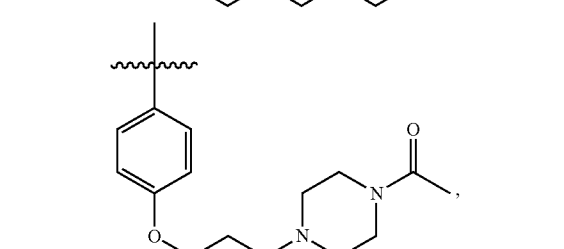
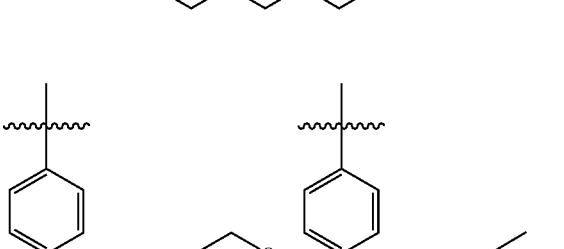
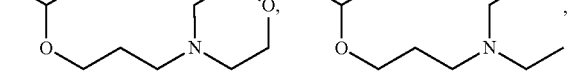
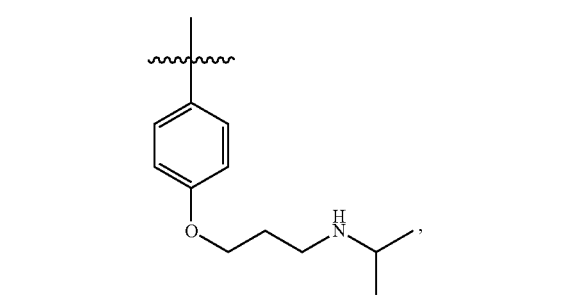
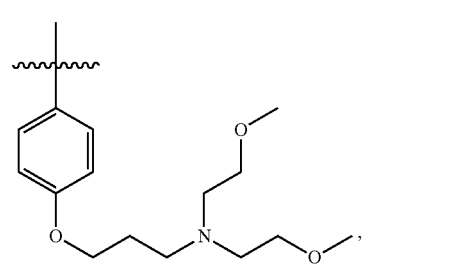
150
-continued
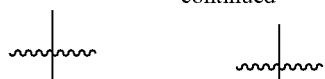
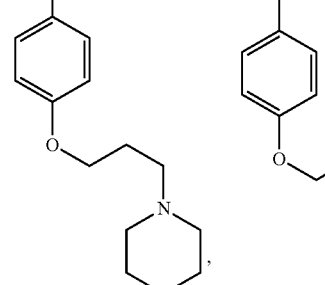
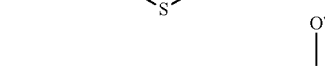, and
wherein ⁓ indicates a point of attachment, and $R_2$ is selected from the group consisting of:
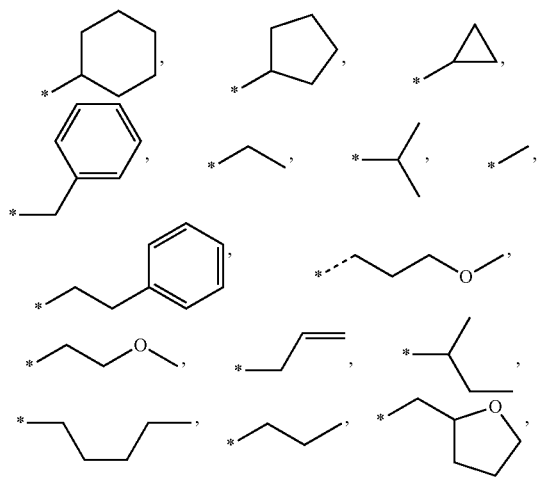

-continued
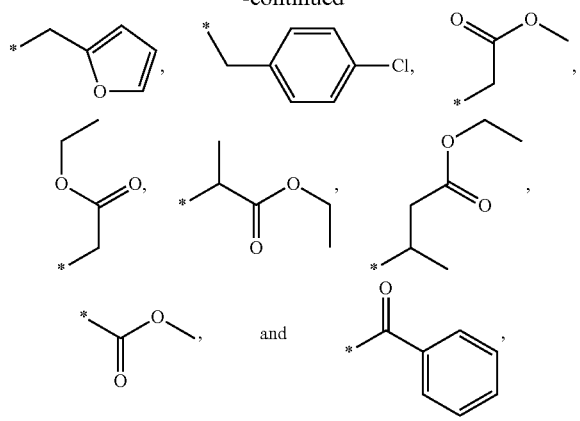
wherein * indicates a point of attachment,
wherein, when R₁ is
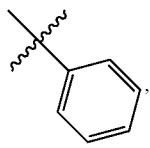 [SMILES: *c1ccccc1]
then R₂ is
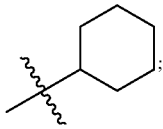 [SMILES: *C1CCCCC1]
and;
wherein, when R₁ is
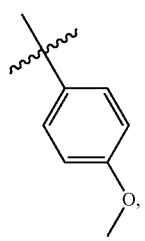
then $R_2$ is selected from the group consisting of:
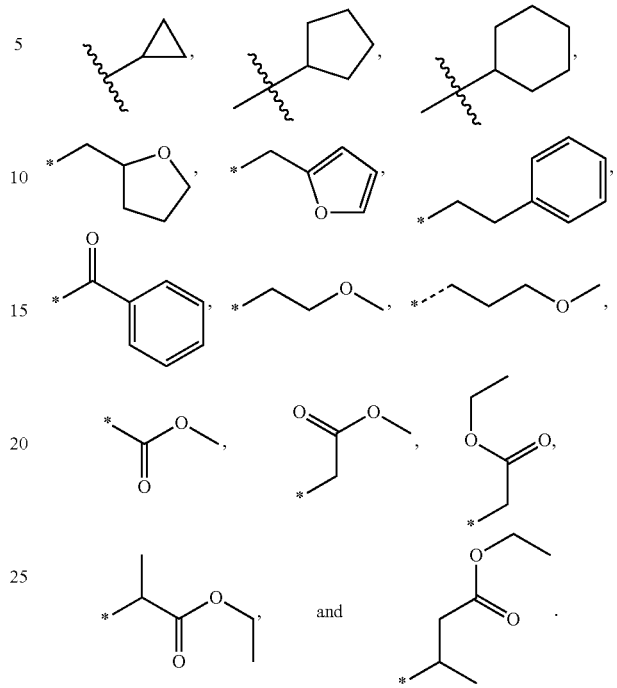
9. The compound of claim 2, wherein $R_1$ is selected from the group consisting of:
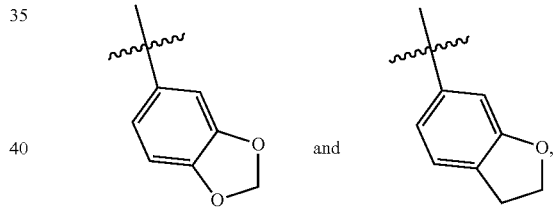
wherein ～ indicates a point of attachment, and
$R_2$ is selected from the group consisting of:
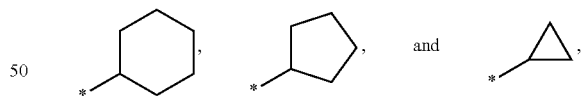
wherein * indicates a point of attachment.
* * * * *